United States Patent
Alvaro et al.

(10) Patent No.: US 6,642,240 B2
(45) Date of Patent: Nov. 4, 2003

(54) TREATING EMESIS IN A MAMMAL

(75) Inventors: Giuseppe Alvaro, Verona (IT);
Romano Di Fabio, Verona (IT);
Riccardo Giovannini, Verona (IT);
Giuseppe Guercio, Verona (IT); Yves St-Denis, Verona (IT); Antonella Ursini, Verona (IT)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/190,170

(22) Filed: Jul. 3, 2002

(65) Prior Publication Data

US 2003/0028021 A1 Feb. 6, 2003

Related U.S. Application Data

(63) Continuation of application No. 10/089,964, filed as application No. PCT/EP00/09722 on Oct. 5, 2000.

(30) Foreign Application Priority Data

Oct. 7, 1999 (GB) .............................................. 9923748

(51) Int. Cl.[7] .............................................. A61K 31/522
(52) U.S. Cl. .............................. 514/255.03; 514/255.03
(58) Field of Search ........................ 514/255.01, 255.03

(56) References Cited

U.S. PATENT DOCUMENTS

| | | | |
|---|---|---|---|
| 4,087,424 A | 5/1978 | Saikawa et al. | 260/268 |
| 4,110,327 A | 8/1978 | Saikawa et al. | 544/385 |
| 4,112,090 A | 9/1978 | Saikawa et al. | 424/251 |
| 4,219,554 A | 8/1980 | Saikawa et al. | 424/250 |
| 4,308,387 A | 12/1981 | Bjork et al. | 544/390 |
| 4,327,097 A | 4/1982 | Saikawa et al. | 424/250 |
| 4,379,152 A | 4/1983 | Saikawa et al. | 424/246 |
| 4,410,522 A | 10/1983 | Saikawa et al. | 424/246 |
| 5,464,788 A | 11/1995 | Bock et al. | 514/252 |
| 5,538,982 A | 7/1996 | Hagan et al. | 514/305 |
| 5,756,504 A | 5/1998 | Bock et al. | 514/252 |

FOREIGN PATENT DOCUMENTS

| | | |
|---|---|---|
| DE | 2519400 | 4/1978 |
| EP | 287734 | 10/1987 |
| EP | 293532 | 10/1987 |
| GB | 1508062 | 4/1975 |
| JP | 57/118587 | 7/1982 |
| WO | WO 95/25443 | 9/1995 |
| WO | WO 97/36592 | 10/1997 |
| WO | WO 97/36593 | 10/1997 |

OTHER PUBLICATIONS

Davis, David T., "Synthesis A. Biological Activity of a Series of Piperazine–2, 3–Diones," Journal of Antibiotics, vol XLII, No. 3, 1989, pp. 367–373.

*Primary Examiner*—Dwayne C. Jones
(74) *Attorney, Agent, or Firm*—Lorie Ann Morgan

(57) ABSTRACT

The invention relates to piperazine derivatives, to processes for their preparation, to pharmaceutical compositions containing them, and to their medical use. The novel compounds are antagonists of tachykinins, including substance P and other neurokinins.

31 Claims, No Drawings

TREATING EMESIS IN A MAMMAL

This Application is a continuation of U.S. patent application Ser. No. 10/089,964, filed May 8, 2002, which was filed pursuant to 35 U.S.C. §371 as a United States National Phase Application of International Application No. PCT/EP00/09722, filed Oct. 5, 2000, which claims priority to Great Britain Priority Patent Application Serial No. 9923748.9, filed Oct. 7, 1999.

The present invention relates to piperazine derivatives, to processes for their preparation, to pharmaceutical compositions containing them and to their medical use.

In particular the invention relates to novel compounds which are potent and specific antagonists of tachykinins, including substance P and other neurokinins.

The present invention provides compounds of formula (I)

wherein

R represents a halogen atom or a $C_{1-4}$ alkyl group;

$R_1$ represents hydrogen or a $C_{1-4}$ alkyl group;

$R_2$ represents hydrogen or a $C_{1-4}$ alkyl group;

$R_3$ represents a trifluoromethyl, a $C_{1-4}$ alkyl, a $C_{1-4}$ alkoxy, a trifluoromethoxy or a halogen group;

$R_4$ represents hydrogen, a $(CH_2)qR_7$ or a $(CH_2)rCO(CH_2)pR_7$ group;

$R_5$ represents hydrogen, a $C_{1-4}$ alkyl or a $COR_6$ group;

$R_6$ represents hydrogen, hydroxy, amino, methylamino, dimethylamino, a 5 membered heteroaryl group containing 1 to 3 heteroatoms selected independently from oxygen, sulphur and nitrogen or a 6 membered heteroaryl group containing 1 to 3 nitrogen atoms;

$R_7$ represents hydrogen, hydroxy, or $NR_8R_9$ wherein $R_8$ and $R_9$ represent independently hydrogen or $C_{1-4}$ alkyl optionally substituted by hydroxy or by amino;

$R_{10}$ represents hydrogen;

m is zero or an integer from 1 to 3; n is zero or an integer from 1 to 3; both p and r are independently zero or an integer from 1 to 4; q is an integer from 1 to 4;

and pharmaceutically acceptable salts and solvates thereof.

A further embodiment of the invention provides compounds of formula (I) and pharmaceutically acceptable salts and solvates thereof, wherein R represents a halogen atom or a $C_{1-4}$ alkyl group;

$R_1$ represents hydrogen or a $C_{1-4}$ alkyl group;

$R_2$ represents hydrogen, a $C_{1-4}$ alkyl, $C_{2-6}$ alkenyl or a $C_{3-7}$ cycloalkyl group; or $R_1$ and $R_2$ together with nitrogen and carbon atom to which they are attached respectively represent a 5 to 6 membered heterocyclic group;

$R_3$ represents a trifluoromethyl, a $C_{1-4}$ alkyl, a $C_{1-4}$ alkoxy, a trifluoromethoxy or a halogen group;

$R_4$ represents hydrogen, a $(CH_2)qR_7$ or a $(CH_2)rCO(CH_2)pR_7$ group;

$R_5$ represents hydrogen, a $C_{1-4}$ alkyl or a $COR_6$ group;

$R_6$ represents hydrogen, hydroxy, amino, methylamino, dimethylamino a 5 membered heteroaryl group containing 1 to 3 heteroatoms selected from oxygen, sulphur and nitrogen or a 6 membered heteroaryl group containing 1 to 3 nitrogen atoms;

$R_7$ represents hydrogen, hydroxy or $NR_8R_9$ wherein $R_8$ and $R_9$ represent independently hydrogen or $C_{1-4}$ alkyl optionally substituted by hydroxy or by amino;

$R_{10}$ represents hydogen, a $C_{1-4}$ alkyl group or $R_{10}$ together with $R_2$ represents a $C_{3-7}$ cycloalkyl group;

m is zero or an integer from 1 to 3; n is zero or an integer from 1 to 3; both p and r are independently zero or an integer from 1 to 4; q is an integer from 1 to 4; provided that, when $R_1$ and $R_2$ together with nitrogen and carbon atom to which they are attached respectively represent a 5 to 6 membered heterocyclic group, i) m is 1 or 2:ii) when m is 1, R is not fluorine and iii) when m is 2, the two substituents R are not both fluorine.

Suitable pharmaceutically acceptable salts of the compounds of general formula (I) include acid addition salts formed with pharmaceutically acceptable organic or inorganic acids, for example hydrochlorides, hydrobromides, sulphates, alkyl- or arylsulphonates (e.g. methanesulphonates or p-toluenesulphonates), phosphates, acetates, citrates, succinates, tartrates, fumarates and maleates.

The solvates may, for example, be hydrates.

References hereinafter to a compound according to the invention include both compounds of formula (I) and their pharmaceutically acceptable acid addition salts together with pharmaceutically acceptable solvates.

It will be appreciated by those skilled in the art that the compounds of formula (I) contain at least one chiral centre.

Further asymmetric carbon atoms are possible in the compounds of formula (I).

Thus, for example, when $R_2$ is a $C_{1-4}$ alkyl, a $C_{2-6}$ alkenyl or a $C_{3-7}$ cycloalkyl group, and $R_5$ and $R_{10}$ are hydrogens, the compounds of formula (I) possess two asymmetric carbon atoms and these may be represented by the formulae (1a, 1b, 1c and 1d)

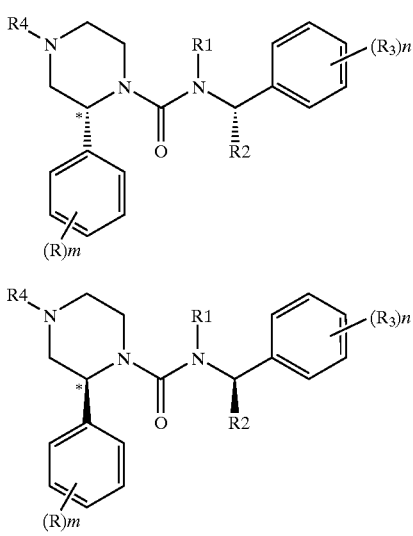

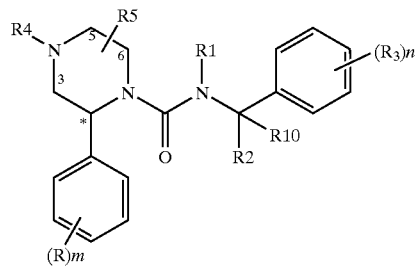

The wedge shaped bond indicates that the bond is above the plane of the paper. The broken bond indicates that the bond is below the plane of the paper.

The configuration shown for the chiral carbon atom indicated as * in formulae 1b and 1d is hereinafter referred to as the β configuration and in formulae 1a and 1c as α configuration. In general, in the specific compounds named below, the β configuration at the chiral carbon atom indicated as * corresponds to the S isomer and the α configuration corresponds to the R isomer.

The configuration of the two chiral carbon atoms shown in formulae 1a and 1b is hereinafter referred to as anti configuation and in formulae 1c and 1d as the syn configuration.

Furthermore, when $R_2$ is a $C_{1-4}$ alkyl, a $C_{2-6}$ alkenyl or a $C_{3-7}$ cycloalkyl group or $R_{10}$ is a $C_{1-4}$ alkyl group and $R_5$ is a $C_{1-4}$ alkyl or a $COR_6$ group, the compounds of the invention possess three asymmetric carbon atoms.

The assignment of the R and S configuration of the asymmetric carbon atoms of the compounds of the invention has been made according to the rules of Chan, Ingold and Prelong 1956, 12, 81.

It is to be understood that all enantiomers and diastereisomers and mixtures thereof are encompassed within the scope of the present invention.

The term alkyl as used herein as a group or a part of the group refers to a straight or branched alkyl group containing from 1 to 4 carbon atoms; examples of such groups include methyl, ethyl, propyl, isopropyl, n-butyl, isobutyl, or tert butyl.

The term halogen refers to a fluorine, chlorine, bromine or iodine atom.

The term $C_{2-6}$ alkenyl defines straight or branched chain hydrocarbon radicals containing one double bond and having from 2–6 carbon atoms such as, for example, ethenyl, 2-propenyl, 3-butenyl, 2-butenyl, 2-pentenyl, 3-pentenyl, 3-methyl-2-butenyl or 3-hexenyl.

The term $C_{3-7}$ cycloalkyl group means a non aromatic monocyclic hydrocarbon ring of 3 to 7 carbon atom such as, for example, cyclopropyl, cyclobutyl, cyclopentyl, cyclohexyl or cycloheptyl.

The term $C_{1-4}$ alkoxy group may be a straight or a branched chain alkoxy group, for example methoxy, ethoxy, propoxy, prop-2-oxy, butoxy, but-2-oxy or methylprop-2-oxy.

When $R_1$ and $R_2$ together with nitrogen and carbon atom to which they are attached respectively represent a 5 to 6 membered heterocyclic group this group is saturated or contains a single double bond. This may be a 3,6-dihydro-2H-pyridin-1yl, a piperidin-1-yl or a pyrrolidin 1-yl group. When $R_6$ is a 5 or 6 membered heteroaryl group according to the invention they include furanyl, thiophenyl, imidazolyl, thiazolyl, oxazolyl, pyridyl or pyrimidinyl.

The group $R_5$ may be in position 3, 5 or 6 of the piperazine ring of compounds of formula (I)

When R represents halogen this is suitably chlorine or more preferably fluorine or when R is $C_{1-4}$ alkyl this is suitably methyl or ethyl wherein m is 0 or an integer from 1 to 2.

Suitable values for $R_1$ include hydrogen, a methyl, an ethyl or a propyl group.

Suitable values for $R_2$ include hydrogen, a methyl, an ethyl a propyl, an isopropyl, a 2-propenyl or a cyclopropyl group.

Suitable values for $R_3$ include a methyl, an ethyl or a trifluoromethyl group.

When $R_4$ is $(CH_2)_qR_7$ or $(CH_2)_rCO(CH_2)_pR_7$, $R_7$ is suitably hydrogen, hydroxy, $NR_9R_8$ e.g. $NH_2$, $NH(C_{1-4}$ alkyl) e.g. NH methyl or $N(C_{1-4}$ alkyl$)_2$ e.g. $N(methyl)_2$, $NH(C_{1-4}$ alkyl$)NH_2$ e.g. $NH(ethyl)NH_2$, $NH(C_{1-4}$ alkyl) wherein q is 1 or 2 and both p and rare independently zero or an integer from 1 to 2.

Suitable values for $R_5$ include hydrogen or a $C_{1-4}$ alkyl (e.g. methyl) group.

R is preferably a halogen atom (e.g. fluorine or chlorine) and/or a $C_{1-4}$ alkyl (e.g. methyl) group and m is preferably an integer from 1 to 2.

Suitable values for $R_{10}$ include hydrogen, a $C_{1-4}$ alkyl (e.g. methyl) group or together with $R_2$ represents a a $C_{3-7}$ cycloalkyl (i.e. cyclopropyl) group.

$R_1$ is preferably a hydrogen atom or a methyl group.

$R_2$ is preferably a hydrogen atom, a methyl, isopropyl, 2-propenyl, or a cyclopropyl group or together with $R_1$ is a 3,6-dihydro-2H-pyridin-1yl, a piperidin-1-yl or a pyrrolidin 1-yl group.

$R_3$ is preferably a trifluoromethyl group.

$R_4$ is preferably a hydrogen atom, an amino $C_{1-4}$ alkyl (e.g. aminoethyl), an aminoacetyl or an amino($C_{1-4}$alkylaminocarbonyl) group.

$R_5$ is preferably a hydrogen atom, a methyl or ethyl group.

$R_{10}$ is preferably a hydrogen atom, a methyl group or together with $R_2$ is cyclopropyl.

A preferred group of compounds of formula (I) are those in which the carbon atom shown as * is in the β configuration.

A preferred class of compounds of formula (I) are those wherein R is selected independently from a halogen or a methyl group, wherein m is 1 or 2. More preferably m is 2. Within this class those wherein R is at the 2 and 4 position are particularly preferred.

Compounds of formula (I) wherein $R_3$ is a trifluoromethyl group and n is 2 represent a preferred class of compounds and within this class $R_3$ is preferably at the 3 and 5 position.

A further preferred class of compounds of formula (I) are those wherein $R_4$ is hydrogen, a $(CH_2)rCO(CH_2)pR_7$ or $(CH_2)qR_7$ group, wherein $R_7$ represents an amine. Within this class, those wherein both p and r are independently zero or 1 or q is 1 or 2 are particularly preferred.

A particularly preferred group of compounds of formula (I) is that wherein R is selected independently from halogen or methyl, $R_3$ is trifluoromethyl both at the 3 and 5 position, $R_1$ is hydrogen or methyl, $R_2$ is hydrogen, methyl, 2-propenyl, or cyclopropyl group or together with $R_1$ is a 3,6-dihydro-2H-pyridin-1yl, a piperdin 1-yl or a pyrrolidin 1-yl group, $R_{10}$ represents hydrogen, a methyl or $R_{10}$ together with $R_2$ is a cyclopropyl group, $R_4$ is hydrogen, an aminoacetyl or amino ethyl group and $R_5$ is hydrogen or a methyl group.

A particularly preferred group of compounds of formula (I) is that wherein R is selected independently from halogen or methyl, $R_3$ is trifluoromethyl both at the 3 and 5 position, $R_1$ is hydrogen or methyl, $R_2$ is hydrogen, methyl, 2-propenyl or cyclopropyl group or together with $R_1$ is a 3,6-dihydro-2H-pyridin-1yl, a piperidin-1-yl or a pyrrolidin 1-yl group, $R_{10}$ represents hydrogen, a methyl or $R_{10}$ together with $R_2$ is a cyclopropyl group, $R_4$ is hydrogen, and $R_5$ is hydrogen.

A further particularly preferred group of compounds of formula (I) is that wherein R is selected independently from halogen or methyl and m is 2, $R_3$ is trifluoromethyl both at the 3 and 5 position, $R_1$ and $R_2$ are independently hydrogen or methyl, $R_4$ is hydrogen and $R_5$ is hydrogen.

Preferred compounds according to the invention are:

2-(4-fluoro-2-methyl-phenyl)-piperazine-1-carboxylic acid (3,5-bis-trifluoromethyl-benzyl)-methyl-amide;

2-(2-isopropyl-phenyl)-piperazine-1-carboxylic acid (3,5-bis-trifluoromethyl-benzyl)-methyl-amide;

2-(4-fluoro-3-methyl-phenyl)-piperazine-1-carboxylic acid (3,5-bis-trifluoromethyl-benzyl)-methyl-amide;

2-(2,4-difluoro-phenyl)-piperazine-1-carboxylic acid (3,5-bis-trifluoromethyl-benzyl)-methyl-amide;

2-(4-fluoro-2-methyl-phenyl)-piperazine-1-carboxylic acid [1-(3,5-bis-trifluoromethyl-phenyl)ethyl]-methyl-amide;

2-(4-fluoro-phenyl)-piperazine-1-carboxylic acid (3,4-bis-trifluoromethyl-benzyl)-methyl-amide;

2-Phenyl-piperazine-1-carboxylic acid (3,5-bis-trifluoromethyl-benzyl)-methyl-amide;

2-(2,4-dichloro-phenyl)-piperazine-1-carboxylic acid (3,5-bistrifluoro methyl-benzyl)-methyl-amide;

2-(3,4-dichloro-phenyl)-piperazine-1-carboxylic acid (3,5-bistrifluoro methyl-benzyl)-methyl-amide;

2-(4-fluoro-2-methyl-phenyl)-3-methyl-piperazine-1-carboxylic acid (3,5-bis-trifluoromethyl-benzyl)-methyl-amide;

2-(2-methyl-4-fluoro-phenyl)-6-Methyl-piperazine-1-carboxylic acid (3,5-bis-trifluoromethyl-benzyl)-methyl-amide;

2-(4-fluoro-2-methyl-phenyl)-piperazine-1-carboxylic acid [1-(3,5-bis-trifluoromethyl-phenyl)ethyl]-methyl-amide;

4-(2-Amino-acetyl)-2-(S)-(4-fluoro-2-methyl-phenyl)-piperazine-1-carboxylic acid (3,5-bis-trifluoromethyl-benzyl)-methyl-amide;

2-(S)-(4-Fluoro-2-methyl-phenyl)-4-(piperidine-4-carbonyl)-piperazine-1-carboxylic acid (3,5-bis-trifluoromethyl-benzyl)-methyl-amide;

4-(2-Amino-ethyl)-2-(S)-(4-fluoro-2-methyl-phenyl)-piperazine-1-carboxylic acid (3,5-bis-trifluoromethyl-benzyl)-methyl-amide;

2-(S)-(4-Fluoro-2-methyl-phenyl)-piperazine-1-carboxylic acid [(1-3,5-bis-trifluoromethyl-phenyl)-cyclopropyl]-methyl-amide;

[2-(3,5-Bis-trifluoromethyl-phenyl)-pyrrolidin-1-yl]-[2-(S)-(4-fluoro-2-methyl-phenyl)-piperazin-1-yl]-methanone;

[2-(3,5-Bis-trifluoromethyl-phenyl)-3,6-dihydro-2H-pyridyn-1-yl]-[2-(S)-(4-fluoro-2-methyl-phenyl)-piperazin-1-yl]-methanone;

[2-(3,5-Bis-trifluoromethyl-phenyl)-piperidin-1-yl]-[2-(S)-(4-fluoro-2-methyl-phenyl)-piperazin-1-yl]-methanone;

2-(4-Fluoro-2-methyl-phenyl)-piperazine-1-carboxylic acid [1-(3,5-bis-trifluoromethyl-phenyl)-but-3-enyl]-methyl-amide;

2-(4-Fluoro-2-methyl-phenyl)-piperazine-1-carboxylic acid [1-(3,5-bis-trifluoromethyl-phenyl)-2-methyl-propyl]-methyl-amide;

2-(4-Fluoro-2-methyl-phenyl)-piperazine-1-carboxylic acid [(3,5-bis-trifluoromethyl-phenyl)-cyclopropyl-methyl]-methyl-amide; and enantiomers, pharmaceutically acceptable salts (e.g hydrochloride, methansulphonate, acetate) and solvates thereof.

Particularly preferred compounds according to the invention are:

2-(S)-(4-Fluoro-2-methyl-phenyl)-4-(piperidine-4-carbonyl)-piperazine-1carboxylic acid (3,5-bis-trifluoromethyl-benzyl)-methyl-amide hydrochloride;

[2-(3,5-Bis-trifluoromethyl-phenyl)-3,6-dihydro-2H-pyridyn-1-yl]-[2-(S)-(4-fluoro-2-methyl-phenyl)-piperazin-1-yl]-methanone hydrochloride (enantiomer A);

4-(2-Amino-acetyl)-2-(S)-(4-fluoro-2-methyl-phenyl)-piperazine-1-carboxylic acid (3,5-bis-trifluoromethyl-benzyl)-methyl-amide hydrochloride;

2-(S)-(4-Fluoro-2-methyl-phenyl)-piperazine-1-carboxylic acid [1-(R)-(3,5-bis-trifluoromethyl-phenyl)-ethyl]-methyl-amide methansulphonate;

2-(S)-(4-Fluoro-2-methyl-phenyl)-piperazine-1-carboxylic acid [1-(R)-(3,5-bis-trifluoromethyl-phenyl)-ethyl]-methyl-amide acetate; and solvates thereof;

The compounds of the invention are antagonists of tachykinins, including substance P and other neurokinins, both in vitro and in vivo and are thus of use in the treatment of conditions mediated by tachykinins, including substance P and other neurokinins.

$NK_1$-receptor binding affinity has been determined in vitro by the compounds' ability to displace [3H]—substance P (SP) from recombinant human $NK_1$ receptors expressed in Chinese Hamster Ovary (CHO) cell membranes.

CHO cell membranes were prepared by using a modification of the method described by Dam T and Quirion R (Peptides, 7:855–864, 1986). Thus ligand binding was performed in 0.4 ml of 50 mM HEPES, pH 7.4, containing 3 mM $MnCl_2$, 0.02% BSA, 0.5 nM [$^3$H]Substance P (30÷56 Ci/mmol, Amersham), a final membrane concentration of 25 μg of protein/ml, and the test compounds. The incubation proceeded at room temperature for 40 min. Non-specific binding was determined using excess of Substance P (1 μM) and represents about 6% of the total binding.

Compounds of the invention were further characterised in a functional assay for the determination of their inhibitory effect. Human-NK$_1$-CHO cells were stimulated with Substance P and the receptor activation was evaluated by measuring the accumulation of cytidinediphosphodiacylglycerol (CDP-DAG), which is the liponucleotide precursor of phosphatidylinositol diphosphate. CDP-DAG accumulates in the presence of Li$^+$ as a consequence of the receptor mediated activation of phospholipase C (PLC) (Godfrey, Biochem. J., 258:621–624, 1989). The method is described in detail by Ferraguti et al. (Mol. Cell. Neurosci., 5:269–276, 1994).

The action of the compounds of the invention at the NK$_1$ receptor may be determined by using conventional tests. Thus the ability to bind at the NK$_1$ receptor was determined using the gerbil foot tapping model as described by Rupniak & Williams, Eur. J. of Pharmacol., 1994.

Compounds of the invention have also been found to exhibit anxiolytic activity in conventional tests. For example in marmoset human threat test (Costall et al., 1988).

Compounds of the invention may be useful in the treatment of CNS disorders in particular in the treatment or prevention of major depressive disorders including bipolar depression, unipolar depression, single or recurrent major depressive episodes with or without psychotic features, catatonic features, melancholic features, atypical features or postpartum onset, the treatment of anxiety and the treatment of panic disorders. Other mood disorders encompassed within the term major depressive disorders include dysthymic disorder with early or late onset and with or without atypical features, neurotic depression, post traumatic stress disorders and social phobia; dementia of the Alzheimer's type, with early or late onset, with depressed mood; vascular dementia with depressed mood; mood disorders induced by alcohol, amphetamines, cocaine, hallucinogens, inhalants, opioids, phencyclidine, sedatives, hypnotics, anxiolytics and other substances; schizoaffective disorder of the depressed type; and adjustment disorder with depressed mood. Major depressive disorders may also result from a general medical condition including, but not limited to, myocardial infarction, diabetes, miscarriage or abortion, etc.

Compounds of the invention are useful as analgesics. In particular they are useful in the treatment of traumatic pain such as postoperative pain; traumatic avulsion pain such as brachial plexus; chronic pain such as arthritic pain such as occurring in osteo-, rheumatoid or psoriatic arthritis; neuropathic pain such as post-herpetic neuralgia, trigeminal neuralgia, segmental or intercostal neuralgia, fibromyalgia, causalgia, peripheral neuropathy, diabetic neuropathy, chemotherapy-induced neuropathy, AIDS related neuropathy, occipital neuralgia, geniculate neuralgia, glossopharyngeal neuralgia, reflex sympathetic dystrophy, phantom limb pain; various forms of headache such as migraine, acute or chronic tension headache, temporomandibular pain, maxillary sinus pain, cluster headache; odontalgia; cancer pain; pain of visceral origin; gastrointestinal pain; nerve entrapment pain; sport's injury pain; dysmennorrhoea; menstrual pain; meningitis; arachnoiditis; musculoskeletal pain; low back pain e.g. spinal stenosis; prolapsed disc; sciatica; angina; ankylosing spondyolitis; gout; burns; scar pain; itch; and thalamic pain such as post stroke thalamic pain.

Compounds of the invention are also useful in the treatment of sleep disorders including dysomnia, insomnia, sleep apnea, narcolepsy, and circadian ritmic disorders.

Compounds of the invention are also useful in the treatment or prevention of the cognitive disorders. Cognitive disorders include dementia, amnestic disorders and cognitive disorders not otherwise specified.

Furthermore compounds of the invention are also useful as memory and/or cognition enhancers in healthy humans with no cognitive and/or memory deficit.

Compounds of the invention are also useful in the treatment of tolerance to and dependence on a number of substances. For example, they are useful in the treatment of dependence on nicotine, alcohol, caffeine, phencyclidine (phencyclidine like compounds), or in the treatment of tolerance to and dependence on opiates (e.g cannabis, heroin, morphine) or benzodiazepines; in the treatment of cocaine, sedative ipnotic, amphetamine or amphetamine-related drugs (e.g dextroamphetamine, methylamphetamine) addiction or a combination thereof.

Compounds of the invention are also useful as anti-inflammatory agents. In particular they are useful in the treatment of inflammation in asthma, influenza, chronic bronchitis and rheumatoid arthritis; in the treatment of inflammatory diseases of the gastrointestinal tract such as Crohn's disease, ulcerative colitis, inflammatory bowel disease and non-steroidal anti-inflammatory drug induced damage; inflammatory diseases of the skin such as herpes and eczema; inflammatory diseases of the bladder such as cystitis and urge incontinence; and eye and dental inflammation.

Compounds of the invention are also useful in the treatment of allergic disorders, in particular allergic disorders of the skin such as urticaria, and allergic disorders of the airways such as rhinitis.

Compounds of the invention are also useful in the treatment of emesis, i.e. nausea, retching and vomiting. Emesis includes acute emesis, delayed emesis and anticipatory emesis. The compounds of the invention are useful in the treatment of emesis however induced. For example, emesis may be induced by drugs such as cancer chemotherapeutic agents such as alkylating agents, e.g. cyclophosphamide, carmustine, lomustine and chlorambucil; cytotoxic antibiotics, e.g. dactnomycin, doxorubicin, mitomycin-C and bleomycin; anti-metabolites, e.g. cytarabine, methotrexate and 5-fluorouracil; vinca alkaloids, e.g. etoposide, vinblastine and vincristine; and others such as cisplatin, dacarbazine, procarbazine and hydroxyurea; and combinations thereof; radiation sickness; radiation therapy, e.g. irradiation of the thorax or abdomen, such as in the treatment of cancer; poisons; toxins such as toxins caused by metabolic disorders or by infection, e.g. gastritis, or released during bacterial or viral gastrointestinal infection; pregnancy; vestibular disorders, such as motion sickness, vertigo, dizziness and Meniere's disease; post-operative sickness; gastrointestinal obstruction; reduced gastrointestinal motility; visceral pain, e.g. myocardial infarction or peritonitis; migraine; increased intercranial pressure; decreased intercranial pressure (e.g. altitude sickness); opioid analgesics, such as morphine; and gastro-oesophageal reflux disease, acid indigestion, over-indulgence of food or drink, acid stomach, sour stomach, waterbrash/regurgitation, heartburn, such as episodic heartburn, nocturnal heartburn, and meal-induced heartburn and dyspepsia.

Compounds of the invention are also useful in the treatment of gastrointestinal disorders such as irritable bowel syndrome; skin disorders such as psoriasis, pruritis and sunburn; vasospastic diseases such as angina, vascular headache and Reynaud's disease; cerebral ischeamia such as cerebral vasospasm following subarachnoid haemorrhage; fibrosing and collagen diseases such as scleroderma and eosinophilic fascioliasis; disorders related to immune enhancement or suppression such as systemic lupus erythematosus and rheumatic diseases such as fibrositis; and cough.

Compounds of the invention are of particular use in the treatment of depressive states, in the treatment of anxiety and of panic disorders. Depressive states include major depressive disorders including bipolar depression, unipolar depression, single or recurrent major depressive episodes with or without psychotic features, catatonic features, melancholic features, atypical features or postpartum onset, dysthymic disorder with early or late onset and with or without atypical features, neurotic depression and social phobia; dementia of the Alzheimer's type, with early or late onset, with depressed mood; vascular dementia with depressed mood; mood disorders induced by alcohol, amphetamines, cocaine, hallucinogens, inhalants, opioids, phencyclidine, sedatives, hypnotics, anxiolytics and other substances; schizoaffective disorder of the depressed type.

Compounds of the invention may be administered in combination with other active substances such as 5HT3 antagonists, serotonin agonists, selective serotonin reuptake inhibitors (SSRI), noradrenaline re-uptake inhibitors (SNRI), tricyclic antidepressants or dopaminergic antidepressants.

Suitable 5HT3 antagonists which may be used in combination of the compounds of the inventions include for example ondansetron, granisetron, metoclopramide.

Suitable serotonin agonists which may be used in combination with the compounds of the invention include sumatriptan, rauwolscine, yohimbine, metoclopramide.

Suitable SSRI which may be used in combination with the compounds of the invention include fluoxetine, citalopram, femoxetine, fluvoxamine, paroxetine, indalpine, sertraline, zimeldine.

Suitable SNRI which may be used in combination with the compounds of the invention include venlafaxine and reboxetine.

Suitable tricyclic antidepressants which may be used in combination with a compound of the invention include imipramine, amitriptiline, chlomipramine and nortriptiline.

Suitable dopaminergic antidepressants which may be used in combination with a compound of the invention include bupropion and aminaptine.

It will be appreciated that the compounds of the combination or composition may be administered simultaneously (either in the same or different pharmaceutical formulations) or sequentially.

The invention therefore provides a compound of formula (I) or a pharmaceutically acceptable salt or solvate thereof for use in therapy, in particular in human medicine.

There is also provided as a further aspect of the invention the use of a compound of formula (I) or a pharmaceutically acceptable salt or solvate thereof in the preparation of a medicament for use in the treatment of conditions mediated by tachykinins, including substance P and other neurokinins.

In an alternative or further aspect there is provided a method for the treatment of a mammal, including man, in particular in the treatment of conditions mediated by tachykinins, including substance P and other neurokinins, comprising administration of an effective amount of a compound of formula (I) or a pharmaceutically acceptable salt thereof.

It will be appreciated that reference to treatment is intended to include prophylaxis as well as the alleviation of established symptoms. Compounds of formula (I) may be administered as the raw chemical but the active ingredient is preferably presented as a pharmaceutical formulation.

Accordingly, the invention also provides a pharmaceutical composition which comprises at least one compound of formula (I) or a pharmaceutically acceptable salt thereof and formulated for administration by any convenient route. Such compositions are preferably in a form adapted for use in medicine, in particular human medicine, and can conveniently be formulated in a conventional manner using one or more pharmaceutically acceptable carriers or excipients.

Thus compounds of formula (I) may be formulated for oral, buccal, parenteral, topical (including ophthalmic and nasal), depot or rectal administration or in a form suitable for administration by inhalation or insufflation (either through the mouth or nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the composition may take the form of tablets or formulated in conventional manner.

The compounds of the invention may be formulated for parenteral administration by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of the invention may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilised components.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

The compounds of the invention may also be formulated in rectal compositions such as suppositories or retention enemas, e.g. containing conventional suppository bases such as cocoa butter or other glycerides.

The compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds of the invention may be formulated as solutions for administration via a suitable metered or unitary dose device or alternatively as a powder mix with a suitable carrier for administration using a suitable delivery device.

A proposed dose of the compounds of the invention is 1 to about 1000 mg per day. It will be appreciated that it may be necessary to make routine variations to the dosage, depending on the age and condition of the patient and the precise dosage will be ultimately at the discretion of the attendant physician or veterinarian. The dosage will also depend on the route of administration and the particular compound selected. Thus for parenteral administration a daily dose will typically be in the range of 1 to about 100 mg, preferably 1 to 80 mg per day. For oral administration a daily dose will typically be within the range 1 to 300 mg e.g 1 to 100 mg.

Compounds of formula (I), and salts and solvates thereof, may be prepared by the general methods outlined hereinafter. In the following description, the groups R, $R_1$, $R_2$, $R_4$, $R_5$, $R_6$, $R_7$, $R_8$, $R_9$, $R_{10}$, m, n, p, q and r have the meaning as previously defined for compounds of formula (I) unless otherwise stated.

According to general process (A), a compound of formula (I) Wherein $R_4$ is hydrogen or a $(CH_2)qR_7$ group as defined in formula (I), provided that when $R_5$ is a $C_{1-4}$ alkyl or a $COR_6$ group, $R_5$ is not in 3 position of the piperazine ring, may be prepared by reduction of a ketopiperazine of formula (II), wherein $R_{4a}$ is hydrogen or a suitable nitrogen protecting group or $R_{4a}$ is a $(CH_2)qR_7$ group or protecting derivatives thereof followed where necessary or desired by removal of any protecting group.

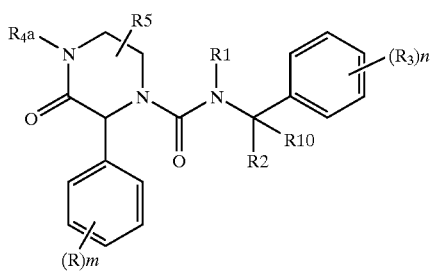
(II)

The reaction may be carried out using a suitable metal reducing agent such as a metal hydride, for example a borane hydride, or a metal hydride complex like lithium aluminum hydride, borohydride, or an organo-metallic complex such as borane-methyl sulphide, 9-borabicyclononane (9-BBN), triethylsilane, sodium triacetoxyborohydride, sodium cyanoborohydride. Alternatively boranes may be produced in situ by reacting Sodium Borohydride in the presence of Iodine, an inorganic acid (e.g. sulphoric acid) or an organic acid such as formic acid, trifluoroacetic, acetic acid, or methansulphonic acid Suitable solvents for this reaction are ether (e.g tetrahydrofuran), or halohydrocarbon (e.g. dichloromethane) or an amide (e.g. N,N-dimethylformamide) at a temperature within the range of room temperature to the reflux temperature of the reaction mixture.

Compounds of formula (II) may be prepared by treating compounds of formula (III) wherein $R_{4a}$ and $R_5$ have the meaning defined in formula (II)

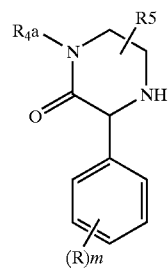
(III)

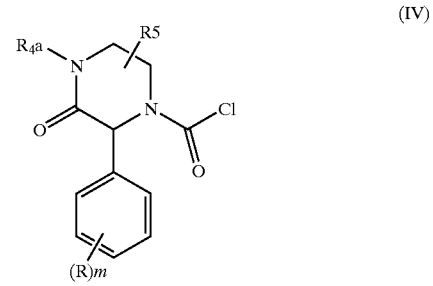
(IV)

with triphosgene in aprotic solvent such as dichloromethane and in the presence of an organic base such triethylamine to form the intermediate carbonyl chloride compound (IV) which may be isolated if required, followed by reaction of compound (IV) with the amine compound (V)

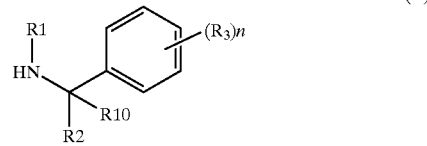
(V)

The reaction conveniently takes place in an aprotic solvent such as a hydrocarbon, a halohydrocarbon such as dichloromethane or an ether such as tetrahydrofuran optionally in the presence of a base such as a tertiary amine e.g. diisopropyl ethyl amine.

Compounds of formula (III) may be prepared by reduction of a dihydropyrazin-2-one (VI) using a suitable metal reducing agent such as sodium borohydride. Alternatively, catalytic hydrogenation may be used, for example using Palladium on Carbon catalyst in a suitable solvent such as methanol.

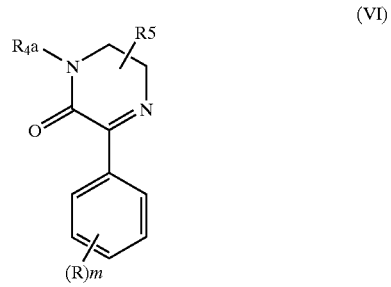
(VI)

Alternatively compounds of formula (III) wherein $R_5$ is hydrogen may be prepared by reaction of compounds of formula (VII), wherein $R_{11}$ is a $C_{1-4}$ alkyl group and X is a suitable leaving group such as halogen, i.e. bromine or iodine atom, or $OSO_2CF_3$,

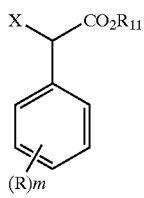

(VII)

with ethylendiamine. The reaction conveniently takes place in a suitable solvent such as alcohol (i.e. ethanol) at an elevated temperature.

According to a further general process (B) a compound of formula (I) wherein $R_4$ is hydrogen or $(CH_2)rCO(CH_2)p\ R_7$ as above defined may be prepared by reacting a compound of formula (VIII)

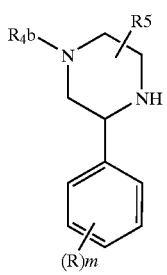

(VIII)

wherein $R_{4b}$ represents a nitrogen protecting group or $R_{4b}$ is $(CH_2)r\ CO(CH_2)pR_7$ or a protecting group thereof, with triphosgene in an aprotic solvent such as dichloromethane or alkyl esters (e.g. ethylacetate) and in the presence of an organic base such triethylamine to form the intermediate carbonyl chloride compound (IVa) which may be isolated if required, followed by reaction of compound (IV) with the amine compound (V)

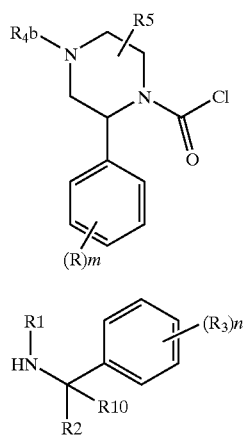

(IVa)

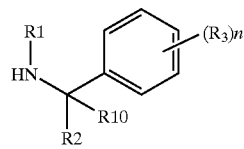

(V)

The reaction conveniently takes place in an aprotic solvent such as a hydrocarbon, a halohydrocarbon such as dichloromethane or an ether such as tetrahydrofuran or alkyl esters (i.e ethylacetate) optionally in the presence of a base such as a tertiary amine e.g. diisopropyl ethyl amine or triethylamine followed by deprotection where necessary.

When $R_{4a}$ or $R_{4b}$ is a nitrogen protecting group, examples of suitable groups include alkoxycarbonyl e.g. t-butoxycarbonyl, benzyloxycarbonyl, arylsulphonyl e.g. phenysulphonyl or 2-trimethylsilylethoxymethyl.

Protection and deprotection may be effected using conventional techniques such as those described in "Protective Groups in Organic Synthesis $2^{nd}$ Ed." by T. W. Greene and P. G. M. Wuts (John Wiley and Sons, 1991) and as described in the examples hereinafter.

Compounds of formula (I) wherein $R_4$ is a $CO(CH_2)pR_7$ group or protective derivatives thereof may be also prepared by reaction of the compound of formula (I)

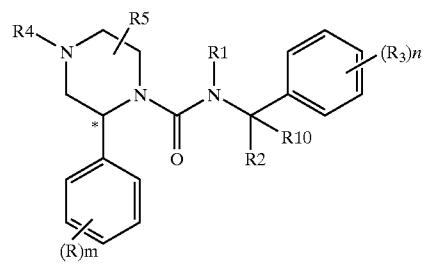

(I)

wherein $R_4$ is a hydrogen atom, with an activated derivative of the acid $R_7(CH_2)pCO_2H$(IX).

The activated derivatives of the carboxylic acid (IX) may be prepared by conventional means. Suitable activated derivatives of the carboxylic group include the corresponding acyl halide, mixed anhydride, activated ester such as thioester or the derivative formed between the carboxylic acid group and a coupling agent such as that used in peptide chemistry, for example carbonyl diimidazole or a diimide such as 1-(3-dimethylaminopropyl)-3-ethylcarbodiimide. The reaction is preferably carried out in an aprotic solvent such as an amide e.g. N,N-dimethylformamide or acetonitrile.

Compounds of formula (I) wherein $R_4$ is $CONR_9R_8$ in which $R_9$ or $R_8$ have the meaning defined in formula (I) may be prepared by reaction of a compound of formula (I) wherein $R_4$ is a hydrogen atom with triphosgene in an aprotic solvent such as dichloromethane and in the presence of an organic base such as triethylamine followed by reaction with the amine compound $NR_9R_8(X)$.

Alternatively compounds of formula (I) wherein $R_4$ is a $CONHR_9$ group in which $R_9$ is $C_{1-4}$ alkyl may be also prepared by reaction with isocyanate of formula $R_9NC=O$ (XI). The reaction with the compound (XI) is conveniently carried out in a solvent such as tetrahydrofuran or aqueous tetrahydrofuran, a halohydrocarbon (e.g. dichloromethane) or acetonitrile optionally in the presence of a base such as triethylamine and at temperature within the range 0–80° C.

In a further embodiment compounds of formula (I) wherein $R_4$ is $(CH_2)qR_7$ or $R_4$ is $(CH_2)rCO(CH_2)pR_7$ wherein q, r and $R_7$ have the meanings defined in formula (I) or are protective derivatives thereof with the provision that r is not zero, may also be prepared by reaction of compounds of formula (I) wherein $R_4$ is a hydrogen group with a compound of formula (XII) $R_7(CH_2)qX$ or $X(CH_2)rCO(CH_2)pR_7$ (XIII), in which X is a leaving group such as halogen e.g. chlorine, a bromine atom, a mesyl or a tosyl group.

In a further preferred embodiment compounds of formula (I) wherein $R_4$ is $(CH_2)qR_7$ wherein q and $R_7$ have the meanings defined in formula (I) or are protective derivatives thereof may be also prepared by reaction of compounds of formula (I) wherein $R_4$ is a hydrogen group with a compound of formula (XIV) $R_7(CH_2)qCHO$ (XIV), in which q is zero or an integer from 1 to 3 and $R_7$ has the meanings defined in formula (I) or are protective derivatives thereof, in the presence of suitable metal reducing agent such as NaCNBH$_3$.

In a further preferred embodiment compounds of formula (I) wherein R$_1$ and R$_2$ together with nitrogen and carbon atom to which they are attached respectively represent a 5 to 6 unsaturated membered heterocyclic group may be prepared by ring closing metathesis reaction (RCM) of compounds of formula (XV).

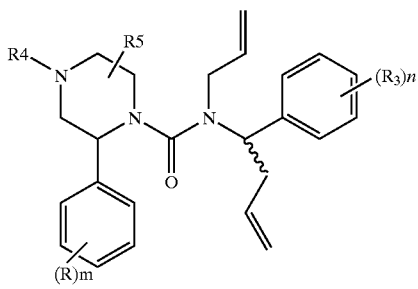

catalysed by a transition metal complex such as a ruthenium alkylidene complex (i.e benzylidene bis (tricyclohexylphosphine)dichlororuthenium). The reaction is conveniently carried out in an aprotic solvent such dichloromethane at 0° C.

Compounds of formula (XV) may be prepared from the appropriate intermediate using any of the processes described herein for preparing compounds of formula (I).

Compound of formula (I) wherein R$_1$ and R$_2$ together with nitrogen and carbon atom to which they are attached respectively represent a 5 to 6 saturated membered heterocyclic group may be prepared by reduction of the corresponding 5 to 6 unsatuared membered heterocyclic group with suitable reducing agent such as catalytic hydrogenation in a suitable solvent such as methanol at room temperature.

Where it is desired to isolate a compound of formula (I) as a salt, for example a pharmaceutically acceptable salt, this may be achieved by reacting the compound of formula (I) in the form of the free base with an appropriate amount of suitable acid and in a suitable solvent such as an alcohol (e.g. ethanol or methanol), an ester (e.g. ethyl acetate) or an ether (e.g. diethyl ether tertbutylmethyl ether or tetrahydrofuran).

Compounds of formula (V), (VI), (VIII), (IX), (X) (XII), (XIII) or (XIV) may be prepared by analogous methods to those used for known compounds.

Thus for example compounds of formula (VIII) may be obtained by reduction of a compound of formula (III).

The reaction may be carried out using a suitable metal reducing agent such as a metal hydride, for example a borane hydride, or a metal hydride complex like lithium aluminum hydride, borohydride, or an organo-metallic complex such as borane-methyl sulphide, 9-borabicyclononane (9-BBN), triethylsilane, sodium triacetoxyborohydride, sodium cyanoborohydride.

Alternatively boranes may be produced in situ by reacting Sodium Borohydride in the presence of Iodine, an inorganic acid (e.g. sulphoric) or an organic acid such as formic acid, trifluoroacetic, acetic acid, methansuphonic acid Pharmaceutically acceptable salts may also be prepared from other salts, including other pharmaceutically acceptable salts, of the compound of formula (I) using conventional methods.

The compounds of formula (I) may readily be isolated in association with solvent molecules by crystallisation from or evaporation of an appropriate solvent to give the corresponding solvates.

When a specific enantiomer of a compound of general formula (I) is required, this may be obtained for example by resolution of a corresponding enantiomeric mixture of a compound of formula (I) using conventional methods.

Thus specific enantiomers of the compounds of formula (I) in which R$_4$ is a hydrogen atom may be prepared by reaction of a suitable chiral alcohol, in the presence of a source of a carbonyl group (such as triphosgene or carbonyl diimidazole) separating the resulting diastereoisomeric carbamates by conventional means e.g. chromatography or by fractional crystallisation. The required enantiomer of a compound of general formula (I) may be isolated by removal of carbamate and conversion into the required free base or salts thereof.

Suitable chiral alcohol for use in the process include (R)-sec-phenylethyl alcohol, etc.

Alternatively, enantiomers of a compound of general formula (I) may be synthesised from the appropriate optically active intermediates using any of the general processes described herein.

Thus for example the required enantiomer may be prepared by the corresponding enantiomeric amine of formula (III) using any of the processes described above for preparing compounds of formula (I) from the amine (III). The enantiomer of amine (III) may be prepared from the racemic amine (III) using conventional procedures such as salt formation with a suitable optically active acid such as L(+)mandelic acid or (1S)-(+)-10-camphorsulfonic acid In one preferred embodiment of the invention the specific enantiomer of amine (IIIa)

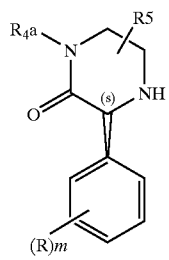

may be prepared by dynamic kinetic resolution of amine(III) with a suitable optically active acid such as L(+)mandelic acid or (1S)-(+)-10-camphorsulfonic acid in the presence of aromatic aldehyde such as 3,5 dichlorosalicylaldhyde, salicylaldhyde, benzaldehyde-p-nitro benzaldehyde.

A particular preferred aldehyde for use in this reaction is 3,5 dichlorosalicylaldhyde. The reaction is conveniently carried out in an aprotic solvent such as tetrahydrofuran, ethyl actetate at a temperature ranging between 20–60° C.

The invention is further illustrated by the following Intermediates and Examples which are not intended as a limitation of the invention.

In the Intermediates and Examples unless otherwise stated:

Melting points (m.p.) were determined on a Gallenkamp m.p. apparatus and are uncorrected. All temperatures refers to ° C. Infrared spectra were measured on a FT-IR instrument. Proton Magnetic Resonance ($^1$H-NMR) spectra were recorded at 400 MHz, chemical shifts are reported in ppm downfield (d) from Me$_4$Si, used as internal standard, and are assigned as singlets (s), doublets (d), doublets of doublets (dd), triplets (t), quartets (q) or multiplets (m). Column chromathography was carried out over silica gel (Merck AG Darnstaadt, Germany). The following abbreviations are used in text: AcOEt=ethyl acetate, CH=cyclohexane, DCM= dichloromethane. Et$_2$O=dietyl ether, DMF=N,N'-dimethylformamide, DIPEA=N,N-diisopropylethylamine MeOH=methanol, TEA=triethylamine, TFA=trifluoroacetic acid, THF=tetrahydrofuran. Tlc refers to thin layer chromatography on silica plates, and dried refers to a solution dried over anhydrous sodium sulphate; r.t. (RT) refers to room temperature.

Enantiomer A or enantiomer B refer to a single enantiomer whose absolute stereochemistry was not characterised.

Diastereoisomer A refers to a mixture of compounds having anti configuration as defined above.

Diastereoisomer B refers to a mixture of compounds having syn configuration as defined above.

Intermediate 1

2-Methyl-4-fluoroboronic acid

To magnesium turnings (0.5 g), heated at 90° C., a solution of commercial 2-bromo-5-fluorotoluene (2 mL) in THF (3 mL) was added drop-wise. The reaction mixture was heated at 90–95° C. for 1½ hr, and then the mixture was diluted with further THF (10 mL) and transferred in a dropping funnel. The latter solution and trimethylborate (2.1 mL) were simultaneously added to stirred Et$_2$O (15 mL), maintaining the temperature below −60° C. The reaction mixture was allowed to warm to r.t., then the stirring was continued for 1½ hr. Water (6 mL) was added and the reaction mixture was stirred overnight. AcOEt was added and the solution was washed with 1N HCl and brine. The organic phase was next dried and concentrated to give the crude product which was triturated in Et$_2$O/petroleum (25 mL/75 mL) to obtain the title compound as a trimer (1.44 g, white powder).

NMR (DMSO) δ (ppm) 7.87 (m, 3H), 6.99–6.93 (m, 6H), 2.6 (s, 9H)

Intermediate 2

2-(4-Fluoro-2-methyl-phenyl)-pyrazine

A mixture of intermediate 1 (1.34 g), 2-chloropyrazine (1 mL) and bis[1,2-bis(diphenylphosphino)ethane]-palladium (0) (0.21 g) in toluene/1M sol. Na$_2$CO$_3$/EtOH95% 20 mL/20 mL/10 mL was heated at reflux for 2 hr. The solution was poured into AcOEt and washed with brine. The organic phase was next dried and concentrated to give the crude product, which was purified by flash chromatography (CH/AcOEt 85:15) to obtain the title compound (1.4 g) as a white powder.

m.p.=66–68° C.

NMR (DMSO) δ (ppm) 8.81 (d, 1H), 8.72 (m, 1H), 8.63 (d, 1H), 7.52 (m, 1H), 7.22 (m, 1H), 7.17 (m, 1H), 2.35 (s, 3H).

Intermediate 3

2-(3-Isopropyl-phenyl)-pyrazine

To a solution of commercial 3-isopropyl-benzene boronic acid (1.0 g) in a 2:2:1 mixture of toluene/1M Na$_2$CO$_3$/EtOH (122 mL), at r.t.,2-chloropyrazine (599 μL) and the bis[1,2-bis(diphenylphosphino)ethane]-palladium(0) catalyst (110 mg) were added. The reaction mixture was heated at 80° C. for 3 hr. It was then cooled down and partitioned between AcOEt/sat.aq. NaCl. The phases were separated and the organic layer was dried. The solids were filtered and the solvent evaporated. The crude oil was purified by flash chromatography (CH/AcOEt 7:3) obtaining the title compound as a clear oil (468 mg).

NMR (CDCl$_3$): δ (ppm) 9.02 (d, 1H), 8.63 (m, 1H), 8.49 (d, 1H), 7.89 (m, 1H), 7.80 (m, 1H), 7.44 (t, 1H), 7.35 (d, 1H), 3.02 (m, 1H), 1.31 (d, 6H).

Intermediate 4

2-(2-Isopropyl-phenyl)-pyrazine

1) To a suspension of magnesium turnings (134 mg) in anh. THF (2.5 mL). at r.t., under N$_2$, a small crystal of I$_2$ was added, followed by 10% of a solution of commercial 1-bromo-2-isopropyl-benzene (1.0 g) in anh. THF (2.6 mL). The suspension was heated gently (heat gun) until the brown colour disappeared. The remaining bromide was added drop-wise, maintaining the reaction mixture warm (50–60° C.) with an oil bath. After the addition was complete (15 min) the suspension was stirred at 60° C. until the magnesium turnings had almost completely reacted (2 hr). The new brown solution was used in the next step.

2) To a solution of the 2-chloropyrazine (448 μL) in anh. THF (5.1 mL), at 0° C., under N$_2$, [1,2-bis(diphenylphosphino)ethane]dichloronickel(II) (100 mg) and the Grignard solution were successively added drop-wise. The brown solution was stirred at r.t. for 30 min, then at reflux for 3 hr. It was then poured in sat.aq. NaCl/DCM and the phases were separated. The aqueous layer was extracted with DCM (2×) and the combined organic extracts were dried. The solids were filtered and the solvent evaporated. The crude oil obtained was purified by flash chromatography (CH/AcOEt 7:3) obtaining the title compound as a yellow oil (676 mg).

NMR (CDCl$_3$): δ (ppm) 8.67 (d, 1H), 8.67 (m, 1H), 8.54 (d, 1H), 7.5–7.3 (m, 4H), 3.13 (m, 1H), 1.20 (d, 6H).

Intermediate 5

2-(4-Fluoro-3-methyl-phenyl)-pyrazine

1) To a suspension of magnesium turnings (167 mg) in anh. THF (2.6 mL), at r.t., under N$_2$, a small crystal of I$_2$ was added, followed by 10% of a solution of commercial 4-bromo-1-fluoro2-methyl-benzene (1.0 g) in anh. THF (2.7 mL). The suspension was heated gently (heat gun) until the brown colour disappeared. The remaining bromide was added drop-wise, maintaining the reaction mixture warm (50–60° C.) with an oil bath. After the addition was complete (15 min) the suspension was stirred at 60° C. until the magnesium turnings had almost completely reacted (2 hr). The new brown solution was used in the next step.

2) To a solution of the 2-chloropyrazine (472 μL) in anh. THF (5.3 mL), at 0° C., under N$_2$, [1,2-bis(diphenylphosphino)ethane]dichloronickel(II) (100 mg) and the Grignard solution were successively added dropwise. The brown solution was stirred at r.t. for 30 min, then at reflux for 3 hr. It was then poured in sat.aq. NaCl/DCM and the phases were separated. The aqueous layer was extracted with DCM (2×) and the combined organic extracts were dried. The solids were filtered and the solvent evaporated. The crude oil obtained was purified by flash chromatography (CH/AcOEt 7:3) to give the title compound as a yellow oil (571 mg).

NMR (CDCl$_3$): δ (ppm) 8.98 (d, 1H), 8.60 (m, 1H), 8.49 (d, 1H), 7.87 (m, 1H), 7.80 (m, 1H), 7.13 (t, 1H), 2.37 (s, 3H).

Intermediate 6

2-(2,4-Difluoro-phenyl)-pyrazine

1) To a suspension of magnesium turnings (139 mg) in anh. THF (2.6 mL), at r.t., under N$_2$, a small crystal of I$_2$ was added, followed by 10% of a solution of commercial 1-bromo-2,4difluoro-benzene (1.0 g) in anh. THF (2.6 mL). The suspension was heated gently (heat gun) until the brown colour disappeared. The remaining bromide was added drop-wise, maintaining the reaction mixture warm (50–60° C.) with an oil bath. After the addition was complete (15 min) the suspension was stirred at 60° C. until the magnesium turnings had almost completely reacted (2 hr). The new brown solution was used in the next step.

2) To a solution of the 2-chloropyrazine (463 µL) in anh. THF (5.2 mL), at 0° C., under $N_2$, [1.2-bis (diphenylphosphino)ethane]dichloronickel(II) (50 mg) and the Grignard solution were successively added drop-wise. The brown solution was stirred at rt. for 30 min, then at reflux for 3 hr. It was then poured in sat.aq. NaCl/DCM and the phases were separated. The aqueous layer was extracted with DCM (2×) and the combined organic extracts were dried. The solids were filtered and the solvent evaporated. The crude oil obtained was purified by flash chromatography (CH/AcOEt 7:3) to give the title compound as a yellow solid (175 mg).

NMR ($CDCl_3$): δ (ppm) 9.01 (dd, 1H), 8.78 (dd, 1H), 8.66 (d, 1H), 7.99 (td, 1H), 7.47 (td, 1H), 7.29 (td, 1H).

Intermediate 7

2-(4-Fluoro-2-methyl-phenyl)-piperazine hydrochloride

A two neck round bottom flask was equipped with a water condenser and a dropping funnel and was flushed with $N_2$. Mg turnings (1.45 g) were introduced in the flask and were suspended in anh. THF (5 mL). A small crystal of $I_2$ was added in order to activate the Mg. The dropping funnel was filled with a solution of the commercial 2-bromo-5-fluorotoluene (10 g) in anh. THF (30 mL). The solution of the bromide was added drop-wise to the Mg turnings and the solution warmed up to approximately 70° C. The solution was kept at that temperature until complete disappearance of the Mg turnings.

Meanwhile, 2-chloropyrazine (4.75 mL) was dissolved in anh. THF (30 mL) and [1,2-bis(diphenylphosphino)ethane] dichloronickel(II) (510 mg) was added. To this suspension the solution of Grignard was added dropwise, at 0° C., under $N_2$. After the addition was complete, the reaction mixture was heated at reflux for 2 hr. The THF was evaporated, the residue poured in sat. aq. NaCl and the aqueous phase was extracted with DCM (3×). The organic extracts were dried, the solids were filtered and the solvent evaporated. The crude oil was purified by flash chromatography (CH/AcOEt 85:15) and then through a small column of Florsil (eluant: DCM) to eliminate the nickel residue (6.0 g): 2-(4-fluoro-2-methyl-phenyl)pyrazine (6.0 g) was obtained as a pale yellow solid.

2-(4-Fluoro-2-methyl-phenyl)pyrazine (0.3 g) dissolved in EtOH 95% (20 mL) and 37% HCl (0.2 mL) was hydrogenated at 5 atm. for 4 hr, in the presence of 20% Pd(OH)$_2$/C (30 mg) as catalyst. The catalyst was filtered off and the solvent was evaporated. The crude residue was triturated in MeOH/AcOEt (5 mL/15 mL) to obtain the title compound (0.08 g) as a white powder.

m.p. >220° C.

NMR (DMSO) δ (ppm) 9.72 (broad, 2H), 7.90 (d, 1H), 7.21–7.17 (m, 2H), 4.85 (m, 1H), 3.57–3.2 (m, 6H), 2.40 (s, 3H).

Intermediate 8

3-(4-Fluoro-2-methyl-phenyl)-piperazine-1-carboxylic acid benzyl ester

To a solution of intermediate 7 (0.25 g) and TEA (0.5 mL) in DCM (15 mL) a solution of benzylchloroformate (0.15 mL) in DCM (10 mL) was added drop-wise, at 0° C. The reaction mixture was stirred at 0° C. for 2 hr, then washed with brine. The organic phase was dried and concentrated to give the crude product, which was purified by flash column chromatography (CH/AcOEt 25:75) to obtain the title compound (0.21 g) as a colourless oil.

NMR ($CDCl_3$, 40° C.) δ (ppm) 7.52 (m, 1H), 7.4–7.3 (m, 5H), 6.9–6.8 (m, 2H), 5.16 (dd, 2H), 4.12 (m, 2H), 3.86 (m, 1H), 3.3–2.7 (m, 4H), 2.33, (bs, 3H).

Intermediate 9

3-(3-Isopropyl-phenyl)-piperazine-1-carboxylic acid benzyl ester

To a solution of intermediate 3 (428 mg) in anh. EtOH (47 mL), at r.t., under $N_2$, conc. HCl (492 µL) and Pd(OH)$_2$/C 20% (86 mg, 20% wt) were added. The black suspension was placed in a PARR apparatus and the hydrogenation was done at r.t. under 7 atm of $H_2$ for 18 hr. The catalyst was then filtered on Celite and the Celite cake rinsed with MeOH. The filtrate was evaporated to dryness. The grey solid 2-(3-Isopropyl-phenyl)piperazine hydrochloride (654 mg) was dissolved in anh. DCM (24 mL), at 0° C., under $N_2$, then TEA (1.32 mL) and benzylchloroformate (404 µL) were added. The solution was stirred at 0° C. for 2½ hr. It was then poured in DCM/sat.aq. NaCl/sat.aq. $K_2CO_3$ and the phases were separated. The aqueous layer was extracted with DCM (1×) and the combined organic extracts were dried. The solids were filtered and the solvent evaporated. The crude oil was purified by flash chromatography (CH/AcOEt 6:4) to give the title compound as a yellow oil (192 mg).

NMR ($CDCl_3$): δ (ppm) 7.34–7.12 (m, 8H), 5.08 (m, 2H), 3.89 (bd, 1H), 3.85 (bm, 1H), 3.55 (bd, 1H), 3.0–2.65 (bm, 6H), 1.17 (d, 6H).

Intermediate 10

3-(2-Isopropyl-phenyl)-piperazine-1-carboxylic acid benzyl ester

To a solution of intermediate 4 (315 mg) in anh. EtOH (40 mL), at r.t., under $N_2$, conc. HCl (529 µL) and Pd(OH)$_2$/C 20% (63 mg, 20% wt) were added. The black suspension was placed in a PARR apparatus and the hydrogenation was done at r.t. under 7 atm of $H_2$ for 18 hr. The catalyst was then filtered on Celite and the Celite cake rinsed with MeOH. The filtrate was evaporated to dryness. The grey solid 2-(2-Isopropyl-phenyl)-piperazine hydrochloride (411 mg) was dissolved in anh. DCM (16 mL), at 0° C., under $N_2$, then TEA (886 µL) and benzylchloroformate (272 µL) were added. The solution was stirred at 0° C. for 2.5 hr. It was then poured in DCM/sat.aq. NaCl/sat.aq. $K_2CO_3$ and the phases were separated. The aqueous layer was extracted with DCM (1×) and the combined organic extracts were dried. The solids were filtered and the solvent evaporated. The crude oil was purified by flash chromatography (CH/AcOEt 6:4) obtaining the title compound as a yellow oil (117 mg).

NMR ($CDCl_3$): δ (ppm) 7.52 (d, 1H), 7.4–7.3 (m, 5H), 7.26 (d, 1H), 7.21 (t, 1H), 7.14 (t, 1H), 5.14 (d, 1H), 5.03 (d, 1H), 4.0–3.8 (m, 3H), 3.23 (m, 1H), 2.99 (m 1H), 2.91 (m, 1H), 2.8–2.0 (m, 2H), 1.19 (d, 6H).

Intermediate 11

3-(4-Fluoro-3-methyl-phenyl)-piperazine-1-carboxylic acid benzyl ester

To a solution of intermediate 5 (314 mg) in anh. EtOH (30 mL), at r.t., under $N_2$, conc. HCl (350 µL) and Pd(OH)$_2$/C 20% (30 mg, 10% wt) were added. The black suspension was placed in a PARR apparatus and the hydrogenation was done at r.t. under 7 atm of $H_2$ for 18 hr. The catalyst was then filtered on Celite and the Celite cake rinsed with MeOH. The filtrate was evaporated to dryness. The grey solid 2-(4-Fluoro-3-methyl-phenyl)-piperazine hydrochloride (411 mg) was dissolved in anh. DCM (15 mL), at 0° C., under $N_2$, then TEA (858 μL) and benzylchloroformate (264 μL) were added. The solution wag stirred at 0° C. for 2.5 hr. It was then poured in DCM/sat.aq. NaCl/sat.aq. $K_2CO_3$ and the phases were separated. The aqueous layer was extracted with DCM (1×) and the combined organic extracts were dried. The solids were filtered and the solvent evaporated. The crude oil was purified by flash chromatography (CH/AcOEt 6:4) obtaining the title compound as a yellow oil (170 mg).

NMR (CDCl$_3$): δ (ppm) 7.3–7.4 (m, 5H), 7.23 (m, 1H), 7.17 (m, 1H), 6.96 (t, 1H), 5.17 (m, 2H), 4.15 (m, 2H), 3.67 (m, 1H), 2.7–3.2 (m, 4H), 2.27 (s, 3H).

Intermediate 12

3-(2,4-Difluoro-phenyl)-piperazine-1-carboxylic acid benzyl ester

To a solution of intermediate 6 (175 mg) in anh. EtOH (30 mL), at r.t., under $N_2$, conc. HCl (228 μL, 2.5 eq) and Pd(OH)$_2$/C 20% (20 mg, 10% wt) were added. The black suspension was placed in a PARR apparatus and the hydrogenation was done at r.t. under 7 atm of $H_2$ for 18 hr. The catalyst was then filtered on Celite and the Celite cake rinsed with MeOH. The filtrate was evaporated to dryness. The greenish solid 2-(2,4-Difluoro-phenyl)-piperazine hydrochloride (247 mg) was dissolved in anh. DCM (9.1 mL), at 0° C., under $N_2$, then TEA (508 μL) and benzylchloroformate (162 μL) were added. The solution was stirred at 0° C. for 3 hr. It was then poured in DCM/sat.aq. NaCl/sat.aq. $K_2CO_3$ and the phases were separated. The aqueous layer was extracted with DCM (1×), and the combined organic extracts were dried. The solids were filtered and the solvent evaporated. The crude oil was purified by flash chromatography (CH/AcOEt 6:4) obtaining the title compound as a yellow oil (100 mg).

NMR (CDCl$_3$): δ (ppm) 7.49 (m, 1H), 7.3–7.4 (m, 5H), 6.76–6.8 (m, 2H), 5.16 (s, 2H), 4.15 (m, 2H), 4.03 (m,$_1$H), 2.8–3.15 (m, 4H).

Intermediate 13

4-[(3,5-Bis-trifluoromethyl-benzyl)-methyl-carbamoyl]-3-(4-fluoro-2-methyl-phenyl)-piperazine-1-carboxylic acid benzyl ester A solution of triphosgene (0.02 mL) in DCM (10 mL) was added drop-wise to a solution of intermediate 8 (0.05 g) and TEA (0.15 mL) in DCM (10 mL) at 0° C. The reaction mixture was allowed to warm to r.t. in 3 hr, then DIPEA (0.07 mL) and (3,5-bis-trifluoromethyl-benzyl)-methyl-amine hydrochloride (53 mg) were added. The reaction mixture was stirred at reflux for 2 hr and at r.t. overnight, then was washed with a 1N solution of HCl and brine. The organic phase was dried and concentrated to give the crude product, which was purified by flash chromatography (CH/AcOEt 7:3) to obtain the title compound (0.05 g) as a colourless oil.

NMR (CDCl$_3$) δ (ppm) 7.76 (s, 1H), 7.49 (s, 2H), 7.4–7.3 (m, 5H), 7.20 (dd, 1H), 6.86 (d, 1H), 6.79 (m, 1H), 5.17 (s, 2H), 4.66 (d, 1H), 4.64 (m, 1H), 4.36 (d, 1H), 3.97 (m, 2H), 3.4 (m, 2H), 3.16 (m, 2H), 2.93 (s, 3H), 2.38 (bs, 3H)

Intermediate 14

4-[(3,5-Bis-trifluoromethyl-benzyl)-methyl-carbamoyl]-3-(3-isopropyl-phenyl)piperazine-1-carboxylic acid benzyl ester To a solution of intermediate 9 (192 mg) in anh. DCM (7 mL), at 0° C., under $N_2$, TEA (237 μL) was added. Then, a solution of triphosgene (76 mg) in anh. DCM (4 mL) was added drop-wise. The reaction was stirred at 0° C. for 2 hr.

To this solution DIPEA (198 μL) and (3,5-bis-trifluoromethyl-benzyl)-methyl-amine hydrochloride (200 mg) were added. The solution was stirred at r.t. for 18 hr. The reaction mixture was diluted with DCM, washed with 10% citric acid (1×) and dried. The solids were filtered and the solvent evaporated. The crude oil was purified by flash chromatography (CH/AcOEt 65:35) to give the title compound as a thick oil (353 mg).

NMR (CDCl$_3$): δ (ppm) 7.91 (bs, 1H), 7.84 (bs 2H), 7.36–7.26 (m, 5H), 7.18–7.10 (m, 2H), 7.06 (m, 2H), 5.07 (s, 2H), 4.76 (t, 1H), 4.50 (bs, 2H), 3.96 (dd, 1H), 3.66 (td, 1H), 3.57 (dd, 1H), 3.4–3.3 (m, 2H), 3.19 (m, 1H), 2.86 (s, 3H), 2.76 (m, 1H), 1.09 (2d, 6H).

Intermediate 15

4-[(3,5-Bis-trifluoromethyl-benzyl)-methyl-carbamoyl]-3-(2-isopropyl-phenyl)-piperazine-1-carboxylic acid benzyl ester To a solution of intermediate 10 (46 mg) in anh. DCM (3.9 mL), at 0° C., under $N_2$, TEA (145 μL) was added, then a solution of triphosgene (46 mg) in anh. DCM (3 mL) was added drop-wise. The reaction was stirred at 0° C. for 2 hr.

To this solution, DIPEA (121 μL) and (3,5-bis-trifluoromethyl-benzyl)-methyl-amine hydrochloride (122 mg) were added. The solution was stirred at r.t. for 18 hr. The reaction mixture was diluted with DCM, washed with 10% citric acid (1×) and dried. The solids were filtered and the solvent evaporated. The crude oil was purified by flash chromatography (CH/AcOEt 7:3) to give the title compound as a clear oil (108 mg).

NMR (CDCl$_3$): δ (ppm) 7.89 (bs, 1H), 7.71 (bs, 2H), 7.38–7.28 (m, 5H), 7.28 (dd, 1H), 7.23 (dd, 1H), 7.16 (dt, 1H), 7.01 (dt, 1H), 5.14 (d, 1H), 5.05 (bd, 1H), 4.68 (dd, 1H), 4.52 (2d(AB), 2H), 3.83 (dd, 1H), 3.71 (dt, 1H), 3.53 (md, 1H), 3.41 (dt, 1H), 3.26 (m, 1H), 3.15–3.05 (m, 2H), 1.19 (d, 3H), 1.13 (m, 3H).

Intermediate 16

4-[(3,5-Bis-trifluoromethyl-benzyl)-methyl-carbamoyl]-3-(4-fluoro-3-methyl-phenyl)-piperazine-1-carboxylic acid benzyl ester To a solution of intermediate 11 (170 mg) in anh. DCM (7 mL), at 0° C., under $N_2$, TEA (217 μL) was added. Then, a solution of triphosgene (69 mg) in anh. DCM (3 mL) was added drop-wise. The reaction was stirred at 0° C. for 2 hr.

To this solution DIPEA (181 μL) and (3,5-bis-trifluoromethyl-benzyl)-methyl-amine hydrochloride (183 mg) were added. The solution was stirred at r.t. for 18 hr. The reaction mixture was diluted with DCM, washed with 10% citric acid (1×) and dried. The solids were filtered and the solvent evaporated. The crude oil was purified by flash chromatography (CH/AcOEt 65:35) to give the title compound as a gummy solid (226 mg).

NMR (CDCl$_3$): δ (ppm) 7.77 (m, 1H), 7.60 (m, 2H), 7.3–7.4 (m, 5H), 7.05–7.15 (m, 2H), 6.90 (m, 1H), 5.14 (m, 2H), 4.64.8 (m, 1H), 4.54+4.47 (AB, 2H), 3.82 (bm, 1H), 3.73 (dd, 1H), 3.65 (m, 1H), 3.57 (m, 1H), 3.33 (m, 1H), 3.26 (m, 1H), 2.90 (s, 3H), 2.19 (s, 3H).

Intermediate 17

4-[(3,5-Bis-trifluoromethyl-benzyl)-methyl-carbamoyl]-3-(2,4-difluoro-phenyl)-piperazine-1-carboxylic acid benzyl ester To a solution of intermediate 12 (95 mg) in anh. DCM (3 mL), at 0° C., under $N_2$, TEA (120 μL) was added. Then a solution of triphosgene (38 mg) in anh. DCM (3 mL) was added dropwise. The reaction was stirred at 0° C. for 2 hr.

To this solution DIPEA (100 μL, 2 eq) and (3,5-bis-trifluoromethyl-benzyl)-methyl-amine hydrochloride (101 mg) were added. The solution was stirred at r.t. for 18 hr. The reaction mixture was diluted with DCM, washed with 10% citric acid (1×) and dried. The solids were filtered and the solvent evaporated. The crude oil was purified by flash chromatography (CH/AcOEt 7:3) to give the title compound as a yellow gum (134 mg).

NMR (CDCl$_3$): δ (ppm) 7.76 (s, 1H), 7.56 (s, 2H), 7.26–7.40 (m, 6H), 6.76 (m, 2H), 5.17 (m, 2H), 4.83 (m, 1H), 4.36–4.60 (dd+m, 2H), 3.90 (m, 1H), 3.25–3.7 (m, 2H), 2.86 (s, 3H).

Intermediate 18

4-(3,5-Bis-trifluoromethyl-benzyl-carbamoyl)-3-(4-fluoro-2-methyl-phenyl)-piperazine-1-carboxylic acid benzyl ester To a solution of intermediate 8 (0.15 g) and TEA (0.32 ml) in DCM (35 ml), a solution of triphosgene (0.065 ml) in DCM (25 ml) was added drop-wise at 0° C. The reaction mixture was allowed to warm to r.t. in 3 hr, then pyridine (0.3 mL) and 3,5-bis(trifluoromethyl)-benzyl-1-methyl-amine hydrochloride (53 mg) were added. The reaction mixture was stirred at r.t. overnight, then washed with a 1N solution of HCl and brine. The organic phase was next dried and concentrated to give the crude product which was purified by flash chromatography (CH/AcOEt 7:3) to obtain the title compound (0.086 g) as a pale yellow oil and 4-benzyloxycarbonyl-2-(4-fluoro-2-methyl-phenyl)-piperazine-1-carbonyl chloride (0.075 g).

Title compound: NMR (CDCl$_3$) δ (ppm) 0.78–7.7 (m, 1H), 7.5–7.4 (m, 2H), 7.4–7.25 (m, 5H), 7.20 (m, 1H), 6.95–6.8 (m, 2H), 5.2–5.05 (m, 2H), 4.99 (dd, 1H), 4.64.2 (m, 2H), 4.5–4.15 (m, 2H), 3.8–3.6 (m, 2H), 4.12 (m, ½H), 3.91 (m, ½H), 3.61 (m, ½H), 3.44 (m, ½H), 2.4–2.2 (s+s, 3H).

Intermediate 19

3-(4-Fluoro-2-methyl-phenyl)-piperazine-1-carboxylic Acid 1-(S)-phenyl-ethyl ester To a solution of 1,1'carbonyldiimidazole (0.162 g) in DCM (5 mL) (S)-sec-phenethyl alcohol (0.122 g) was added. After 30 min. a solution of intermediate 7 (0.180 g) in acetonitrile (5 mL) was added and the mixture refluxed for 2 hr. Then the mixture was concentrated to give the crude product, which was purified by flash chromatography (CH/AcOEt 8:2) to give the title compound (mix diastereomers) (0.180 g) as a foam.

NMR (DMSO) δ (ppm) 7.87 (m, 1H); 7.40–7.25 (m, 5H); 7.02–6.94 (m, 2H); 5.74 (m, 1H); 3.93–3.71 (m, 3H); 3.00–2.55 (m, 4H); 2.34 (s, 3H); 2.28 (s, 3H)

Intermediate 20

4-(3,5-Bis-trifluoromethyl-benzyl-carbamoyl)-3-(R)-(4-fluoro-2-methyl-phenyl)-piperazine-1-carboxylic Acid 1-(S)-phenyl-ethyl Ester (diastereomer 1) (20a)

4-(3,5-Bis-trifluoromethyl-benzyl-carbamoyl)-3-(S)-(4-fluoro-2-methyl-phenyl)-piperazine-1-carboxylic Acid 1-(S)-phenyl-ethyl ester (diastereomer 2) (20b)

A solution of triphosgene (0.075 g) in DCM (5 mL) was added drop-wise to a solution of intermediate 19 (0.180 g) and TEA (0.35 mL) in DCM (5 mL) at 0° C. After 2 hr, DIPEA (0.3 mL) and (3,5-bistrifluoromethylbenzyl)-methyl-amine hydrochloride (0.209 g) were added and the mixture was warmed at r.t. After 4 hr, DCM was added and the organic phase was washed with HCl 1N (2×10 mL) and brine, dried and concentrated to give the crude diastereoisomeric mixture. Separation by flash chromatography (CH/AcOEt 8:2) yielded the title compound 20a (0.125 g) and the title compound 20b (0.135 g) as white foams.

Intermediate 20a: NMR (DMSO) δ (ppm) 7.90 (s, 1H); 7.67 (s, 2H); 7.4–7.27 (m, 6H); 6.95 (dd, 1H); 6.80 (m, 1H); 5,74 (q, 1H); 4.60–4.40 (dd, 2H); 4.50 (m, 1H); 3.79 (m, 3H); 3.00 (m, 3H); 2.87 (s, 3H); 2.29 (s, 3H); 1.46 (d, 3H).

Intermediate 20b: NMR (DMSO) δ (ppm) 7.90 (s, 1H); 7.67 (s, 2H); 7.37–7.24 (m, 6H); 6.95 (dd, 1H); 6.81 (m, 1H); 5.75 (q, 1H); 4.60–4.41 (dd, 2H); 4.52 (m, 1H); 3.83–3.00 (m, 6H); 2.88 (s, 3H); 2.33 (s, 3H); 1.48 (d, 3H).

Intermediate 21

[1-(2,4-Bis-trifluoromethyl-phenyl)-ethyl]-methyl-amine

To a 2 M solution of MeNH$_2$ in MeOH (10 mL) commercial 3,5-bis(trifluoromethyl)acetophenone (2.1 g) was added. After 12 hr the mixture was cooled at 0° C. and then NaBH$_4$ (0.512 g) was added. After 1 hr the mixture was quenched with H$_2$O and extracted with DCM. Then the organic phase was dried and concentrated to give the crude product which was purified by distillation to obtain the title compound (1.5 g) as an oil.

NMR (CDCl$_3$) δ (ppm) 7.8 (m, 3H); 3.8 (q, 1H); 2.4 (s, 3H); 1.4 (d, 3H)

Intermediate 22

4-{[1-(3,5-Bis-trifluoromethyl-phenyl)-ethyl]-methyl-carbamoyl}-3-(4-fluoro-2-methyl-phenyl)-piperazine-1-carboxylic acid benzyl ester (mixture of enantiomers A,B) (22a)

4-{[1-(3,5-Bis-trifluoromethyl-phenyl)-ethyl]-methyl-carbamoyl}-3-(4-fluoro-2-methyl-phenyl)-piperazinyl-1-carboxylic acid benzyl ester (mixture of enantiomers C,D) (22b)

To a solution of 4-benzyloxycarbonyl-2-(4-fluoro-2-methyl-phenyl)-piperazine-1-carbonyl chloride (0.075 g) in DCM (5 mL) DIPEA (0.12 mL) and intermediate 21 (0.1 g) were added. The mixture was refluxed for 2 hr. then acetonitrile (5 mL) was added and the obtained solution was heated 70° C. and the mixture was stirred overnight. Then the mixture was concentrated and the residue was dissolved in AcOEt. The organic phase was washed with HCl 1N and brine and dried. The organic phase was concentrated to give the crude mixture of diastereomeric compounds which were separated by flash chromatography (CH/AcOEt 8:2) to obtain the title compound 22a (0.05 g) and title compound 22b (0.55 g) as white foams.

Intermediate 22a: NMR (CDCl$_3$) δ (ppm) 7.78 (s, 1H); 7.58 (s, 2H); 7.4–7.3 (m, 5H); 7.18 (m, 1H); 6.86 (m, 1H); 6.77 (m, 1H); 5.45 (m, 1H); 5.16 (s, 2H); 4.6 (m, 1H); 3.94 (m, 2H); 3.44–3.10 (m, 4H); 2.68 (s, 3H); 2.4 (s, 3H); 1.49 (d, 3H).

Intermediate 22b: NMR (CDCl$_3$) δ (ppm) 7.75 (s, 1H); 7.53 (s, 2H); 7.4–7.3 (m, 5H); 7.18 (m, 1H); 6.87 (m, 1H); 6.78 (m, 1H); 5.59 (m, 1H); 5.18 (s, 2H); 4.59 (m, 1H); 3.97 (m, 2H); 3.44–3.06 (m, 4H); 2.78 (s, 3H); 2.37 (s, 3H); 1.53 (d, 3H).

Intermediate 23

(4-Fluoro-2-methyl-phenyl)-oxo-acetic acid methyl ester

1) To a suspension of magnesium turnings (617 mg) in anh. THF (6 mL), at r.t., under N$_2$, a small crystal of I$_2$ was added, followed by 10% of a solution of commercial 2-bromo-5-fluorotoluene (4.0 g) in anh. THF (15 mL). The suspension was heated gently (heat gun) until the brown colour disappeared. The remaining bromide solution was added drop-wise, maintaining the reaction mixture warm (50–60° C.) with an oil bath. After the addition was complete (15 min), the suspension was stirred at 70° C. until the magnesium turnings had almost completely reacted (2 hr). The new brown solution was used in the next step.

2) A solution of LiBr (4.41 g) in anh. THF (50 mL) was added drop-wise to a suspension of CuBr (3.64 g) in anh. THF (50 mL). The reaction mixture was stirred at r.t. for 1 hr (dark green solution with a small amount of white solid in suspension). The Grignard solution previously prepared was then added dropwise (an ice bath was used to maintain the temperature <25° C.) followed by methyl oxalyl chloride (1.95 mL). The reaction mixture was stirred at r.t. for 2 hr. The THF was evaporated and the residue was taken up in AcOEt. The organic layer was washed with sat.aq. NH$_4$Cl (2×) and dried. The solids were filtered and the solvent evaporated to give a crude oil, which was purified by flash chromatography (CH/AcOEt 95:5) to obtain the title compound as a clear oil (2.44 g).

NMR (CDCl$_3$): δ (ppm) 7.74 (m, 1H), 6.98–7.04 (m, 2H), 3.96 (s, 3H), 2.61 (s, 3H).

Intermediate 24

(4-Fluoro phenyl)-oxo-acetic Acid Methyl Ester

To magnesium turnings (0.066 g), previously heated at 90° C. and covered by THF (1 mL), a crystal of iodine was added followed by a solution of commercial 4-Fluoro-bromobenzene (0.437 g) in THF (4 mL). The temperature was kept at 60° C. till the consumption of the metal. The solution of the organometallic derivative was added drop-wise on a solution of CuBr (0.356 g),and LiBr (0.431 g) in THF (10 mL), previously prepared at 0° C.

At the end of the addition, methyl oxalyl chloride (0.225 mL) was added via syringe and the reaction mixture was stirred 2 h at r.t, before being poured into an aqueous saturated solution of NH$_4$Cl and extracted with Et$_2$O. The organic phase was washed with brine and dried. The crude product obtained after evaporation of solvents was purified by column chromatography (CH/AcOEt 95:5) affording the title compound (0.2 g) as a solid.

$^1$H-NMR (CDCl$_3$): δ (ppm): 8.12 (m, 2H), 7.20 (m, 2H), 3.99 (s, 3H).

Intermediate 25

3-(4-Fluoro-2-methyl-phenyl)-5,6-dihydro-1H-pyrazin-2-one

To a solution of intermediate 23 (2.0 g) and ethylenediamine (684 µL) in toluene (40 mL), at r.t., under N$_2$, anh. Na$_2$SO$_4$ (2 g) was added. The reaction mixture was heated at reflux for 6 hr. It was then cooled down to r.t. and filtered The solids were rinsed with DCM. The solvent was evaporated and the crude oil was purified by flash chromatography (AcOEt) affording the title compound as a white solid (1.29 g).

NMR (CDCl$_3$): δ (ppm) 7.33 (m, 1H), 6.95–6.90 (m, 2H), 6.56 (m, 1H), 3.97 (m, 2H), 3.58 (m, 2H), 2.31 (s, 3H).

Intermediate 25a 3-(4-Fluoro-2-methyl-phenyl)-piperazin-2-one

To a solution, at 25° C., of intermediate 25 (168 g) in Methanol (2400 mL) under nitrogen, Pd/C 10% (44 g) was added. The reaction mixture was placed under a H$_2$ atmosphere and stirred at 25° C. for about 16 hours (till no further hydrogen was consumed and the reaction was completed by TLC, EAtMeOH 9/1). The catalyst was filtered in nitrogen atmosphere and the solvent was removed to low volume (360 mL) then Methanol (2040 mL) and Ethyl Acetate (9600 mL) were added and a silica pad (800 g) was performed; the eluted solution was concentrated to obtain the title compound (136 g).

$^1$H-NMR (DMSO) δ (ppm) 7.77 (bm, 1H); 7.24 (dd, 1H); 6.96 (dd, 1H); 6.92 (td, 1H); 4.43 (s, 1H); 3.30 (m, 1H); 3.14 (m, 1H); 2.92 (m, 1H); 2.82 (m, 2H); 2.33 (s, 3H).

Intermediate 26

3-(4(4-Fluoro-phenyl)-5,6 dihydro-1H-pyrazin-2-one

Intermediate 24 (0.190 g) was dissolved in dry toluene (5 mL) under inert atmosphere; ethylenediamine (0.072 mL) was added dropwise followed by Na$_2$SO$_4$ (0.2 g) and the reaction mixture was refluxed 2 hr. The solids were filtered off and the crude product obtained after evaporation of the solvent was purified by flash chromatography (AcOEt/MeOH 9:1) affording the title compound (0.155 g as a white solid).

mp 118–120° C.

$^1$H-NMR (CDCl$_3$) δ (ppm): 7.96 (m, 2H), 7.08 (m, 2H), (bs, 1H), 3.96 (t, 2H), 3.54 (m, 2H).

Intermediate 27

Bromo-(2,4-dichloro-phenyl)-acetic Acid Methyl Ester

To a stirred solution of commercial 2,4-dichlorophenylacetic acid (2 g) in DCM (50 mL) DMF (0.1 mL) and oxalyl chloride (1.7 mL) were added and the reaction mixture was heated at reflux for 1½ hr. The solvent was evaporated and the crude compound was dissolved in carbon tetrachloride (40 mL). N-bromosuccinimide (1.8 g) and 2,2'-azobis(2-methylpropionitrile) (0.1 g) were added and the reaction mixture was heated at reflux and irradiated for 2 hr. After cooling, methanol (50 mL) was added and the reaction mixture was stirred for 1 hr. The solution was concentrated, diluted with AcOEt and washed with a 3N HCl and brine. The organic phase was dried and concentrated to give a crude residue, which was purified by flash chromatography (CH/AcOEt 9:1) to obtain a mixture of the title compound and 2,4-dichlorophenyl-acetic acid methyl ester (1.3 g).

This mixture was dissolved in carbon tetrachloride (20 mL) then N-bromosuccinimide (0.89 g) and 2,2'-azobis(2-methylpropionitrile) (0.05 g) were added and the reaction mixture was heated at reflux and irradiated for 3½ hr. The solution was concentrated, diluted with AcOEt and washed with a saturated solution of $Na_2CO_3$ and brine. The organic phase was dried and concentrated to give a crude residue which was purified by flash column chromatography (CH/AcOEt 9:1) to yield the title compound (1.14 g, pale yellow oil).

NMR ($CDCl_3$): δ (ppm) 7.72 (d, 1H), 7.40 (d, 1H), 7.30 (dd, 1H), 5.84 (s, 1H), 3.81 (s, 3H).

Intermediate 28

Bromo-(3,4-dichloro-phenyl)-acetic acid methyl ester

DMF (0.1 ml) and oxalyl chloride (1.7 ml) were added to a solution of commercial 3,4-dichlorophenylacetic acid (2 g) in DCM (100 ml) and the reaction mixture was heated at reflux for 1½ hr. After cooling, methanol (50 mL) was added and the reaction mixture was stirred for 1 hr. The solvent was evaporated and the crude compound was purified by flash chromatography (CH/AcOEt 9:1) to obtain the methyl ester that was dissolved in carbon tetrachloride (60 mL). N-Bromosuccinimide (2.06 g) and 2,2'-azobis(2-methylpropionitrile) (0.2 g) were added and the reaction mixture was heated at reflux and irradiated for 2 hr. The solution was concentrated, diluted with ethyl acetate and washed with a saturated solution of $Na_2CO_3$ and brine. The organic phase was next dried with $Na_2SO_4$ and concentrated to give a crude residue which was purified by flash chromatography (CH/AcOEt 9:1) to obtain the title compound (2.0 g) as an oil.

NMR ($CDCl_3$) δ (ppm) 7.70 (s, 1H), 7.45 (m, 1H), 5.25 (s, 1H), 3.80 (s, 3H).

Intermediate 29

3-(2,4-Dichloro-phenyl)-piperazine-2-one

To a solution of intermediate 27 (1.14 g) in EtOH (20 mL) sodium ethoxide (0.34 g) and ethylenediamine (0.54 mL) were added and the reaction mixture was stirred at r.t. for 15 hr. The solvent was evaporated and the residue was purified by flash chromatography to yield the title compound (0.35 g) as a white foam.

NMR (DMSO): δ (ppm) 7.87 (broad, 1H), 7.55 (d, 1H), 7.41, 7.37 (d+dd, 2H), 4.63 (s, 1H), 3.32, 3.14 (m+m, 2H), 3.02–2.90, 2.84 (m+m, 3H).

Intermediate 30

3-(3,4-Dichloro-phenyl)-piperazine-2-one

To a solution of intermediate 28 (2.0 g) in EtOH (100 ml) sodium ethoxide (0.60 g) and ethylenediamine (0.95 ml) were added and the reaction mixture was stirred at r.t. for 15 hr. The solvent was evaporated and the residue was diluted with ethyl acetate and washed with brine. The organic phase was dried and concentrated to give the title compound (2.0 g) as a white foam).

NMR ($CDCl_3$): δ (ppm) 7.60 (d, 1H), 7.42 (d, 1H), 7.32, (dd, 1H), 5.91 (sa, 1H), 4.53 (s, 1H), 3.6–3.1 (m+m, 4H).

Intermediate 31

3-Oxo-2-phenyl-piperazine-1-carbonyl Chloride

To a stirred solution of triphosgene (0.558 g) in DCM (10 ml) pyridine (0.46 mL) was added at 0° C. and, after 10 min, 3-phenyl-piperazine-2-one (1 g). The ice bath was removed and the mixture was stirred at room temperature overnight. The mixture was concentrated and the product was purified by flash chromatography (CH/AcOEt 1:1) to give the title compound (0.253 g) as a foam.

NMR ($CDCl_3$): δ (ppm): 7.45–7.35 (m, 5H); 6.81 (bs, 1H); 6.61 (bs, 1H); 5.99 (s, 1H); 4.3–4.2 (m, 1H); 3.7–3.3 (m, 3H).

Intermediate 32

2-(4-Fluoro-2-methyl-phenyl)-3-oxo-piperazine-1-carboxylic acid (3,5-bis-trifluoromethyl-benzyl)-methyl-amide To a solution of intermediate 25 (63 mg) in anh. MeOH (6.1 mL), at r.t., under $N_2$, Pd/C 10% (7 mg, 10% wt) was added. The reaction mixture was placed under an $H_2$ atmosphere and was stirred at r.t. for 2 hr. The catalyst was filtered (filtering paper) and the solvent was evaporated. The crude 3-(4-Fluoro-2-methyl-phenyl)-piperazin-2-one (64 mg) was dried under high vacuum and dissolved in anh. DCM (4.0 mL), at 0° C., under $N_2$, and TEA (85 μL) was added. Then, a solution of triphosgene (37 mg) in anh. DCM (2 mL) was added drop-wise. The reaction was stirred at 0° C. for 2 hr. To this solution DIPEA (107 μL) and N-methyl-bis(trifluoromethyl)-benzylamine hydrochloride (108 mg) were added. The solution was stirred at r.t. for 18 hr. The reaction mixture was diluted with DCM, washed with 1N HCl (1×) and dried. The solids were filtered and the solvent evaporated. The crude product was purified by flash chromatography (AcOEt) to give the title compound as a white solid (93 mg).

NMR ($CDCl_3$): δ (ppm) 7.79 (s, 1H), 7.59 (s, 2H), 7.20 (bs, 1H), 6.91–6.84 (m, 1H), 6.07 (m, 1H), 5.69 (s, 1H), 4.58–4.47 (dd, 1H), 3.49 (m, 4H), 2.85–2.39 (s, 6H).

Intermediate 33

2-(4-Fluoro-phenyl)-3-oxo-piperazine-1-carboxylic acid (3,4-bis-trifluoromethyl-benzyl)-methyl-amide Intermediate 26 (0.135 g) was dissolved in MeOH (5 mL) and the temperature lowered at 0° C., then $NaBH_4$ (0.102 g) was carefully added. After 2 hr the reduction was complete, the solvent was removed under reduced pressure and DCM was added. The organic phase was washed with $H_2O$ and brine before being dried on $Na_2SO_4$. The crude 3-(4-Fluoro-phenyl)-piperazin-2-one (0.140 g) was dried under high vacuum and dissolved in anhydrous DCM (5 mL), at 0° C. and TEA (0.433 mL) was added drop-wise. To this solution a solution of triphosgene (0.09 g) in dry DCM (3 mL) was added at 0° C., under inert atmosphere. The temperature was maintained at 0° C. for 3 hr. then DIPEA (0.4 mL) followed by 3,5-bistrifluoromethyl-methyl-amine hydrochloride (0.27 g) were added. The reaction mixture was stirred at r.t. overnight before being diluted with DCM and washed with a 1N solution of HCl, $H_2O$ and brine. The organic phase was dried and the crude product obtained after evaporation of the solvent was purified by flash column chromatography (AcOEt) affording the title compound as a foam (0.2 g).

NMR (DMSO): δ (ppm) 8.14 (bs, 1H), 7.97 (s, 1H), 7.78 (s, 2H), 7.37 (m, 2H), 7.09 (m, 2H), 5.13 (s, 1H), 4.49 (dd, 2H), 3.5–3.25 (m, 4H), 2.80 (s, 3H).

Intermediate 34

3-Oxo-2-phenyl-piperazine-1-carboxylic acid (3,5-bis-trifluoromethyl-benzyl)-methyl-amide To a stirred solution of intermediate 31 (0.239 g) in DMF (5 mL) DIPEA (0.41 mL) and 3,5-bistrifluoromethyl-methyl-amine hydrochloride (0.366 g) were added. After 3 hr the mixture was quenched with brine and the aqueous layer was extracted with AcOEt. The organic layer was dried and concentrated at reduced pressure. The product was purified by flash chromatography (AcOEt) to give the title compound (0.429 g).

NMR (CDCl$_3$): δ (ppm): 7.79(bs, 1H); 7.67(bs, 2H); 7.50(d, 2H); 7.35(m, 3H); 5.98(s, 1H); 5.43(s, 1H); 4.63–4.32(dd, 2H); 3.88–3.56(m, 2H); 3.50–3.30(m, 2H); 2.81(s, 3H).

Intermediate 35

2-(2,4-Dichloro-phenyl)-3-oxo-piperazine-1-carboxylic acid (3,5-bis-trifluoromethyl-benzyl)-methyl-amide To a solution of intermediate 29 (0.33 g) in DCM (30 mL) TEA (0.65 mL) and, dropwise, a solution of triphosgene (0.23 g) in DCM (10 mL) were added. The reaction mixture was stirred at r.t. for 1½ hr then concentrated and purified by flash chromatography to yield 2-(2,4-dichloro-phenyl-3-oxo-piperazine-1-carbonyl chloride (0.3 g, white foam). The latter was dissolved in DCM (30 mL), then DIPEA (0.3 mL) and (3,5-bistrifluoromethylbenzyl)-methyl-amine hydrochloride (0.32 g) were added. The reaction mixture was stirred at reflux for 3 hr. then washed with a 1N solution of HCl and brine. The organic phase was next dried and concentrated to give the crude product which was purified by flash chromatography (from AcOEt 100% to AcOEt/MeOH 8:2) to obtain the title compound (0.45 g) as a white foam.

NMR (DMSO) δ (ppm) 8.30 (bs, 1H), 7.96 (bs, 1H), 7.73 (bs, 1H), 7.54 (d, 1H), 7.35, 7.33 (d+dd, 2H), 5.44 (s, 1H), 4.61 (d, 1H), 4.39 (d, 1H), 3.39, 3.25 (m+m, 4H), 2.76 (s, 3H).

Intermediate 36

2-(3,4-Dichloro-phenyl)-3-oxo-piperazine-1-carboxylic acid (3,5-bis-trifluoromethyl-benzyl)-methyl-amide To a solution intermediate 30 (0.413 g) in DCM (40 mL) TEA (1.4 mL) and, dropwise, a solution of triphosgene (0.25 g) in DCM (10 mL) was added. The reaction mixture was stirred at r.t. for 1½ hr, then DIPEA (0.6 mL) and (3,5-bistrifluoromethylbenzyl)-methyl-amine hydrochloride (0.54 g) were added. The reaction mixture was stirred at reflux for 3 hr, then washed with a 1N solution of HCl and brine. The organic phase was next dried and concentrated to give the crude product which was purified by flash chromatography (from AcOEt 100% to AcOEtVMeOH 8:2) to give the title compound (0.13 g, white foam).

NMR (DMSO) δ (ppm) 8.24 (bs, 1H), 7.96 (s, 1H), 7.75 (s, 2H), 7.54 (d, 1H), 7.51(d, 1H), 7.33 (dd, 1H), 5.11 (s, 1H), 4.49 (dd, 2H), 3.5–3.25 (m+m, 4H), 2.82 (s, 3H).

Intermediate 37

4-(3,5-Bis-trifluoromethyl-benzyl-carbamoyl)-3-(4-fluoro-2-methyl-phenyl)-piperazine-1-carboxylic acid 1-(R)-phenyl-ethyl ester (diastereomer 1) (37a)

4-(3,5-Bis-trifluoromethyl-benzyl-carbamoyl)-3-(4-fluoro-2-methyl-phenyl)-piperazine-1-carboxylic acid 1-(R)-phenyl-ethyl ester (diastereomer 2) (37b)

To a solution of carbonyl diimidazole (402 mg) in DCM (8.3 mL), at r.t., under N$_2$, (R)-sec-phenylethyl alcohol (0.3 mL) was added. The solution was stirred at r.t. for 1 hr. Example 11 (790 mg) in anh. acetonitrile (8.3 mL) was then added to the solution and the reaction mixture was heated at 50° C. without a water condenser in order to evaporate the DCM. A water condenser was then adjusted to the flask and the reaction mixture was refluxed for 4 hr. The solvent was then evaporated and the residue partitioned between AcOEt/1N HCl. The phases were separated and the organic layer was washed with sat. aq. NaCl (2×). It was then dried and the solvent evaporated. The crude oil was purified by flash chromatography (CH/AcOEt 8:2). The mixed fractions were re-chromatographed using the same conditions. Intermediates 37a (242 mg) and 37b (152 mg) were obtained as white foams.

Intermediate 37a: NMR (DMSO) δ (ppm): 7.90 (s, 1H); 7.67 (s, 2H); 7.37–7.24 (m, 6H); 6.95 (dd, 1H); 6.81 (m, 1H); 5.75 (q, 1H); 4.60–4.41 (dd, 2H); 4.52 (m, 1H); 3.83–3.00 (m, 6H); 2.88 (s, 3H); 2.33 (s, 3H); 1.48 (d, 3H).

Intermediate 37b: NMR (DMSO) δ (ppm): 7.90 (s, 1H); 7.67 (s, 2H); 7.4–7.27 (m, 6H); 6.95 (dd, 1H); 6.80 (m, 1H); 5,74 (q, 1H); 4.60–4.40 (dd, 2H); 4.50 (m, 1H); 3.79 (m, 3H); 3.00 (m, 3H); 2.87 (s, 3H); 2.29 (s, 3H); 1.46 (d, 3H).

Intermediate 38

4-{[1-(S)-(3,5-Bis-trifluoromethyl-phenyl)-ethyl]-methyl-carbamoyl}-3-(S)-(4-fluoro-2-methyl-phenyl)-piperazine-1-carboxylic acid 1-(R)-phenyl-ethyl ester (diastereomer 1) (38a)

4-{[1-(R)-(3,5-Bis-trifluoromethyl-phenyl)-ethyl]-methyl-carbamoyl}-3-(R)-(4-fluoro-2-methyl-phenyl)-piperazine-1-carboxylic acid 1-(R)-phenyl-ethyl ester (diastereomer 2) (38b)

To a solution of 1,1' Carbonyldiimidazole (0.163 g) in DCM (5 mL) (R)-sec-phenethyl alcohol (0.122 g) was added and the mixture was stirred at room temperature for 30 min. Then a solution of example 10 (0.250 g) in acetonitrile (5 mL) was added and the mixture was refluxed for 4 hr. The mixture was cooled and AcOEt was added. The organic phase was washed with HCl 1N (2×50 mL) and brine, dried and concentrated to give the crude mixture of diastereomers, which were separated by flash chromatography (CH/AcOEt 8:2) to obtain the title compound 38a (diastereomer 1–0.08 g) and the title compound 38b (diastereomer 2–0.08 g).

Intermediate 38a: NMR (CDCl$_3$) δ (ppm) 7.74 (s, 1H); 7.52 (s, 2H); 7.40–7.24 (m, 5H); 7.18 (m, 1H); 6.87 (m, 1H); 6.80 (m, 1H); 5.86 (q, 1H); 5.57 (q, 1H); 4.7–4.46 (m, 1H); 3.98 (m, 2H); 3.44–2.96 (m, 4H); 2.77 (s, 3H); 2.36 (s, 3H); 1.54 (m, 6H).

Intermediate 38b NMR (CDCl$_3$) δ (ppm) 7.74 (s, 1H); 7.53 (s, 2H); 7.40–7.26 (m, 5H); 7.16 (m, 1H); 6.87 (m, 1H); 6.78 (m, 1H); 5.86 (q, 1H); 5.57 (m, 1H); 4.62 (m, 1H); 4.04 (m, 1H); 3.84 (m, 1H); 3.50–3.04 (m, 4H); 2.76 (s, 3H); 2.41 (s, 3H); 1.56 (m, 6H).

Intermediate 39

(+)(S)-3-(4-Fluoro-2-methyl-phenyl)-piperazin-2-one

Method A

To a suspension of intermediate 25 (35 g) in AcOEt (900 mL), L(+)-Mandelic Acid (27.3 g) was added. The suspension was stirred at r.t. for 1 hr then at 3–5° C. for 2 hr, filtered and dried under vacuum at r.t to obtain crude L(+)-mandelate 3-(4-fluoro-2-methyl-phenyl)-piperazin-2one (37 g), which was suspended in AcOEt (370 mL) and heated to reflux till complete solubilisation then cooled to room temperature and stirred for further 2 hours, filtered, washed with of AcOEt (150 mL) and dried under vacuum obtaining (+) L-mandelate 3-(4-Fluoro-2-methyl-phenyl)-5,6 pyrazin-2-one (30.4 g) as white solid. This material (30.4 g) was suspended in AcOEt (300 mL) and treated with NaOH (0.73M, 155 mL) saturated with NaCl. The organic phase was then washed with water (90 mL). The aqueous phase was counter-extracted 4 times with AcOEt (90 mL). The combined organic phase (1800 mL) was dried on 10 g of $Na_2SO_4$ and concentrated under vacuum obtaining the title compound (25.04 g) as white foam.

Method B

To a solution, heated at 45° C., of intermediate 25a(168 g) in Ethyl Acetate (2000 mL) L(+)-Mandelic Acid (116 g) and 3,5-dichloro-salicilaldehyde (10.8 g) were added. The solution was stirred for 30 min at 45° C. then seeded with white crystals of L(+)mandelate-3-(4-Fluoro-2-methyl-phenyl)-piperazin-2-one (0.4 g). The obtained suspension was stirred under nitrogen atmosphere at 45° C. for 16 hours then stirred for further 4 hour at 0° C., washed with cooled Ethyl Acetate (2×200 ml) then dried under vacuum at room temperature for 2 hours to obtain L(+)mandelate-3-(4-Fluoro-2-methyl-phenyl)-piperazin-2-one(126.22 g) as a white/yellowish solid which was suspended in DCM (2760 mL) then NaOH 0.8M in Brine (17.35 g of NaOH in 530 mL of Brine) was added. The organic phase was then washed with Brine (380 mL) and the aqueous phase was counter extracted four times with DCM (4×1500 mL). The combined organic phase was dried and concentrated to obtain the title compound (60.35 g).

$^1$H-NMR (DMSO) δ (ppm) 7.77 (bm, 1H); 7.24 (dd, 1H); 6.96 (dd, 1H); 6.92 (td, 1H); 4.43 (s, 1H); 3.30 (m, 1H); 3.14 (m, 1H); 2.92 (m, 1H); 2.82 (m, 2H); 2.33 (s, 3H).

HPLC: Chiralcel OJ (4.6×250 mm) from Daicel; Mobile Phase:n-Hexane/Ethanol 80:20 v/v; Flow:1 mL/min; Detector: UV@ 265 nm (or 210 nm for higher signals); Dissolution phase:n-Hexane/Ethanol 80/20 v/v; Sample Concentration 1 mg/ml; Injection: 5 uL; Retention times: 2:8.4 min. $[α]_D$(solvent $CHCl_3$, Source: Na; Cell volume [ml]: 1; Cell pathlength [dm]:1; Cell temperature [° C.]: 20; Wavelength [nm]: 589; Conc. sample [% p/v]:1.17)=+17.9.

Intermediate 40

2-(S)-(4-Fluoro-2-methyl-phenyl)-3-oxo-piperazine-1-carboxylic acid [1-(R)-(3,5-bis-trifluoromethyl-phenyl)-ethyl]-methyl-amide (40a)

2-(S)-(4-Fluoro-2-methyl-phenyl)-3-oxo-piperazine-1-carboxylic acid [1-(S)-(3,5-bis-trifluoromethyl-phenyl)-ethyl]-methyl-amide.(40b).

To a solution of intermediate 39 (12.1 g) in anhydrous DCM (270 mL), TEA (16.4 mL) was added. The solution was cooled down to 0° C. and a solution of triphosgene (7.3 g) in anh. DCM (60 mL) was added drop-wise over 40 min. The reaction mixture was stirred at 0° C. for 4 hr and was brought back to r.t. DIPEA (20.2 mL) was then added, followed by a solution of [1-(3,5-bis-trifluoromethyl-phenyl)ethyl]-methyl-amine (23.6 g) in acetonitrile (300 mL) and an additional amount of acetonitrile (300 mL). The reaction mixture was warmed up to 95° C. (oil bath T° C.) without a water condenser to evaporate the DCM. When the internal temperature had reached 70° C., the flask was equipped with a water condenser, and the reaction mixture was heated at 70° C. for an additional 2 hr (4 hr total). It was then brought back to r.t. and the solvent was evaporated. The residue was partitioned between DCM/2% HCl and the phases were separated. The aqueous layer was extracted with DCM (1×) and the combined organic extracts were dried. The solids were filtered and the solvent evaporated to give a crude mixture of title compounds which were purified by flash chromatography (AcOEt/CH 8:2) to obtain the title compounds 40a (8.8 g) and 40b (9.0 g) as white foams.

NMR ($^1$H, DMSO-$d_6$): δ 8.16 (s, 1H), 7.98 (s, 2H), 7.19 (dd, 1H), 6.97 (dd, 1H), 6.87 (td, 1H), 5.34 (s, 1H), 5.14 (q, 1H), 3.45–3.2 (m, 4H), 2.53 (s, 3H), 2.27 (s, 3H), 1.56 (d, 3H).

Intermediate 40b: NMR ($^1$H, DMSO-$d_6$): δ 8.16 (s, 1H), 7.95 (s, 2H), 7.19 (dd, 1H), 6.98 (dd, 1H), 6.90 (td, 1H), 5.29 (q, 1H), 5.28 (s, 1H), 3.45–3.15 (m, 4H), 2.66 (s, 3H), 2.27 (s, 3H), 1.52 (d, 3H).

Intermediate 41

4-[2-(1,3-Dioxo-1,3dihydro-isoindol-2-yl)-ethyl]-2-(4-fluoro-2-methyl-phenyl)-piperazine-1-carboxylic acid (3,5-bis-trifluoromethyl-benzyl)-methyl-amide

To a solution of example 8 (0.05 g) in anhydrous DMF (1 mL), under $N_2$, at room temperature, were added TEA (40 µl) and N-(2-bromoethyl)-phthalimide (28 mg). The reaction mixture was stirred at 80° C. for 5 hr and was then cooled down to room temperature. It was poured in sat.aq. NaCl and the phases were separated. The organic layer was washed with sat. aq. NaCl (2×), dried and the solvent evaporated. The crude product was purified by flash chromatography (CH/AcOEt 1:1) to give the title compound (0.25 g) as a yellow oil.

NMR (DMSO) δ (ppm) 7.94 (s, 1H), 7.80–7.90 (m, 4H), 7.67 (s, 2H), 7.33 (m, 1H), 6.91 (dd, 1H), 6.45 (td, 1H), 4.60 (d, 1H), 4.34 (m, 2H), 3.80 (m, 1H), 3.64 (m, 1H), 3.18 (m, 1H), 2.82 (s, 3H), 2.79 (m, 1H), 2.80 (m, 1H), 2.66 (m, 1H), 2.60 (m, 2H), 2.46 (m, 1H), 2.26 (m, 1H), 2.27 (s, 3H).

IR (Nujol) ($cm^{-1}$) 1650–1773.

MS (m/z) 651 [MH], 673 $[M+Na]^+$.

Intermediate 42

1-(4-Fluoro-2-methyl-phenyl)-propane-1,2-dione

1) To a suspension of magnesium turnings (283 mg) in anh. THF (3 mL), at r.t., under $N_2$, was added a small crystal of $I_2$, followed by 10% of a solution of 1-bromo-4-fluoro-2-methyl-benzene (2.0 g) in anhydrous. THF (8 mL). The suspension was heated gently (heat gun) until the brown colour disappeared. The remaining bromide was added drop-wise, maintaining the reaction mixture warm (50–60° C.) with an oil bath. After the addition was complete (15 min) the suspension was stirred at 70° C. until the magnesium turnings had almost completely reacted (2 hr). The new brown solution was used in the next step.

2) A solution of LiBr (2.26 g) in anh. THF (26 mL) was added drop-wise a suspension of CuBr (1.82 g) in anh. THF (26 mL). The reaction mixture was stirred at r.t. for 1 hr. The reaction mixture was then brought at −78° C. and the Grignard solution prepared above was added dropwise followed by pyruvyl chloride (1.13 g). The reaction mixture was stirred at −78° C. for 2 hr. The THF was evaporated and the residue was taken up in AcOEt. The organic layer was washed with sat.aq. NH$_4$Cl (2×), dried and evaporated to a crude oil, which was purified by flash chromatography (CH/AcOEt 95:5) to give the title compound as a yellow oil (0.58 g).

NMR (CDCl$_3$) δ (ppm). 7.68 (m, 1H), 6.98 (m, 2H), 2.56–2.52 (2s, 6H).

IR (Film) (cm$^{-1}$) 1712, 1674.

Intermediate 43

5-(4-Fluoro-2-methyl-phenyl)-6-methyl-2,3-dihydro-pyrazine

To a solution of intermediate 42 (0.58 g) and ethylenediamine (0.22 mL) in toluene (13 mL), at r.t., under N$_2$, was added anh. Na$_2$SO$_4$ (2 g). The reaction mixture was heated at reflux for 6 hr. It was then cooled down to r.t. and filtered. The solids were rinsed with DCM. The solvent was evaporated and the crude oil was purified by flash chromatography (AcOEt) to give the title compound as an orange oil (0.44 g).

NMR (CDCl$_3$) δ (ppm) 7.18 (m, 1H), 7.0–6.9 (m, 2H), 3.6–3.45 (2m, 4H), 2.20 (s, 3H), 1.88 (t, 3H).

IR (Film) (cm$^{-1}$) 1612, 1530.

MS (m/z) 204 [M]$^+$.

Intermediate 44

2-Methyl-3-(2-methyl-4-fluoro)-phenyl-piperazine-1-carboxylic acid benzyl Ester

To a solution of intermediate 43 (554 mg) in anh. MeOH (11 mL), under N$_2$, at r.t., was added Pd/C 10% (110 mg) and the reaction mixture was placed under an H$_2$ atmosphere for 2 hr. The catalyst was then filtered (filter paper) and rinsed with AcOEt. The solvent was evaporated and the residue dried under vacuum. 2-(4-Fluoro-2-methyl-phenyl)-3-methyl piperazine was obtained as a yellow oil (565 mg) and was dissolved in anh. DCM (27 mL), at −5° C., under N$_2$. TEA (549 μL) and benzyloxycarbonyl chloride (426 μL) were added to this solution. The solution was stirred at −5° C. for 2 hr., then it was poured in sat.aq. NaHCO$_3$/DCM and the phases were separated. The aqueous layer was extracted with DCM (1×) and the combined organic extracts were dried. The solids were filtered and the solvent evaporated. The crude oil was purified by flash chromatography (CH/AcOEt 1:1) to give the title compound was obtained as a yellow oil (111 mg).

NMR (CDCl$_3$) δ (ppm) 7.45–7.36 (m, 6H), 6.86 (m, 2H), 5.17 (m, 2H), 4.48–4.36 (m, 1H), 4.09–4.04 (2d, 1H), 4.05–3.94 (2bd, 1H), 3.25–2.88 (m, 3H), 2.40+2.28 (2s, 3H), 0.97+0.96 (2d, 3H).

IR (Film) (cm$^{-1}$) 1688.

MS (m/z) 343 [MH]$^+$.

Intermediate 45

4-[(3,5-Bis-trifluoromethyl-benzyl)-methyl-carbamoyl]-3-(4-fluoro-2-methyl-phenyl)-2-methyl-piperazine-1-carboxylic acid benzyl ester To a solution of intermediate 44 (358 mg) in anh. DCM (15 mL), at 0° C., under N$_2$, was added TEA (292 μL). To this solution was added a solution of triphosgene (140 mg) in anh. DCM (6 mL). The reaction mixture was stirred at 0° C. for 2 hr.

To this solution were added DIPEA (181 μL) and N-methyl-bis(trifluoromethyl)benzylamine hydrochloride (370 mg). The solution was stirred at r.t. for 18 hr. It was then diluted with DCM, washed with 10% citric acid (1×) and dried. The solvent was evaporated and the crude oil purified by flash chromatography (CH/AcOEt 6:4) to give the title compound (545 mg) as a white foam.

NMR (CDCl$_3$) δ (ppm) 7.76 (s, 1H), 7.50 (s, 2H), 7.34–7.30 (m, 5H), 7.00 (m, 1H), 6.85 (m, 1H), 6.76 (m, 1H), 5.2–5.1 (dd, 2H), 4.75 (d, 1H), 4.30 (d, 1H), 4.65 (m, 1H), 4.35 (m, 1H), 4.00 (m, 1H), 3.54–3.40 (m, 2H), 3.1 (m, 1H), 3.06 (s, 3H), 2.38 (s, 3H), 1.05 (d, 3H).

IR (Film) (cm$^{-1}$) 3437, 1705, 1664.

MS (m/z) 626 [MH]$^+$.

Intermediate 46

3-(2-Methyl-4-fluoro-phenyl)-5-methyl-5,6 dihydro-1H-pyrazin-2-one

Under inert atmosphere, intermediate 23 (0.2 g) was dissolved in dry toluene (5 mL), then 1,2-diaminopropane (0.102 mL) was added drop-wise followed by Na$_2$SO$_4$ (0.2 g) and the reaction mixture was refluxed for 2 hr; the solids were filtered off and the crude product obtained after evaporation of the solvent was purified by flash chromatography (AcOEt) affording the title compound in a mixture with 3-(2-Methyl-4-fluoro-phenyl)-6-methyl-5,6-dihydro-1H-pyrazin-2-one (0.200 g).

$^1$H-NMR (DMSO) δ (ppm) 8.42 (bs, 1H), 7.24 (m, 1H), 7.02 (m, 2H), 3.85 (m, 1H), 3.40 (dt, 1H), 3.13 (t, 1H), 2.18 (s, 3H), 1.25 (d, 3H).

IR (Nujol) (cm$^{-1}$) 3450, 1682, 1614. MS (m/z) 221 [MH]$^+$.

Intermediate 47

3-(2-Methyl-4-fluoro-phenyl)-5-Methyl-piperazin-2-one (mixture of syn enantiomers)

Intermediate 46 (0.180 g) was dissolved in MeOH (4 mL) and Pd/C 10% (36 mg) was added. After 2 hr the reduction was complete. The reaction mixture was filtered on a celite pad, the solvent was removed under reduced pressure and the crude product purified by flash-chromatography (AcOEt/MeOH 9:1) affording a 9:1 mixture of the title compound and the anti enantiomers (0.110 g).

$^1$H-NMR (DMSO) δ (ppm) 7.88 (s, 1H), 7.07–6.92 (m, 3H), 4.48 (s, 1H), 3.3 (m, 1H), 2.91 (m, 2H), 2.65 (bs, 1H), 2.34 (s, 3H), 0.95 (d, 3H).

IR (Nujol) (cm$^{-1}$) 3441, 3285, 1675.

MS (m/z): 223 [MH]$^+$.

Intermediate 48

2-(2-Methyl-4-fluoro-phenyl)-3-oxo-piperazine-6-methyl-1-carboxylic acid (3,5-bis-trifluoromethyl-benzyl)-methyl-amide; mixture of syn enantiomers To a solution of intermediate 47 (0.105 g) and triethylamine (0.197 mL) in dry DCM (5 mL) was added drop-wise, at 0° C., a solution of triphosgene (0.056 g) in dry DCM (3 mL) under inert atmosphere. The temperature was maintained at 0° C. for 3 hr. before the addition of DIPEA (0.3 mL) followed by 3,5-bistrifluoromethyl-methyl-amine hydrochloride (0.166 g). The reaction mixture was stirred at room temperature overnight before being diluted with DCM and washed with a 1N solution of HCl, H$_2$O and brine in sequence. The organic phase was dried and the crude product obtained after evaporation of the solvent was purified by flash chromatography (AcOEt/MeOH 9:1) affording the title compound as a foam (0.085 g).

$^1$H NMR (DMSO) δ (ppm) 8.08 (bt, 1H), 7.95 (s, 1H), 7.63 (s, 2H), 7.13 (t, 1H), 6.87 (d, 1H), 6.79 (t, 1H), 5.21 (s, 1H), 4.51 (dd, 2H), 3.64 (m, 1H), 3.30 (m, 1H), 3.18 (m, 1H), 2.77 (s, 3H), 2.25 (s, 3H), 1.20 (d, 3H).

IR (Nujol) (cm$^{-1}$) 1675.

MS (m/z): 506 [MH]$^+$

Intermediate 49

2-(3,5-Bis-trifluoromethyl-phenyl)-acrylic acid methyl ester

Palladium tetrakis (triphenylphosphine) (331 g), copper iodide (0.414 g) and 2-tributylstannyl-2-propenoic acid methyl ester (2.82 g) were added to a solution of 3,5-(bis-trifluoromethyl)iodobenzene (1 g) in dry DMF (10 mL) under a nitrogen atmosphere. The solution was stirred at r.t. for 16 hr, then diluted with water and extracted with AcOEt. The organic extract was dried, concentrated in vacuo and purified by flash chromatography (CH/AcOEt 9:1) to give the title compound (180 mg).

IR (CDCl$_3$): 1727 (C=O) cm$^{-1}$.

NMR (DMSO) δ (ppm) 7.95 (s, 1H); 7.89 (s, 1H); 7.87 (s, 1H); 6.6 (s, 1H); 6.06 (s, 1H); 3.87 (s, 3H).

Intermediate 50

1-(3,5-Bis-trifluoromethyl-phenyl)-cyclopropanecarboxylic acid methyl ester

Sodium hydride (60% suspension in mineral oil—86 mg) was added to a suspension of trimethylsulfoxonium iodide (515 mg) in dry DMF under a nitrogen atmosphere. The suspension was stirred at r.t. for 15 min., then a solution of intermediate 49 (0.58 g) in dry DMF (6 mL) was added. The mixture was stirred at r.t. for 30 min., then it was diluted with brine and extracted with ethyl acetate. The organic extract was dried, concentrated in vacuo and purified by flash chromatography (CH/AcOEt 9:1) to give the title compound (90 mg) as colourless oil.

Intermediate 51

1-(3,5-Bis-trifluoromethyl-phenyl)-cyclopropanecarboxylic acid

A mixture of intermediate 50 (90 mg) and lithium hydroxide (55.4 mg) in methanol (10 mL) was heated to reflux for 2 hrs. The organic extract was concentrated in vacuo and partitioned between a saturated ammonium chloride solution and AcOEt. The organic layer was washed with brine, dried and concentrated in vacuo to give the title compound (80 mg) as colourless oil.

Intermediate 52

4-[1-(3,5-Bis-trifluoromethyl-phenyl)-cyclopropylcarbamoyl]-3-(S)-(4-fluoro-2-methyl-phenyl)-piperazine-1-carboxylic acid tert-butyl ester TEA (150 μL) and diphenyphosphorylazide (175 μL) were added to a solution of intermediate 51 (80 mg) in dry toluene (25 mL) previously cooled to 0° C. under a nitrogen atmosphere. The solution was stirred at r.t. for 3 hr, then intermediate 54 (88 mg) was added and the mixture was heated to 100° C. for 1 hr. The mixture was allowed to cool to r.t. and partitioned between water and AcOEt. The organic layer was dried, concentrated in vacuo and the residue was purified by flash chromatography (CH/AcOEt 6:4) to give the title compound as a colourless oil (90 mg).

NMR (DMSO) δ (ppm) 7.75 (bs, 1H), 7.67 (bs, 2H), 7.29 (bs, 1H), 7.18 (dd, 1H), 6.96 (dd, 1H), 6.86 (dt, 1H); 5.17 (t, 1H), 3.75–3.42 (m, 5H), 3.18 (m, 1H), 2.29 (s, 3H), 1.3 (s, 9H); 1.3–1.1 (m, 4H).

MS: m/z=590 [M+H]$^+$.

Intermediate 53

4-{[1-(3,5-Bis-trifluoromethyl-phenyl)-cyclopropyl]-methyl-carbamoyl}-3-(S)-(4-fluoro-2-methyl-phenyl)-piperazine-1-carboxylic acid tert-butyl ester Sodium tert-butoxide (38.5 mg) was added to a solution of intermediate 52 (80 mg) in dry THF. The solution was stirred at r.t. for 10 min., then methyl iodide (40 μL) was added and stirring was continued for 1 h. The mixture was partitioned between water and AcOEt. The organic layer was dried, concentrated in vacuo to give the title compound as colourless oil (90 mg).

NMR (DMSO) δ (ppm) 7.8 (bs, 1H), 7.38 (dd, 1H), 7.34 (bs, 2H), 6.97 (dd, 1H), 6.93 (dt, 1H); 4.5 (bm, 1H), 3.64–2.97 (m, 9H), 2.28 (s, 3H), 1.38 (bs, 9H); 1.36–1.24 (2m, 4H).

MS: m/z=604 [M+H]$^+$, 626 [M+Na]$^+$

Intermediate 54

1-(Tert-Butoxycarbonyl)-3-(S)-(4-fluoro-2-methyl-phenyl)-piperazine

Di-tert-butyldicarbonate (271 mg) was added to a solution of intermediate 81 (301 mg) and TEA (315 μL) in DCM (10 mL) previously cooled to 0° C. under a nitrogen atmosphere. The solution was stirred at 0° C. for 40 min., then concentrated in vacuo. The residue was partitioned between water and AcOEt. The organic layer was washed with brine, dried and concentrated in vacuo. The residue was purified by flash-chromatography (CH/AcOEt 6:4) to give the title compound (80 mg) as a colourless gum.

NMR (d$_6$-DMSO): δ (ppm) 7.52 (m, 1H); 7.07–6.98 (m, 2H); 3.94–3.74 (m, 3H); 3.0–2.5 (m, 4H); 2.33 (s, 3H); 1.4 (s, 9H).

Intermediate 55

3-(3,5-Bis-trifluoromethyl-benzoyl)-1-vinyl-pyrrolidin-2-one

Trimethylsilyldiazomethane (11.5 mL) was added dropwise to a solution of 3,5-bis-(trifluoromethyl)benzoic acid (2 g) in dry toluene (20 mL) and methanol (0.5 mL) previously cooled to 0° C. under a nitrogen atmosphere. The solution was stirred at r.t. for 1 hr, then concentrated in vacuo to give 3,5-bis-(trifluoromethyl)-benzoic acid methyl ester (2 g) as a colourless oil. A solution of 3,5-bis-(trifluoromethyl)-benzoic acid methyl ester (2 g) and 1-vinyl-2-pyrrolidinone (863 μL) was added to a mixture of sodium hydride (60% suspension in mineral oil—0.41 g) in dry toluene (30 mL) previously heated to reflux. The mixture was stirred for 12 hrs, then it was partitioned between saturated ammonium chloride solution and AcOEt. The organic layer was dried, concentrated in vacuo and the residue was purified by flash chromatography (CH/AcOEt 8:2) to give the title compound (1.6 g) as a beige oil.

MS: m/z=352 [M+H]$^+$.

Intermediate 56

5-(3,5-Bis-trifluoromethyl-phenyl)-3,4-dihydro-2H-pyrrole

A solution of intermediate 55 (1.6 g) in THF (30 mL) was added dropwise over 1.5 h to a boiling solution of 6N HCl (50 mL) distilling at the same time the THF. At the end of the addition the distillation apparatus was removed and reflux was continued for further 4 hrs. The mixture was cooled to 0° C. and a 30% KOH solution was added until pH=12 was reached. The compound was extracted with DCM (4×10 mL). The combined organic extracts were dried, concentrated in vacuo and the residue was purified by flash chromatography (CH/AcOEt 7:3) to give the title compound (100 mg) as pale yellow oil.

NMR (DMSO) δ (ppm) 8.38 (s, 2H); 8.22 (s, 1H); 4.0 (t, 2H), 3.03 (tt, 2H); 1.99 (m, 2H).

MS: m/z=282 [M+H]$^+$.

Intermediate 57

2-(3,5-Bis-trifluoromethyl-phenyl)-pyrrolidine

Sodium borohydride (1.5 eq) was added to a solution of intermediate 56 (100 mg) in methanol (5 mL) previously cooled to 0° C. under a nitrogen atmosphere. The solution was diluted with water and extracted with AcOEt. The organic extract was dried and concentrated in vacuo to give the title compound (103 mg) as a pale yellow oil.

Intermediates 58

4-[2-(3,5-Bis-trifluoromethyl-phenyl)-pyrrolidine-1-carbonyl]-3-(S)-4-fluoro-2-methyl-phenyl)-piperazine-1-carboxylic acid tert-butyl ester (58 a Enantiomer A)

4-[2-(3,5-Bis-trifluoromethyl-phenyl)-pyrrolidine-1-carbonyl]-3-(S)-(4-fluoro-2-methyl-phenyl)-piperazine-1-carboxylic acid tert-butyl ester (58 b Enantiomer B)

A solution of triphosgene (47 mg) in DCM (2 mL) was added drop-wise to a solution of intermediate 54(103 mg) and TEA (97 µL) in acetonitrile (3 mL) previously cooled to 0° C. under a nitrogen atmosphere. The solution was stirred at r.t. for 2 hr. then intermediate 56 (103 mg) was added and the solution was heated to reflux for 5 hrs. After cooling to r.t., the solution was diluted with water and extracted with AcOEt. The organic layer was was dried, concentrated in vacuo and the residue was purified by flash chromatography (CH/AcOEt from 8:2 to 7:3) to give the title compound 58a (15 mg) and the title compound 58b (20 mg).

Intermediate 59

2-(3,5-Bis-trifluoromethyl-phenyl)-pent-4-enoic acid

Butyl lithium (1.6 M in hexane—1.7 mL) was added to a solution of diisopropylamine (4.88 g) in dry THF (40 mL) previously cooled to −78° C. under a nitrogen atmosphere. The solution was allowed to warm to 0° C. and stirred at this temperature for 1 h. Next, the solution was cooled to −78° C. and a solution of 3,5-(bis-trifluoromethyl)-phenylacetic acid (3 g) in THF (10 mL) was added. The solution was allowed to warm to 0° C. and stirred at this temperature for 2 h. The solution was cooled again to −78° C. and 2-propenyl iodide (1.2 mL) was added. The solution was allowed to warm to r.t. and stirred at r.t. for 3 hrs. The solution was quenched with 5N HCl until pH=2 and extracted with AcOEt. The organic layer was dried, concentrated in vacuo and the residue was purified by flash chromatography (CH/AcOEt 75:25) to give the title compound (2.4 g) as yellow oil.

Intermediates 60

4-[-(3,5-Bis-trifluoromethyl-phenyl)-but-3-enylcarbamoyl]-3-(S)-(4-fluoro-2-methyl-phenyl)-piperazine-1-carboxylic acid tert-butyl ester (60a enantiomer A)

4-[1-(3,5-Bis-trifluoromethyl-phenyl)-but-3-enylcarbamoyl]-3-(S)-(4-fluoro-2-methyl-phenyl)-piperazine-1-carboxylic acid tert-butyl ester (60b enantiomer B)

TEA (885 µL) and diphenyphosphorylazide (1.3 g) were added to a solution of intermediate 59 (500 mg) in dry toluene (25 mL) previously cooled to 0° C. under a nitrogen atmosphere. The solution was stirred at r.t. for 3 hr. then 54 (521 mg) was added and the mixture was heated to 100° C. for 1 hr. The mixture was allowed to cool to r.t. and partitioned between water and AcOEt. The organic layer was dried, concentrated in vacuo and the residue was purified by flash chromatography (CH/AcOEt from 8:2 to 7:3) to give the title compound 60a (480 mg) and the title compound 60b (450 mg) as white foams.

Intermediate 60a NMR (DMSO) δ (ppm) 7.94 (s, 2H); 7.84 (s, 1H); 7.14 (t, 1H); 6.94 (dd, 1H), 6.84 (dt, 1H); 6.66 (d, 1H); 5.62 (m, 1H); 5.18 (t, 1H); 5.0–4.9 (m, 2H), 4.84 (m, 1H); 3.82 (dt, 1H); 3.75 (m, 1H); 3.65 (bd, 1H); 3.43 (bt, 1H); 3.52 (dd, 1H); 3.17 (m, 1H); 2.45 (t, 2H), 2.24 (s, 3H); 1.29 (m, 1H).

Intermediate 60b NMR (DMSO) δ (ppm) 7.84 (s, 2H); 7.81 (s, 1H); 7.14 (t, 1H); 6.97 (dd, 1H), 6.86 (dt, 1H); 6.53 (bd, 1H); 5.66 (m, 1H); 5.15 (t, 1H); 5.05–4.9 (m, 3H), 3.89 (dt, 1H); 3.75–3.65 (b, 1H); 3.63 (bd, 1H); 3.52 (dd, 1H); 3.43 (dt, 1H); 3.2 (m, 1H); 2.5 (t, 2H), 2.3 (s, 3H); 1.28 (m, 1H).

Intermediate 61

4-{2-propenyl-[1-(3,5-Bis-trifluoromethyl-phenyl)-but-3-enyl-carbamoyl}-3-(S)-(4-fluoro-2-methyl-phenyl)-piperazine-1-carboxylic acid tert-butyl ester (enantiomer A)

Sodium tert-butoxide (245 mg) was added to a solution of intermediate 60a (480 mg) in dry THF (20 mL). The solution was stirred at r.t. for 10 min., then 2-propenyl iodide (400 µL) was added and stirring was continued for 3 h. The mixture was partitioned between water and AcOEt. The organic layer was dried and concentrated in vacuo to give the title compound as colourless oil (540 mg).

NMR (DMSO) δ (ppm) 7.94 (s, 1H); 7.79 (s, 2H); 7.28 (dd, 1H); 6.98 (dd, 1H), 6.84 (dt, 1H); 5.63 (m, 1H); 5.46 (m, 1H); 5.18 (t, 1H); 5.14–4.9 (m, 4H), 4.4 (bd, 1H); 3.98 (dd, 1H); 3.86 (dd, 1H); 3.7–3.55 (m, 2H); 3.4–2.7 (m, 4H); 2.32 (s, 3H), 1.36 (s, 9H).

Intermediate 62

4-[2-(3,5-Bis-trifluoromethyl-phenyl)-3,6-dihydro-2H-pyridine-1-carbonyl]-3-(S)-(4-fluoro-2-methyl-phenyl)-piperazine-1-carboxylic acid tert-butyl ester (enantiomer A)

Benzylidene bis(tricyclohexylphosphine) dichlororuthenium (34 mg) was added to a solution of intermediate 61 (540 mg) in dry DCM (20 mL) under a nitrogen atmosphere. The solution was stirred at r.t. for 4 hrs, then it was diluted with a saturated ammonium chloride solution and extracted with AcOEt. The organic layer was dried, concentrated in vacuo and the residue was purified by flash chromatography (CH/AcOEt 75:25) to give the title compound (0.35 g) as a brown oil.

NMR (DMSO) δ (ppm) 7.87 (s, 1H); 7.74 (s, 2H); 7.29 (dd, 1H); 6.93 (dd, 1H), 6.81 (dt, 1H); 5.8–5.6 (m, 2H); 5.2–4.9 (m, 4H); 4.7 (t, 1H); 4.46 (bs, 1H); 4.0–2.73 (m, 10H); 2.31 (s, 3H), 1.38 (s, 9H).

Intermediate 63

1-(Tert-Butoxycarbonyl)-3-(4-fluoro-2-methyl-phenyl)-piperazine

Di-tert-butyldicarbonate (271 mg) was added to a solution of intermediate 7 (301 mg) and TEA (315 μL) in DCM (10 mL) previously cooled to 0° C. under a nitrogen atmosphere. The solution was stirred at 0° C. for 40 min., then concentrated in vacuo. The residue was partitioned between water and AcOEt. The organic layer was washed with brine, dried and concentrated in vacuo. The residue was purified by flash chromatography (CH/AcOEt 6:4) to give the title compound (80 mg) as a colourless gum.

NMR (d₆DMSO): δ (ppm) 7.52 (m, 1H); 7.07–6.98 (m, 2H); 3.94–3.74 (m, 3H); 3.0–2.5 (m, 4H); 2.33 (s, 3H); 1.4 (s, 9H).

Intermediate 64

4-{[1-(3,5-Bis-trifluoromethyl-phenyl)-but-3-enyl]-carbamoyl}-3-(4-fluoro-2-methyl-phenyl)-piperazine-1-carboxylic acid tert-butyl ester (64a diastereoisomer A)

4-[1-(3,5-Bis-trifluoromethyl-phenyl)-but-3-enylcarbamoyl]-3-(4-fluoro-2-methyl-phenyl)-piperazine-1-carboxylic acid tert-butyl ester (64b diastereoisomer B)

TEA (700 μL) and diphenyphosphorylazide (812 μL) were added to a solution of intermediate 59 (400 mg) in dry toluene (20 ml) previously cooled to 0° C. under a nitrogen atmosphere. The solution was stirred at r.t. for 3 hr, then 400 mg of intermediate 63 was added and the mixture was heated to 100° C. for 1 hr. The mixture was allowed to cool to r.t. and partitioned between water and AcOEt. The organic layer was dried, concentrated in vacuo and the residue was purified by flash chromatography (CH/AcOEt 8:2) to give the title compound 64a (340 mg and the title compound 64b (250 mg ).

Intermediate 64a NMR (DMSO) δ (ppm) 7.94 (s, 2H); 7.84 (s, 1H); 7.14 (t, 1H); 6.94 (dd, 1H), 6.84 (dt, 1H); 6.66 (d, 1H); 5.62 (m, 1H); 5.18 (t, 1H); 5.0–4.9 (m, 2H), 4.84 (m, 1H); 3.82 (dt, 1H); 3.75 (m, 1H); 3.65 (bd, 1H); 3.43 (bt, 1H); 3.52 (dd, 1H); 3.17 (m, 1H); 2.45 (t. 2H), 2.24 (s,3H); 1.29 (m, 1H).

Intermediate 64b NMR (DMSO) δ (ppm) 7.84 (s, 2H); 7.81 (s, 1H); 7.14 (t, 1H); 6.97 (dd, 1H), 6.86 (dt, 1H); 6.53 (bd, 1H); 5.66 (m, 1H); 5.15 (t, 1H); 5.05–4.9 (m, 3H), 3.89 (dt, 1H); 3.75–3.65 (b, 1H); 3.63 (bd, 1H); 3.52 (dd, ₁H); 3.43 (dt, ₁H); 3.2 (m, 1H); 2.5 (t, 2H), 2.3 (s, 3H); 1.28 (m, 1H).

Intermediate 65

4-{[1-(3,5-Bis-trifluoromethyl-phenyl)-but-3-enyl]-methyl-carbamoyl}-3-(4-fluoro-2-methyl-phenyl)-piperazine-1-carboxylic acid tert-butyl ester (diastereoisomer A)

Sodium tert-butoxide (28 mg) was added to a solution of intermediate 64a (70 mg) in dry THF (10 mL). The solution was stirred at r.t. for 30 min., then methyl iodide (37 μL) was added. Reaction was slow, thus further amount of sodium tert-butoxide (28 mg) and methyl iodide (37 μL) were added (2×) and stirring was continued for 18 h. The mixture was partitioned between water and AcOEt. The organic layer was dried, concentrated in vacuo and the residue was purified by flash chromatography (CH/AcOEt 8:2) to give the title compound as colourless oil (44 mg).

NMR (DMSO) δ (ppm) 7.91 (bs, 1H); 7.68 (bs, 2H); 7.22 (dd, 1H); 6.94 (dd, 1H), 6.78 (dt, 1H); 5.72 (m, 1H); 5.34 (dd, 1H); 5.2–5.06 (2m, 2H), 4.41 (dd, 1H); 3.69 (m, 1H); 3.3–2.75 (m, 9H); 2.32 (s, 3H), 1.4 (s, 9H).

Intermediate 66

4-{Methyl-[1-(3,5-Bis-trifluoromethyl-phenyl)-but-3-enyl]-carbamoyl}-3-(4-fluoro-2-methyl-phenyl)-piperazine-1-carboxylic acid tert-butyl ester (diastereoisomer B)

Sodium tert-butoxide (28 mg) was added to a solution of intermediate 64b (70 mg) in dry THF (10 mL). The solution was stirred at r.t. for 30 min., then methyl iodide (37 μL) was added. Reaction was slow, thus further amount of sodium tert-butoxide (28 mg) and methyl iodide (37 μL) were added (2×) and stirring was continued for 18 h. The mixture was partitioned between water and AcOEt. The organic layer was dried, concentrated in vacuo and the residue was purified by flash chromatography (CH/AcOEt 8:2) to give the title compound as colourless oil (44 mg).

NMR (DMSO) δ (ppm) 7.91 (bs, 1H); 7.81 (bs, 2H); 7.25 (m, 1H); 6.94 (m, 1H), 6.84 (m, 1H); 5.62 (m, 1H); 5.14–4.94 (m, 2H); 5.11 (t, 1H); 4.46 (m, 1H); 3.7 (dd, 2H); 3.65–3.32 (m, 2H); 3.3 (m, 1H); 3.0 (m, 1H); 2.76 (m, 2H); 2.76 (s, 3H), 2.31 (s, 3H); 1.39 (s, 9H).

Intermediate 67

4-{2-propenyl-[1-(3,5-Bis-trifluoromethyl-phenyl)-but-3-enyl]-carbamoyl}-3-(4-fluoro-2-methyl-phenyl)-piperazine-1-carboxylic acid tert-butyl ester (diastereoisomer A)

Sodium tert-butoxide (113 mg) was added to a solution of intermediate 64 a (220 mg) in dry THF (15 mL). The solution was stirred at r.t. for 10 min., then 2-propenyl iodide (186 μL) was added and stirring was continued for 3 h. The mixture was partitioned between water and AcOEt. The organic layer was dried and concentrated in vacuo to give the title compound as colourless oil (180 mg).

NMR (DMSO) δ (ppm) 7.94 (s, 1H); 7.78 (s, 2H); 7.27 (dd, 1H); 6.97 (dd, 1H), 6.84 (dt, 1H); 5.62 (m, 1H); 5.45 (m, 1H); 5.17 (t, 1H); 5.08 (d, 1H); 5.04 (d, 1H); 4.99 (d, 1H), 4.93 (d, 1H); 4.38 (m, 1H); 3.95 (m, 1H); 3.85 (dd, 1H); 3.61 (m, 2H); 3.34 (m, 2H); 3.08 (m, 2H); 2.66 (m, 2H); 2.31 (s, 3H), 1.35 (s, 9H).

Intermediate 68

4-[2-(3,5-Bis-trifluoromethyl-phenyl)-3,6-dihydro-2H-pyridine-1-carbonyl]-3-(4-fluoro-2-methyl-phenyl)-piperazine-1-carboxylic acid tert-butyl ester (diastereoisomer A)

Benzylidene bis(tricyclohexylphosphine) dichlororuthenium (5% in mol 7.7 mg) was added to a solution of intermediate 67 (120 mg) in dry DCM (5 mL) under a nitrogen atmosphere. The solution was stirred at r.t. for 4 hrs, then it was diluted with a saturated ammonium chloride solution and extracted with AcOEt. The organic layer was dried, concentrated in vacuo and the residue was purified by flash chromatography (CH/AcOEt 7:3) to give the title compound (89 g) as a brown oil.

NMR (DMSO) δ (ppm) 7.9 (s, 1H); 7.69 (s, 2H); 7.26 (dd, 1H); 6.95 (dd, 1H), 6.82 (dt, 1H); 5.89 (m, 1H); 5.68 (bd, 1H); 5.28 (d, 1H); 4.49 (dd, 4H); 4.2 (d, 1H); 3.69 (dd, 1H); 3.64 (m 1H); 3.32 (m, 2H); 3.31 (m, 1H); 3.1 (m, 1H); 2.7 (bd, 1H); 2.53 (m, 1H); 2.3 (s, 3H), 1.37 (s, 9H).

Intermediate 69

2-(3,5-Bis-trifluoromethyl-phenyl)-2-methyl-propionic acid methyl ester (Trimethylsilyl)diazomethane (2M in hexane—3.68 mL) was added drop-wise to a solution of (3,5-bis-trifluoromethyl-phenyl)-acetic acid (500 mg) and dry methanol (82 µL) in dry toluene (8 mL) at 0° C., under a nitrogen atmosphere. The reaction mixture was stirred at 0° C. for 5 minutes, then the solvent was evaporated in vacuo to obtain the (3,5-bis-trifluoromethyl-phenyl)-acetic acid, methyl ester a pale yellow oil (440 mg). This material was dissolved in dry THF (4.5 mL) at 0° C., under nitrogen atmosphere and sodium bis(trimethylsilyl) amide (1.0M in THF—4 mL) was added dropwise. After ten minutes, methyl iodide (958 µL) was added and the reaction mixture was stirred at r.t. for 2 hours. The reaction was quenched with a 2N hydrochloric acid solution (7 mL) and the product was extracted with diethyl ether (2×10 mL). The combined organic extracts were dried and concentrated in vacuo to a residue which was purified by flash chromatography (CH/AcOEt 95:5) to give the title compound (184 mg) as a colourless oil.

NMR ($d_6$-DMSO): δ (ppm) 8.05 (s, 1H); 7.9 (s, 2H); 3.6 (s, 3H); 1.6 (s, 6H).

Intermediate 70

2-(3,5-Bis-trifluoromethyl-phenyl)-2-methyl-propionic acid

A solution of 2-(3,5-bis-trifluoromethyl-phenyl)-2-methyl-propionic acid, methyl ester (intermediate 69–184 mg) and potassium hydroxide (131 mg) in MeOH (2.5 mL) was heated to reflux for 1 hour, then it was allowed to cool to r.t. and acidified to pH=3 with 10% hydrochloric acid solution and extracted with AcOEt (2×10 mL). The combined organic extracts were dried and concentrated in vacuo to a residue which was purified by flash chromatography (CH/AcOEt from 8:2 to 6:4) to give the title compound (141 mg) as a white solid.

NMR ($d_6$-DMSO): δ (ppm) 8.05 (s, 1H); 7.9 (s, 2H); 1.6 (s, 6H).

Intermediate 71

1-(Benzyloxycarbonyl)-3-(S)-(4-fluoro-2-methyl-phenyl)-piperazine

Borane THF (23,16 mL) was added to a solution of intermediate 39 (964 mg) in dry THF (3 mL) previously cooled to 0° C. under a nitrogen atmosphere. The mixture was heated to 80° C. for 4 hrs. MeOH (4 mL) was added and the mixture was concentrated in vacuo. The residue was treated with HCl in $Et_2O$ (38 mL) and the solution was heated to 45° C. for 1 hr. The mixture was filtered to give 2-(S)-(4-fluoro-2-methyl-phenyl)-piperazine dihydrochloride (944 mg).

A solution of benzylchloroformate (376 µL) in dry DCM (20 mL) was added drop-wise to a solution of the 2-(S)-(4-fluoro-2-methyl-phenyl)-piperazine dihydrochloride (700 mg) and TEA (1.1 mL) in DCM (30 mL) previously cooled to 0° C. under a nitrogen atmosphere. The mixture was stirred at r.t. for 2 hrs, then washed with brine. The organic layer was dried, concentrated in vacuo and the residue was purified by flash chromatography (from CH/AcOEt 1:1 to AcOEt 100%) to give the title compound (750 mg) as colourless oil.

NMR ($d_6$-DMSO): δ (ppm) 7.51 (dd, 1H); 7.36–7.28 (m, 5H); 6.95 (m, 2H); 5.1 (dd, 2H); 3.92 (m, 2H); 3.74 (dd, 1H); 2.95 (dd, 1H); 2.91 (dt, 1H); 2.72 (dt, 1H); 2.62 (t, 1H); 2.29 (s, 3H).

Intermediate 72

4-[1-(3,5-Bis-trifluoromethyl-phenyl)-1-methyl-ethylcarbamoyl]-3-(S)-(4-fluoro-2-methyl-phenyl)-piperazine-1-carboxylic acid benzyl ester TEA (145 µL) and diphenyphosphorylazide (169 µL) were added to a solution of intermediate 70 (96 mg) in dry toluene (1.5 mL) previously cooled to 0° C. under a nitrogen atmosphere. The solution was stirred at r.t. for 3 hr, intermediate 71 (96 mg) was added and the mixture was heated to 100° C. for 1 hr. The mixture was allowed to cool to r.t. and partitioned between water and AcOEt. The organic layer was dried, concentrated in vacuo and the residue was purified by flash chromatography (CH/AcOEt 7:3) to give the title compound (140 mg) as a pale yellow gum.

NMR ($d_6$-DMSO): δ (ppm) 7.8 (s, 2H); 7.78 (s, 1H); 7.38–7.22 (m, 5H); 7.21 (dd, 1H); 6.95 (dd, 1H); 6.84 (dt, 1H); 6.52 (s, 1H); 5.18 (t, 1H); 5.05 (s, 2H); 3.89 (dt, 1H); 3.79 (dd, 1H); 3.72 (dt, 1H); 3.57 (dd, 1H); 3.44 (dt, 1H); 3.28 (bt, 1H); 2.23 (s, 3H); 1.55 (s, 3H); 1.5 (s, 3H).

MS: m/z=626[MH]$^+$.

Intermediate 73

4-{[1-(3,5-Bis-trifluoromethyl-phenyl)-1-methyl-ethyl]-methyl-carbamoyl]}-3-(S)4-fluoro-2-methyl-phenyl)-piperazine-1-carboxylic acid benzyl ester Sodium tert-butoxide (53 mg) was added to a solution of intermediate 72 (140 mg) in dry THF (1.5 mL). The solution was stirred at r.t. for 30 min., then methyl iodide (69 µL) was added and stirring was continued for 18 hrs. Further sodium tert-butoxide (42 mg) and methyl iodide (140 µL) were added and the mixture was heated to 70° C. for 3 hrs and then allowed to stir at r.t. for 18 hrs. The mixture was partitioned between water and AcOEt (2×10 mL). The organic layer was dried, concentrated in vacuo and the residue was purified by flash chromatography (CH/AcOEt 9:1) to give the title compound as colourless gum (58 mg).

NMR ($d_6$-DMSO): δ (ppm) 7.81 (s, 2H); 7.78 (s, 1H); 7.32–7.25 (m, 6H); 6.9 (dd, 1H); 6.85 (td, 1H); 5.08 (s, 2H); 4.64 (dd, 1H); 3.58 (m, 3H); 3.43 (m, 3H); 3.0 (s, 3H); 2.18 (s, 3H); 1.57 (s, 3H); 1.51 (s, 3H).

MS: m/z=640[MH]$^+$.

Intermediate 74

2-(3,5-Bis-trifluoromethyl-phenyl)-3-methyl-butyric acid methyl ester

Sodium bis(trimethylsilyl) amide (1.0M in THF—177 µL) was added drop-wise to a solution of (3,5-bis-trifluoromethyl-phenyl)-acetic acid methyl ester (389 mg) in dry THF (2 mL) at 0° C., under nitrogen atmosphere. After ten minutes, isopropyl iodide (143 μL) was added and the reaction mixture was stirred at 0° C. for 30 min. Further isopropyl iodide (143 μL) was added and the solution stirred at r.t. for 1 hour. The reaction was quenched with a 2N hydrochloric acid solution (2 mL) and the product was extracted with Et$_2$O (2×). The combined organic extracts were dried and concentrated in vacuo to a residue which was purified by flash chromatography (CH/AcOEt 95:5) to give the title compound (184 mg) as a colourless oil.

NMR (d$_6$-DMSO): δ (ppm) 8.05 (bs; 3H); 3.76 (d, 1H); 3.67 (s, 3H); 2.33. (m, 1H); 1.01 (d, 3H); 0.69 (d, 3H).

MS: m/z=328[M]$^+$.

Intermediate 75

2-(3,5-Bis-trifluoromethyl-phenyl)-3-methyl-butyric acid

A solution of intermediate 74 (280 mg) and potassium hydroxide (191 mg) in MeOH (4 mL) was heated to reflux for 1 hour, then it was allowed to cool to r.t. and acidified to pH=3 with 10% hydrochloric acid solution and extracted with AcOEt (2×10 mL). The combined organic extracts were dried and concentrated in vacuo to give the title compound (250 mg) as a white solid.

NMR (d$_6$-DMSO): δ (ppm) 8.05 (bs, 3H); 3.76 (d, 1H); 2.32 (m, 1H); 1.01 (d, 3H); 0.65 (d, 3H).

Intermediate 76

4-[1-(3,5-Bis-trifluoromethyl-phenyl)-2-methyl-propylcarbamoyl]-3-(4-fluoro-2-methyl-phenyl)-piperazine-1-carboxylic acid tert-butyl ester TEA (133 μL) and diphenyphosphorylazide (156 μL) were added to a solution of intermediate 75 (78 mg) in dry toluene (1 mL) previously cooled to 0° C. under a nitrogen atmosphere. The solution was stirred at r.t. for 3 hr, then intermediate 63 (80 mg) was added and the mixture was heated to 100° C. for 2 hr. The mixture was allowed to cool to r.t. and partitioned between water and AcOEt. The organic layer was dried, concentrated in vacuo and the residue was purified by flash chromatography (CH/THF 7:3) to give the title compound (140 mg) as a yellow gum.

IR (nujol) 3400 (NH), 1699 (C=O) cm$^{-1}$.

NMR (d$_6$-DMSO): δ (ppm) 7.93 (s, 1H+1H); 7.84 (s, 2H); 7.78 (s, 2H); 7.13 (dd, 1H+1H); 6.95 (dd, 1H+1H); 6.83 (m, 1H+1H); 6.51 (d, 1H); 6.41 (d, 1H); 5.2 (t, 1H); 5.16 (t, 1H); 4.57 (t, 1H); 4.48 (t, 1H); 3.9–3.17 (m, 6H+6H); 2.3 (s, 3H); 2.24 (s, 3H); 2.0–1.96 (m, 1H+1H); 1.28–1.27 (d, 9H+9H); 0.87 (d, 3H); 0.74 (d, 3H); 0.64 (d, 3H); 0.62 (d, 3H).

MS: m/z=606[MH]$^+$.

Intermediate 77

4-{[1-(3,5-Bis-trifluoromethyl-phenyl)-2-methyl-propyl]-methyl-carbamoyl]}-3-(4-fluoro-2-methyl-phenyl)-piperazine-1-carboxylic acid tert-butyl ester (77a diastereoisomer A)

4-{[1-(3,5-Bis-trifluoromethyl-phenyl)-2-methyl-propyl]-methyl-carbamoyl]}-3(4-fluoro-2-methyl-phenyl)-piperazine-1-carboxylic acid tert-butyl ester (77b diastereoisomer B)

Sodium tert-butoxide (55 mg) was added to a solution of intermediate 76 (140 mg) in dry THF (1.5 mL). The solution was stirred at r.t. for 30 min., then methyl iodide (72 μL) was added and stirring was continued for 18 hrs. Further sodium tert-butoxide (55 mg) and methyl iodide (72 μL) were added and the mixture was stirred at r.t. for 3 hrs. The mixture was partitioned between water and AcOEt (2×). The organic layer was dried, concentrated in vacuo and the residue was purified by flash chromatography (CH/AcOEt 9:1) to give the title compound 77a (35 mg) and the title compound 77 b (37 mg) as colourless gum.

Intermediate 77 a: T.l.c.: CH/AcOEt 8:2 Rf=0.62

NMR (d$_6$-DMSO): δ (ppm) 8.0 (s, 1H); 7.91 (bs, 2H); 7.21 (m, 1H); 6.95–6.83 (m, 2H); 4.65 (bm, 1H); 4.25 (bm, 1H); 3.68 (m, 2H); 3.25–2.81 (m+m+s, 7H); 2.32 (s, 3H); 1.38 (s, 9H); 0.68 (d, 3H); 0.64 (d, 3H).

MS: m/z=620[MH]$^+$.

Intermediate 77b: T.l.c.: CH/AcOEt 8:2 Rf=0.62

T.l.c.: CH/AcOEt 8:2 Rf=0.73

NMR (d$_6$-DMSO): δ (ppm) 7.96 (bs, 1H); 7.79 (bs, 2H); 6.99 (m, 1H); 6.93 (m, 1H); 6.6 (m, 1H); 4.87 (d, 1H); 4.27 (m, 1H); 3.7–3.2 (bm+bm+s+s, 10H); 1.39 (s, 9H); 0.88 (d, 3H); 0.73 (d, 3H).

MS: m/z=620[MH]$^+$.

Intermediate 78

(3,5-Bis-trifluoromethyl-benzylidene)-methylamine

A solution of 3,5-bis(trifluoromethyl)-benzaldehyde (412 μL) in dry THF (5 mL) was added dropwise to a solution of methylamine (2M in MeOH—3.12 mL) in dry THF (5 mL) at 23° C. under a nitrogen atmosphere. The reaction mixture was stirred overnight, then the solvent was evaporated in vacuo to give the title compound (385 mg) as a colourless oil.

NMR (CDCl$_3$): δ (ppm) 8.4 (s, 1H); 8.2 (s, 2H); 7.9 (s, 1H); 3.6 (s, 3H).

Intermediate 79

[(3,5-Bistrifluoromethyl-phenyl)-cyclopropyl-methyl]-methylamine

A solution of cyclopropyl bromide (518 μL) in dry diethyl ether (15 mL) was added dropwise to magnesium turnings (186 mg) previously heated to 40° C. under a nitrogen atmosphere. The reaction mixture was refluxed for 2 hours, then allowed to cooled to r. t. and decanted from the excess of magnesium. The cyclopropyl magnesium bromide so obtained, was added to a suspension of copper iodide (614 mg) in dry THF (5 mL) previously cooled to −50° C. under a nitrogen atmosphere. The reaction mixture was stirred at −50° C. for 20 min, then the temperature was taken to −78° C. and boron trifluoride etherate (408 μL) was added. After 5 minutes, intermediate 78 (330 mg) was added dropwise and the reaction mixture was stirred at −50° C. for 3 hours. The reaction was quenched with a mixture of ammonia (30% in water—10 mL) and saturated ammonium chloride solution (10 mL), extracted with petroleum ether (2×20 mL) and concentrated in vacuo. Then, 1N hydrochloric acid solution was added until pH=3, the aqueous phase was washed with petroleum ether (2×20 mL), then basified with solid potassium hydroxide until pH=9. After extraction with AcOEt (2×20 mL), the organic layer was dried and concentrated in vacuo to give the title compound (126 mg) as a pale yellow oil.

NMR (d$_6$-DDMSO): δ (ppm) 8.03 (s, 2H); 7.94 (s, 1H); 2.96 (d, 1H); 2.4 (bs, 1H); 2.11 (s, 3H); 0.92 (m, 1H); 0.54 (m, 1H); 0.38 (m, 1H); 0.29 (t, 2).

MS (ES/+): m/z=298 [MH]$^+$

Intermediate 80

4-{[(3,5-Bis-trifluoromethyl-phenyl)-cyclopropyl-methyl[-methyl-carbamoyl}-3-(4-fluoro-2-methyl-phenyl)-piperazine-1-carboxylic acid tert-butyl ester (diastereoisomer A)

A solution of triphosgene (45 mg) in dry DCM (0.5 mL) was added drop-wise to a solution of intermediate 63 (100 mg) and TEA (95 µL) in dry DCM (1.5 mL) previously cooled to 0° C. under a nitrogen atmosphere. The reaction mixture was stirred at 0° C. for 2 hours, then, a solution of and DIPEA (237 µL) in dry acetonitrile (2 mL) was added. The reaction was heated to 70° C. in order to evaporate the DCM, then intermediate 79 (110 mg) was added and the reaction mixture was refluxed overnight. The mixture was diluted with AcOEt (10 mL), washed with a 2N hydrochloric acid solution (10 mL) and brine (10 mL), dried and concentrated in vaccuo to a residue, which was purified by flash chromatography (CH/AcOEt from 8:2 to 7:3) to yield the title compound (10 mg)

NMR ($d_6$-DDMSO): δ (ppm) 7.77 (s, 1H); 7.73 (s, 2H); 7.24 (m, 1H); 6.85 (m, 2H); 4.56 (d, 1H); 4.46 (bm, 1H); 3.94 (m, 2H); 3.23 (m, 2H); 3.05 (m, 2H); 2.96 (s, 3H); 2.4 (s, 3H); 1.47 (s, 9H); 1.25 (m, 1H); 0.84 (m, 1H); 0.43 (m, 2H); 0.18 (m, 1H).

Intermediate 81

(S)-3-(4-Fluoro-2-methyl-phenyl)-piperazine dihydrochloride

To a solution of intermediate 39 (60.35 g) in dry THF (180 ml), at 0–3° C., under $N_2$, $BH_3$.THF 1M/THF (1220 mL) was added dropwise. The solution was refluxed for 4 hours then cooled to 0–3° C. and methanol (240 mL) was added. The reaction mixture was heated to room temperature then it was concentrated to dryness. The residue was redissolved in methanol (603,5 mL), excess HCl 1N in $Et_2O$ (1207 mL) was added and the mixture was refluxed for 2 hours then cooled at 3° C. for 4 hours. The suspension was filtered to obtain a white solid that was washed with $Et_2O$ (60.35 mL) and dried to yield the title compound (72.02 g)

$^1$H-NMR (DDMSO) δ (ppm) 11.0–9.5 (b, 4H); 7.99–7.19 (dd-m, 3H); 4.96 (dd, 1H); 3.65–3.15 (m, 6H); 2.42 (s, 3H).

Intermediate 82

(R)-3,5-bis-trifluoromethyl-phenyl)-ethyl]-methyl-amine

To a solution of 3,5-bis-trifluoromethylacetophenone (300 g) in MeOH (1120 ml), a solution of methylamine 8M in EtOH (372 mL) was added dropwise during 15 min. at 25° C. under $N_2$. The mixture was stirred for 24 hrs at 25° C. under $N_2$. Then, $NaBH_4$ was portionwise added over 30 min (27.9 g) at 0° C. A second amount of $NaBH_4$ was added over 30 min (17.1 g) and the mixture stirred for further 1.5 hrs.

The mixture was concentrated by evaporating 600 mL of solvent under vacuum then it was slowly poured into a mixture of AcOEt (1500 mL )/$NH_4Cl$ sat (750 mL) and water (750 mL). The water phase was back-extracted with AcOEt (1500 mL). The combined organic phases were washed with Water/Brine (150 mL/150 mL) then evaporated to obtain 3,5-bis-trifluoromethyl-phenyl)ethyl]-methyl-amine (305 g) as a yellow oil To a solution of 3,5-bis-trifluoromethyl-phenyl)ethyl]-methyl-amine (245.6 g) in EtOAc (2380 mL), L(+) malic acid was added portionwise (118 g). The suspension was stirred for 2 hrs at 25° C. then 3 hrs at 0° C. The suspension was filtered and the cake was washed with EtOAc (240 mL). The solid was dried under vacuum obtaining crude L(+)malate3,5-bis-trifluoromethyl-phenyl)-ethyl]-methyl-amine (135.3 g) as a white solid which was suspended in Ethyl acetate (1760 mL) then heated to reflux till complete dissolution and then cooled at 25° C. The suspension was filtered, washed with Ethyl acetate (135 mL) then dried to obtain L(+)malate3,5-bis-trifluoromethyl-phenyl)-ethyl]-methyl-amine (128.59). The solid was stirred in a mixture of NaOH 10% v/v (720 mL) and Ethyl acetate (650 mL). Organic phase was washed with water (720 mL), then concentrated to yield the title compound (82.2 g ).

$^1$H-NMR (DDMSO) δ (ppm) 7.99 (s, 2H); 7.85 (s, 1H); 3.78 (q, 1H); 2.34 (s, 1H); 2.09 (s, 3H); 1.23 (d, 3H).

EXAMPLE 1

2-(4-Fluoro-2-methyl-phenyl)-piperazine-1carboxylic acid (3,5-bistrifluoromethyl-benzyl)-methyl-amide hydrochloride A solution of intermediate 13 (0.05 g) in EtOH (10 mL) was hydrogenated at atmospheric pressure for 3 hr, in the presence of 10% Pd/C (10 mg) as catalyst. The catalyst was filtered off and the solvent was evaporated. The crude residue dissolved in diethyl ether and then a 1M sol. of HCl in $Et_2O$ (0.1 mL) was added. The formed precipitate was filtered and washed with diethyl ether to obtain the title compound (0.02 g) as a white powder.

m.p. >220° C.

NMR (DDMSO) δ (ppm) 9.33 (bm, 1H), 9.18 (bm, 1H), 7.96 (s, 1H), 7.59 (s, 2H), 7.33 (dd, 1H), 6.99 (d, 1H), 6.85 (t, 1H), 4.63 (d, 1H), 4.53 (d, 1H), 4.37 (d, 1H), 3,52 (d, 1H), 3.4–3.2 (m, 2H), 3.25 (m, 1H), 3.04 (t, 1H), 3.0–2.8 (m, 1H), 2.93 (s, 3H), 2.38 (s, 3H).

IR (Nujol) ($cm^{-1}$) 3200, 1659

MS (m/z) 478[M–Cl]$^+$

EXAMPLE 2

2-(3-Isopropyl-phenyl)-piperazine-1-carboxylic acid (3,5-bis-trifluoromethyl-benzyl)-methyl-amide hydrochloride To a solution of intermediate 14 (0.353 g) in anh. EtOH (5.7 mL), at r.t., under $N_2$, Pd/C 10% (175 mg, 50% wt) was added. The black suspension was placed under an atmosphere of $H_2$ and was stirred for 3 hr. The catalyst was then filtered on Celite and the Celite cake was rinsed with EtOH. HCl 1.0M in $Et_2O$ was then added (1.13 mL). The solvent was evaporated and the oil obtained was triturated with $Et_2O$. The solid was filtered, rinsed with $Et_2O$ and dried under vacuum. The title compound was obtained as a grey solid (104 mg).

m.p. 77–80° C.

NMR ($CDCl_3$): δ (ppm) 8.95 (bs, 2H), 7.97 (s, 1H), 7.75 (s, 1H), 7.22–7.08 (m, 4H), 4.584.41 (2d, 2H), 4.50 (dd, 1H), 3.44 (m, 1H), 3.4–3.1 (m, 5H), 2.84 (s, 3H), 2.80 (m, 1H), 1.12 (d, 3H), 1.07 (d, 3H).

IR (Nujol) ($cm^{-1}$) 3437, 1653

MS (m/z) 488[M–Cl]$^+$

EXAMPLE 3

2-(2-Isopropyl-phenyl)-piperazine-1-carboxylic acid (3,5-bis-trifluoromethyl-benzyl)-methyl-amide hydrochloride To a solution of intermediate 15 (0.108 g) in anh. EtOH (2.0 mL), at r.t., under $N_2$, Pd/C 10% (20 mg, 20% wt) was added. The black suspension was placed under an atmosphere of $H_2$ and was stirred for 3 hr. The catalyst was then filtered on Celite and the Celite cake was rinsed with EtOH. HCl 1.0M in $Et_2O$ was then added (350 µL). The solvent was evaporated and the oil obtained was triturated with $Et_2O$. The solid was filtered, rinsed with $Et_2O$ and dried under vacuum. The title compound was obtained as a brown solid (29 mg).

m.p. 108–110° C.

NMR ($CDCl_3$): δ (ppm) 9.15 (bd, 1H), 8.92 (bd, 1H), 7.97 (s, 1H), 7.66 (s, 2H), 7.30 (m, 1H), 7.27 (m, 1H), 7.19 (dt, 1H), 7.03 (dt, 1H), 4.69 (dd, 1H), 4.55 (2d, 2H), 3,53 (m, 1H), 3.39 (m, 3H), 3.19 (bd, 1H), 3.04 (dt, 1H), 2.92 (m, 4H), 1.24 (d, 3H), 1.20 (d, 3H).

IR (Nujol) ($cm^-$) 3441, 1662.

MS (m/z) 489[M–Cl]$^+$.

EXAMPLE 4

2(4-Fluoro-3-methyl-phenyl)-piperazine-1-carboxylic acid (3,5-bis-trifluoromethyl-benzyl)-methyl-amide hydrochloride To a solution of intermediate 16 (0.226 g) in anh. EtOH (3.7 mL), at r.t., under $N_2$, Pd/C 10% (23 mg, 10% wt) was added. The black suspension was placed under an atmosphere of $H_2$ and stirred for 3 hr. The catalyst was then filtered on Celite and the Celite cake was rinsed with EtOH. HCl 1.0M in $Et_2O$ was then added (740 µL). The solvent was evaporated and the oil obtained was treated with $Et_2O$. The solid obtained was filtered, rinsed with $Et_2O$ and dried under vacuum to give the title compound as a white solid (112 mg).

m.p. 70–72° C.

NMR ($CDCl_3$): δ (ppm) 9.08 (m, 2H), 7.97 (s, 1H), 7.67 (s, 2H), 7.19 (m, 1H), 7.14 (m, 1H), 7.01 (t, 1H), 4.59 (d, 1H), 4.43 (m, 1H), 4.40 (d, 1H), 3.1–3.5 (m, 6H), 2.92 (s, 3H), 2.14 (s, 3H).

IR (Nujol) ($cm^{-1}$) 3406, 1653

MS (m/z) 478 [M–Cl]$^+$

EXAMPLE 5

2-(2,4-Difluoro-phenyl)-piperazine-1-carboxylic acid (3,5-bis-trifluoromethyl-benzyl)-methyl-amide hydrochloride To a solution of intermediate 17 (0.134 g) in anh. EtOH (2.0 mL), at r.t., under $N_2$, Pd/C 10% (27 mg, 20% wt) was added. The black suspension was placed under an atmosphere of $H_2$ and was stirred for 3 hr. The catalyst was then filtered on Celite and the Celite cake was rinsed with EtOH. HCl 1.0M in $Et_2O$ was then added (436 µL). The solvent was evaporated and the oil obtained was triturated with $Et_2O$. The solid was filtered, rinsed with $Et_2O$ and dried under vacuum. The title compound was obtained as a yellow solid (112 mg).

m.p. 220–230° C.

NMR ($CDCl_3$): δ (ppm) 9.08–9.3 (m, 2H), 7.97 (s, 1H), 7.62 (s, 2H), 7.44 (m, 1H), 7.18 (m, 1H), 6.95 (m, 1H), 4.65 (m , 1H), 4.34.65 (dd, 2H), 3.2–3.6 (m, 4H), 3.07 (m, 2H), 2.92 (s, 3H).

IR (Nujol) ($cm^{-1}$) 3400, 1656

MS (m/z) 482 [M–Cl]$^+$.

EXAMPLE 6

2-(4-Fluoro-2-methyl-phenyl)-piperazine-1-carboxylic acid (3,5-bis-trifluoromethyl-benzyl)-amide hydrochloride A solution of intermediate 18 (0.086 g) in EtOH (10ml) was hydrogenated at atmospheric pressure for 2 hr, in the presence of 10% Pd/C (20mg) as catalyst. The catalyst was filtered off and the solvent was evaporated. The crude residue dissolved in $Et_2O$ and then a 1M sol. of HCl in $Et_2O$ (0.1 ml) was added. The solvent was evaporated to obtain the title compound (0.05 g) as a white solid.

NMR (DMSO) δ (ppm) 9.06 (m, 1H), 8.88 (m, 1H), 7.91 (s, 1H), 7.77 (s, 2H), 7.42 (t, 1H), 7.22 (dd, 1H), 7.03 (m, 1H), 6.94 (t, 1H), 5.22 (t, 1H), 4.34 (m, 2H), 3.98 (m, 1H), 3.64 (m, 1H), 3.4–3.2 (m, 2H), 3.22 (m, 2H), 2.32 (s, 3H).

IR (Nujol) ($cm^{-1}$) 3360, 1645.

MS (m/z) 464 [M–Cl]$^+$.

EXAMPLE 7

(+)-2-(R)-(4-Fluoro-2-methyl-phenyl)-piperazine-1-carboxylic acid (3,5-bis-trifluoromethyl-benzyl)-methyl-amide hydrochloride A solution of intermediate 20a (0.120 g) in EtOH (5 mL) was hydrogenated at atmospheric pressure for 4 hr, in the presence of 10% Pd/C (25 mg). Then the catalyst was filtered off and the solvent was evaporated. The crude product was dissolved in $Et_2O$ and then a solution 1M of HCl in $Et_2O$ (0.3 mL) was added. Then the precipitate was filtered and washed with $Et_2O$ to obtain the title compound (0.057 g) as a white solid.

m.p.>220° C.

NMR (DMSO) δ (ppm) 9.11 (m, 1H); 8.83 (m, 1H); 7.96 (s, 1H); 7.59 (s, 2H); 7.34 (dd, 1H); 6.94 (dd, 1H); 6.86 (m, 1H); 4.65–4.35 (dd, 2H); 4.49 (m, 1H); 3.54 (m, 1H); 3.44–3.01(m, 4H); 2.93 (s, 3H); 2.90 (m, 1H); 2.38 (s, 3H).

MS (m/z) 479 [MH–Cl]$^+$ $[α]^D_{20}$=+69.5 C.=0.27(g/100 ml) $CHCl_3$

EXAMPLE 8

(−)-2-(S)-(4-Fluoro-2-methyl-phenyl)-piperazine-1-carboxylic acid (3,5-bis-trifluoromethyl-benzyl)-methyl-amide hydrochloride

Method A

A solution of intermediate 20b (0.110 g) in EtOH (5 mL) was hydrogenated at atmospheric pressure for 4 hr, in the presence of 10% Pd/C (25 mg). Then the catalyst was filtered off and the solvent was evaporated. The crude product was dissolved in $Et_2O$ and then a solution 1M of HCl in $Et_2O$ (0.3 mL) was added. Then the precipitate was filtered and washed with diethyl ether to obtain the title compound (0.045 g) as a white solid.

Method B

A solution of intermediate 37a (0.24 g) in EtOH (4 mL) was hydrogenated at atmospheric pressure for 3 hr. in the presence of 10% Pd/C (73 mg) as catalyst. The catalyst was filtered off and the solvent was evaporated. The crude residue was dissolved in $Et_2O$ and then a 1M sol. of HCl in $Et_2O$ (0.58 mL) was added. The formed precipitate was filtered and washed with diethyl ether to obtain the title compound (0.04 g) as a white powder.

Method C

To Intermediate 39 (2.37 g) TEA (3.15 mL) in dry DCM (57 mL) was added dropwise, at 0° C. Then a solution of triphosgene (1.502 g) in dry DCM (12 mL) under inert atmosphere was added. The temperature was maintained at 0° C. for 3 hr. before the addition of DIPEA (4 mL) followed by 3,5-bis-trifluoromethylbenzyl-N-methyl amine (4.62 g) in acetonitrile (142 mL). The reaction mixture was heated to reflux for 3 hr then cooled to room temperature diluted with DCM (25 mL) and washed with a 1N solution of HCl (25 mL), H₂O (25 mL) and brine (25 mL) in sequence. The organic phase was dried and the crude product obtained after evaporation of the solvent was purified by flash chromatography (from AcOEt/CH 4:1 to pure AcOEt) to give 2-(4-Fluoro-2-methyl-phenyl)-3-oxo-piperazine-1-carboxylic acid (3,5-bis-trifluoromethyl-benzyl)-methyl-amide as a foam (1.79 g).

This compound was reduced with BH₃.THF (17.6 mL) following the standard procedure (4 hr reflux in 10 ml of THF, then work-up with 6 mL of HCl 37% and subsequent neutralisation with 5 g of solid NaHCO₃) to give the title compound (1.16 g).

m.p.>220° C.

NMR (DMSO) δ (ppm) 9.11 (m, 1H); 8.83 (m, 1H); 7.96 (s, 1H); 7.59 (s, 2H); 7.34 (dd, 1H); 6.94 (dd, 1H); 6.86 (m, 1H); 4.65-4.35 (dd, 2H); 4.49 (m, 1H); 3.54 (m, 1H); 3.44–3.01(m, 4H); 2.93 (s, 3H); 2.90 (m, 1H); 2.38 (s, 3H).

MS (m/z) 479 [MH−Cl]⁺

$[\alpha]^D_{20}$=−72.6 C.=0.27 (g/100 ml) CHCl₃

EXAMPLE 9

2-(4-Fluoro-2-methyl-phenyl)-piperazine-1-carboxylic acid [1-(R)-(3,5-bis-trifluoromethyl-phenyl)ethyl]-methyl-amide hydrochloride A solution of intermediate 22a (0.05 g) in EtOH (5 mL) was hydrogenated at atmospheric pressure for 1½ hr. in the presence of 10% Pd/C (15 mg). Then the catalyst was filtered off and the solvent was evaporated. The crude product was dissolved in Et₂O and then a solution 1M of HCl in Et₂O (0.5 mL) was added. Then the precipitate was filtered and washed with Et₂O to obtain the title compound (0.025 g) as a white powder.

NMR (CDCl₃) δ (ppm) 10.2 (b, 1H); 7.78 (s, 1H); 7.54 (s, 2H); 7.13 (dd, 1H); 6.88 (dd, 1H); 6.82 (m, 1H); 5.48 (q, 1H); 4.57 (m, 1H); 3.6–3.5 (m, 2H); 3.38 (m, 2H); 3.3–3.0 (m, 2H); 2.71 (s, 3H); 2.48 (s, 3H); 1.44 (d, 3H).

IR (CDCl₃) 1663

MS (m/z) 491 [M−Cl]⁺

EXAMPLE 10

2-(4-Fluoro-2-methyl-phenyl)-piperazine-1-carboxylic acid [1-(S)-(3,5-bis-trifluoromethyl-phenyl)-ethyl]-methyl-amide hydrochloride A solution of intermediate 22b (0.05 g) in EtOH (5 mL) was hydrogenated at atmospheric pressure for 1½ hr. in the presence of 10% Pd/C (15 mg). Then the catalyst was filtered off and the solvent was evaporated. The crude product was dissolved in Et₂O and then a solution 1M of HCl in Et₂O (0.5 mL) was added. Then the precipitate was filtered and washed with Et₂O to the title compound (0.057 g) as a white powder.

NMR (CDCl₃) δ (ppm) 10.2 (b, 1H); 7.74 (s, 1H); 7.41 (s, 2H); 7.10 (m, 1H); 6.88 (m, 1H); 6.80 (m, 1H); 5.58 (q, 1H); 4.85 (m, 1H); 3.7–2.9 (m, 6H); 2.80 (s, 3H); 2.49 (s, 3H); 1.44 (d, 3H).

IR (CDCl₃) 1662

MS (m/z) 491 [M−Cl]⁺

EXAMPLE 11

2-(4-Fluoro-2-methyl-phenyl)-piperazine-1-carboxylic acid (3,5-bis-trifluoromethyl-benzyl)-methyl-amide To a solution of intermediate 32 (813 mg) in anh. THF (6.6 mL), at r.t., under N₂, BH₃-THF 1M in THF (9.9 mL) was added. The solution was heated at reflux for 3 hr. It was then brought back to r.t. and 1N HCl (4 mL) was added slowly in order to destroy the borane complexes. The reaction mixture was stirred at r.t. for 18 hr. The THF was evaporated and the aqueous phase was basified with 10% NaOH. It was then extracted with EtOAc (3×). The combined organic extracts were dried, the solids were filtered and the solvent evaporated. The title compound was used in the next step (790 mg) without any further purification.

NMR (CDCl₃): δ (ppm) 7.77 (s, 1H), 7.49 (s, 2H), 7.33 (m, 1H), 6.86 (m, 1H), 6.82 (m, 1H), 4.65–4.46 (2d (AB), 2H), 4.46 (m, 1H), 3.40–2.85 (m, 6H), 2.97 (s, 3H), 2.66 (s, 3H).

IR (CDCl₃, cm⁻¹): 1653.

MS (m/z): 478 [MH]⁺

EXAMPLE 12

2-(4-Fluoro-phenyl)-piperazine-1-carboxylic acid (3,4-bis-trifluoromethyl-benzyl)-methyl-amide hydrochloride A 1M solution of BH₃.in THF (1.88 mL) was added very carefully to a solution of intermediate 33 (0.180 g) in dry THF (8 mL) under inert atmosphere; and the reaction mixture was refluxed 3 hr. After completion of the reduction, HCl 37% was added (3 mL) and the reaction mixture was refluxed 2 hr. THF was removed under reduced pressure, water was added (3 mL) and the aqueous solution was basified using Na₂CO₃; next, it was extracted with DCM, washed with brine and dried. The crude product was purified by flash chromatography (AcOEt/MeOH 8:2) affording the free amine which was treated with a 1M solution of HCl in Et₂O (0.3 mL) to yield the title compound (0.05 g) as a white solid.

mp>200° C.

NMR (DMSO) δ (ppm): 9.08 (bs, 2H), 7.97 (s, 1H), 7.66 (s, 2H), 7.35 (m, 2H), 7.10 (m, 2H), 4.60 (d, 1H), 4.46 (dd, 1H), 4.39 (d, 1H), 3.50–3.10 (m, 6H), 2.92 (s, 3H).

IR (Nujol) (cm⁻¹) 3437, 1653

MS: 464 [M−Cl]⁺.

EXAMPLE 13

2-Phenyl-piperazine-1-carboxylic acid (3,5-bis-trifluoromethyl-benzyl)-methyl-amide hydrochloride To a stirred solution of intermediate 34 (0.382 g) in THF (10 mL) a 1M solution of BH₃ in THF (1.66 mL) was added. The mixture was then refluxed for 3 hr. The temperature was then cooled, and the reaction was quenched with a solution of HCl 37% (5 mL) and stirred at room temperature overnight. The solution was then basified with NaOH and the product was extracted with DCM, dried and concentrated under reduced pressure to give an oil. The oil was then dissolved in Et₂O and a 1M solution of HCl in Et₂O (1.6 mL) was added. After a few minutes the solution was concentrated, and the product was triturated from petroleum ether to give the title compound (0.300 g) as a solid.

NMR(CDCl₃): δ (ppm): 10.15(b, 2H); 7.75(s, 1H); 7.44(s, 2H); 7.3(m, 5H); 4.80–4.34(m, 3H); 3.80–3.00(m, 6H); 2.93(s, 3H)

MS (m/z):446 [M−Cl]⁺.

EXAMPLE 14

2-(2,4-Dichloro-phenyl)-piperazine-1-carboxylic acid (3,5-bistrifluoro methyl-benzyl)-methyl-amide hydrochloride To a solution of intermediate 35 (0.22 g) in THF (15 mL) a 1M solution of borane in THF (1.2 mL) was added and the reaction mixture was stirred at reflux for 3 hr, then cooled to r.t. 37% HCl (3 mL) was added drop-wise and the reaction mixture stirred for 3 hr. The solvent was evaporated and the crude residue was diluted with AcOEt and washed with a saturated solution of NaHCO$_3$ and brine. The organic phase was dried and concentrated to give the crude product. The latter was dissolved in Et$_2$O (2ml), then a 1M sol of HCl in Et$_2$O (1 mL) was added. The obtained solution was added dropwise in petroleum (30 mL) and the formed precipitate was filtered to obtain the title compound (0.06 g, white solid).

NMR (DMSO) δ (ppm) 9.25, 9.15 (m+m, 2H), 7.98 (m, 1H), 7.64 (s, 2H), 7.60 (d, 1H), 7A45 (d, 1H), 7.29 (dd, 1H), 4.78 (dd, 1H), 4.63 (d, 1H), 4.35 (d, 1H), 3.59 (d, 1H), 3.40–3.25 (m, 3H), 3.07 (t, 3H), 2.95, 2.93 (s+m, 4H).

IR (Nujol) (cm$^{-1}$) 3442, 1654

MS (m/z) 515 [M–Cl]$^+$.

EXAMPLE 15

2-(3,4-Dichloro-phenyl)-piperazine-1-carboxylic acid (3,5-bistrifluoro methyl-benzyl)-methyl-amide hydrochloride To a solution of intermediate 36 (0.13 g) in THF (20 mL) a 1M solution of borane in THF (1.96 mL) was added and the reaction mixture was stirred at reflux for 3 hr, then cooled to r.t. 37% HCl (5 mL) was added drop-wise and the reaction mixture was stirred for 3 hr. The solvent was evaporated and the crude residue was diluted with AcOEt and washed with a saturated solution of NaHCO$_3$ and brine. The organic phase was dried and concentrated to give the crude product. The latter was dissolved in Et$_2$O (2 mL), then a 1M sol of HCl in diethyl ether (1 mL) was added. The obtained solution was added drop-wise in petroleum (30 mL) and the formed precipitate was filtered to obtain the title compound (0.016 g, white solid).

NMR (DMSO) δ (ppm) 8.99 (broad, 2H), 7.98 (s, 1H), 7.70 (s, 2H), 7.56 (d+d, 2H), 7.31 (dd, 1H), 4.58 (d, 1H), 4.50 (d, 1H), 4.41 (d, 1H), 3.5–3.1 (m, 4H), 2.93 (s, 3H).

IR (Nujol) (cm$^{-1}$) 3436, 1653

MS (m/z) 515 [M–Cl$^+$.

EXAMPLE 16

(–)-2-(S)-(4-Fluoro-2-methyl-phenyl)-piperazine-1-carboxylic acid [1-(S)-(3,5-bis-trifluoromethyl-phenyl)-ethyl]-methyl-amide hydrochloride A solution of intermediate 38a (0.08 g) in EtOH (5 mL) was hydrogenated at atmospheric pressure for 4 hr, in presence of 10% Pd/C (50 mg). The catalyst was filtered off and the solvent was evaporated. The crude product was dissolved in Et$_2$O and then a solution 1M of HCl in Et$_2$O (0.5 mL) was added. The precipitate was filtered and washed with Et$_2$O to obtain the title compound (0.023 g).

NMR (CDCl$_3$) δ (ppm) 10.5–10.0 (b, 2H); 7.74 (s, 1H); 7.41 (s, 2H); 7.09 (m, 1H); 6.88 (m, 1H); 6.80 (m, 1H); 5.58 (q, 1H); 4.85 (m, 1H); 3.80–3.00 (m, 6H); 2.80 (s, 3H); 2.49 (s, 3H); 1.53 (d, 3H).

MS (m/z) 492

$[α]^D{}_{20}$=–164.9, 0.12(g/100 ml) CHCl$_3$

EXAMPLE 17

(+)-2-(R)-(4-Fluoro-2-methyl-phenyl)-piperazine-1-carboxylic acid [1-(R)-(3,5-bis-trifluoromethyl-phenyl)ethyl]-methyl-amide hydrochloride A solution of intermediate 38 b (0.08 g) in EtOH (5 mL) was hydrogenated at atmospheric pressure for 4 hr, in presence of 10% Pd/C (50 mg). The catalyst was filtered off and the solvent was evaporated. The crude product was dissolved in Et$_2$O and then a solution 1M of HCl in Et$_2$O (0.5 ML) was added. The precipitate was filtered and washed with Et$_2$O to obtain the title compound (0.020 g).

NMR (CDCl$_3$) δ (ppm) 10.5–10.0 (b, 2H); 7.74 (s, 1H); 7.41 (s, 2H); 7.09 (m, 1H); 6.88 (m, 1H); 6.80 (m, 1H); 5.58 (q, 1H); 4.85 (m, 1H); 3.80–3.00 (m, 6H); 2.80 (s, 3H); 2.49 (s, 3H); 1.53 (d, 3H).

MS (m/z) 492

$[α]^D{}_{20}$=+207, 0.11 (g/100 ml) CHCl$_3$

EXAMPLE 18

2-(S)-(4-Fluoro-2-methyl-phenyl)-piperazine-1-carboxylic acid [1-(R)-(3,5-bis-trifluoromethyl-phenyl)-ethyl]-methyl-amide acetate salt To a solution of intermediate 40a (8.8 9) in dry THF (33 mL) under N$_2$ BH$_3$.THF (1M solution in THF—87 mL) was added and the reaction mixture was stirred at reflux for 3 hr, then cooled to r.t. and HCl (37%, 30 mL) was added drop-wise maintaining the reaction mixture in an icebath. The reaction mixture was stirred at r.t. for 1 hr. Water was then added (70 mL) and solid NaHCO$_3$ (35.2 g) was added portion-wise until a pH of 6.5. The THF was evaporated and the aqueous phase was extracted with Et$_2$O (3×88 mL). The combined organic phases were dried, and evaporated to leave a colourless oil (7.37 g).

This crude oil was purified by flash chromatography (AcOEt/MeOH 7:3). The product obtained was suspended in Et$_2$O (125 mL) and washed with NaHCO$_3$ sat. (2×20 mL). The clear combined organic phases were dried and evaporated to obtain the 2-(S)-(4-Fluoro-2-methyl-phenyl)-piperazine-1-carboxylic acid [1-(R)-(3,5-bis-trifluoromethyl-phenyl )-ethyl]-methyl-amide as white foam (5.27 g). This material (5.27 g) was dissolved in Et$_2$O (79 mL) and acetic acid (613 μL) was added drop-wise. The mixture was stirred at r.t. for 1 h and then at 0° C. for 1 h. The suspension was filtered to give the title compound (4.366 g) as a white solid.

NMR ($^1$H, DMSO-d$_6$): δ (ppm) 7.98 (s, 1H), 7.70 (s, 2H), 7.87 (m, 1H), 6.91 (m, 1H), 6.77 (m, 1H), 5.29 (q, 1H), 4.23 (dd, 1H), 3.2–2.6 (m, 6H), 2.68 (s, 3H), 2.3 (s, 3H), 1.89 (s, 3H), 1.48 (d, 3H).

MS (m/z): 492 [M–CH$_3$COO]$^+$.

$[α]^D$=–20.4° C. Solvent (CHCl3); Source: Na; Cell volume [mL]: 1; Cell pathlength [dm]: 1; Cell temperature [° C.]: 20; Wavelength [nm]: 589

EXAMPLE 19

2-(S)-(4-Fluoro-2-methyl-phenyl)-piperazine-1-carboxylic acid [1-(S)-(3,5-bis-trifluoromethyl-phenyl)-ethyl]-methyl-amide acetate To a solution of intermediate 40b (2.57 g) in dry THF (15.5 mL), at 0° C., under N$_2$, was added BH$_3$.THF (1M solution in THF) then heated at reflux for 3 hr. It was then brought back to r.t. and HCl 37% (9 mL) was added slowly maintaining the reaction mixture in an ice-bath. The reaction mixture was stirred at r.t. for 1 hr. Water was then added (20.5 mL) and solid NaHCO$_3$ (10.3 g) was added portion-wise until a pH of 7.

The THF was evaporated and the aqueous phase was extracted with Et$_2$O (3×25.7 mL). The combined organic phases were dried and evaporated to leave a yellow oil (2.34 g). This crude oil was dissolved in Et$_2$O (35 mL) and glacial ACOH (0.245 mL) was added dropwise. The mixture was stirred 2 hr at 0° C., then it was filtered, washed with Et$_2$O (10 mL) and dried under vacuum to obtain the title compound as a white solid (1 349 gr).

NMR ($^1$H. DMSOd$_6$): δ (ppm) 7.92 (s, 1H), 7.58 (s, 1H), 7.29 (m, 1H), 6.90 (m, 1H), 6.77 (m, 1H), 5.33 (q, 1H), 4.19 (m, 1H), 3.2–2.6 (m, 6H), 2.79 (s, 3H), 2.32 (s, 3H), 1.89 (s, 3H), 1.48 (d, 3H).

MS (m/z): 492 [M–CH$_3$COO]$^+$.

[α]$^D$=+2.2° C.

Solvent (CHCl3); Source:Na; Cell volume [mL]: 1; Cell pathlength [dm]: 1; Cell temperature [° C.]: 20; Wavelength [nm]: 589

EXAMPLE 20

4-(2-Amino-acetyl)-2-(S)-(4-fluoro-2-methyl-phenyl)-piperazine-1-carboxylic acid (3,5-bis-trifluoromethyl-benzyl)-methyl-amide hydrochloride Example 8 (0.05 g) was dissolved in dry DMF (2 mL), DIPEA (0.019 mL) was added and the solution thus obtained was added to a solution of N-(tert-butoxycarbonyl)glycine (0.0192 g), 1-(3dimethylaminopropyl)-3-ethylcarbodiimide (0.0214 g) and 1-hydroxybenzotriazole (0.015 g) in dry DMF (5 mL). The reaction mixture was stirred 18hr at room temperature, then diluted with AcOEt (30 mL), washed with water (30 mL), sodium bicarbonate (30 mL) and brine (30 mL). The separated organic layer was dried and evaporated to give a crude, which was purified by flash chromatography (AcOEt). The compound obtained (0.043 g) was dissolved in 1M solution of HCl in Et$_2$O (5 mL), stirred 0.5 hr at room temperature and evaporated to obtain the title compound (0.046 g) as a yellow foam.

NMR (DMSO) δ (ppm) 8.01 (bs, 3H), 7.88 (s, 1H), 7.67 (s, 2H), 7.33 (m, 1H), 6.95 (m, 1H), 6.83 (m, 1H), 4.60 (m, 1H), 4.604.42 (dd, 2H), 4.2–3.3 (m, 6H), 3.2 (m, 2H), 2.89 (s, 3H), 2.4 (s, 3H).

IR (Nujol) (cm$^{-1}$) 3410, 1660.

MS (m/z) 535 [M–Cl]$^+$.

EXAMPLE 21

2-(S)-(4-Fluoro-2-methyl-phenyl)-piperazine-1-carboxylic acid [1-(3,5-bis-trifluoromethyl-phenyl)-1-methyl-ethyl]-methyl-amide hydrochloride Palladium on charcoal (10%—17.5 mg) was added to a solution of intermediate 73 (145 mg) in ethanol (2 mL). The resulting mixture was stirred at 1 atm and r.t. under hydrogen atmosphere for 2 hrs. The mixture was filtered and concentrated in vacuo. The residue was dissolved in Et$_2$O (2 mL) and treated with HCl 1M in Et$_2$O (1 mL). the mixture was stirred at r.t. for 10 min, then concentrated in vacuo and the residue triturated with Et$_2$O/petroleum to give the title compound (27 mg) as white solid.

NMR (d$_6$-DMSO): δ (ppm) 9.15 (bs, 1H); 8.9 (bs, 1H); 7.77 (s, 1H); 7.71 (s, 2H); 7.31 (dd, 1H); 6.95–6.87 (m, 2H); 4.39 (dd, 1H); 3.71 (dt, 1H); 3.35–2.9 (m, 5H); 3.24 (s, 3H); 2.23 (s, 3H); 1.49 (s, 3H); 1.46 (s, 3H).

MS: m/z=506 [MH]$^+$.

EXAMPLE 22

4(2-Aminoethyl)-2-(S)-(4-fluoro-2-methyl-phenyl)-piperazine-1-carboxylic acid (3,5-bis-trifluoromethyl-benzyl)-methyl-amide dihydrochloride Salt To a solution of intermediate 41 (25 mg) in absolute EtOH (1 mL), at room temperature, was added methylamine 8.03M in EtOH (48 μL). The reaction mixture was stirred at r.t. for 5 hr. The solvent was evaporated and the crude product purified by flash chromatography (AcOEt/MeOH/NH$_4$OH conc. 90:5:5). The fractions were collected and the solvent was evaporated. The residue was dissolved in Et$_2$O and HCl 1.0M in Et$_2$O (150 μL) was added. The yellow precipitate was filtered and dried to give the title compound (19 mg) as a yellow solid.

NMR (DMSO) δ (ppm) 8.12 (bs, 2H), 7.90 (s, 1H), 7.62 (s, 2H), 7.33 (t, 1H), 6.95 (dd, 1H), 6.83 (td, 1H), 4.69 (m, 1H), 4.62 (d, 1H), 4.41 (d, 1H), 3.60–3.10 (m, 10H), 2.94 (s, 3H), 2.40 (s, 3H).

IR (Nujol) (cm$^{-1}$) 3433–3300, 1651.

MS (m/z) 521 [M-2HCl+H]$^+$.

EXAMPLE 23

2-(4-Fluoro-2-methyl-phenyl)-3-methyl-piperazine-1-carboxylic acid (3,5-bis-trifluoromethyl-benzyl)-methyl-amide hydrochloride salt To a solution of intermediate 45 (100 mg) in anh. MeOH (3 mL), under N$_2$, at room temperature, was added Pd/C 10% (20 mg). The reaction mixture was placed under an H$_2$ atmosphere and stirred at room temperature for 2 hr. The catalyst was filtered on Celite, and the Celite cake was rinsed with AcOEt. The solvent was evaporated and the residue was dissolved in Et$_2$O. HCl 1.0N in Et$_2$O (240 μl) was added and the white precipitate was filtered and rinsed with Et$_2$O. The title compound was obtained (73 mg) as a white solid.

NMR (CDCl$_3$) δ (ppm) 9.31+9.01 (m, 2H), 7.99 (s, 1H), 7.70 (s, 2H), 7.02 (m, 2H), 6.78 (m, 1H), 4.63 (d, 1H), 4.74.3 (dd, 2H), 3.66 (m, 1H), 3.5–2.9 (m, 4H), 3.05 (s, 3H), 2.34 (s, 3H), 1.09 (d, 3H).

IR (Film) (cm$^{-1}$) 1659.

MS (m/z) 692 [MH–Cl]$^+$.

EXAMPLE 24

2-(2-Methyl-4-fluoro-phenyl)-6-methyl-piperazine-1-carboxylic acid (3,5-bis-trifluoromethyl-benzyl)-methyl-amide hydrochloride salt BH$_3$.THF complex (1.25 mL) was added very carefully to a solution of intermediate 47 (0.080 g) in dry THF (5 mL) under inert atmosphere and the reaction mixture was refluxed for 3 hr. After completion of the reduction, HCl 37% was added (3 mL) and the reaction mixture was refluxed for 2 hr. THF was removed under reduced pressure, water was added (3 mL) and the aqueous solution was basified by means of Na$_2$CO$_3$, extracted with DCM, washed with brine and dried. The crude product was purified by flash chromatography (AcOEt/MeOH 8:2) to afford a product which was dissolved in Et$_2$O and treated with HCl 1.0M in Et$_2$O. (0.3 mL) to give the title compound (0.03 mg).

$^1$H-NMR (DMSO) δ (ppm) 9.12 (bs, 1H), 8.88 (bs, 1H), 7.93 (s, 1H), 7.56 (s, 2H), 7.37 (m, 1H), 6.74 (m, 2H), 4.71 (d, 1H), 4.35 (dd, 1H), 4.36–4.10 (bm, 1H), 3.35–2.9 (m, 5H), 2.99 (s, 3H), 2.28 (s, 3H), 1.05 (d, 3H).

MS (m/z) 492 [M–Cl]$^+$.

mp>200 ° C.

EXAMPLE 25

2-(S)-(4-Fluoro-2-methyl-phenyl)-piperazine-1-carboxylic acid [(1–3,5-bis-trifluoromethyl-phenyl)-cyclopropyl]-methyl-amide hydrochloride Conc. HCl (0.27 mL) was added to a solution of intermediate 53 (90 mg) in methanol (9 mL) and the mixture was refluxed for 15 min. The mixture was concentrated in vacuo and the residue triturated with Et$_2$O to give the title compound (32 mg) as white solid.

IR (nujol): 3405 (NH$_2$$^+$), 1653 (C=O) cm$^{-1}$.

NMR (DMSO) δ (ppm) 9.42 (bs, 1H); 9.27 (bs, 1H); 7.79 (bs, 1H), 7.45 (dd, 1H); 7.25 (bs, 2H); 6.94 (m, 2H), 4.52 (dd, 1H), 3.5–3.06 (m, 9H); 2.33 (s, 3H), 1.34 (m, 2H); 1.22 (m, 2H).

MS: m/z=504 [M−Cl]$^+$.

EXAMPLE 26

[2-(3,5-Bis-trifluoromethyl-phenyl)-pyrrolidin-1-yl]-[2-(S)-(4-fluoro-2-methyl-phenyl)-piperazin-1-yl]-methanone hydrochloride (enantiomer A)

Conc. HCl (0.3 mL) was added to a solution of intermediate 58a (15 mg) in methanol (5 mL) and the mixture was refluxed for 2 hrs. The mixture was concentrated in vacuo to give the title compound (7 mg) as white solid.

IR (nujol) 1654 (C=O) cm$^{-1}$.

NMR (DMSO) δ (ppm) 9.17 (bs, 1H); 8.88 (bs, 1H); 7.93 (s, 1H), 7.86 (s, 2H); 7.23 (m, 1H); 6.94 (m, 2H), 4.78 (t, 1H), 4.46 (dd, 1H); 3.88–3.83 (m, 2H); 3.79 (m, 1H); 3.4 (m, 1H); 3.28 (m, 1H); 3.2 (d, 1H); 3.06 (t, 1H); 2.84 (m, 1H); 2.31 (m, 1H), 2.27 (s, 3H); 1.96 (m, 1H); 1.74 (m, 1H); 1.62 (m, 1H).

MS: m/z=504 [MH−HCl]$^+$.

EXAMPLE 27

[2-(3,5-Bis-trifluoromethyl-phenyl)-pyrrolidin-1-yl]-[2-(S)-(4-fluoro-2-methyl-phenyl)-piperazin-1-yl]-methanone hydrochloride (enantiomer B)

Conc. HCl (0.3 mL) was added to a solution of intermediate 58b (20 mg) in methanol (5 mL) and the mixture was refluxed for 2 hrs. The mixture was concentrated in vacuo to give the title compound (11 mg) as white solid.

IR (nujol) 1659 (C=O) cm$^{-1}$.

NMR (DMSO) δ (ppm) 9.09 (bm, 1H); 8.89 (bm, 1H); 7.83 (s, 1H), 7.52 (s, 2H); 7.45 (dd, 1H); 6.97 (td, 1H), 6.9 (dd, 1H); 4.93 (dd, 1H), 4.39 (dd, 1H); 3.88–3.22 (m, 6H); 3.07 (t, 1H); 2.99 (m, 1H); 2.3 (m, 1H), 2.25 (s, 3H); 1.80 (m, 1H); 1.75 (m, 1H); 1.63(m, 1H).

MS: m/z=504 [MH−HCl]$^+$.

EXAMPLE 28

[2-(3,5-Bis-trifluoromethyl-phenyl)-3,6-dihydro-2H-pyridyn-1-yl]-[2-(S)-(4-fluoro-2-methyl-phenyl)-piperazin-1-yl]-methanone hydrochloride (enantiomer A)

Trifluoroacetic acid (5 mL) was added to a solution of intermediate 62 (172 mg) in DCM (5 mL) and the resulting solution was stirred at r.t. for 30 minutes. The mixture was concentrated in vacuo, then partitioned between 10% potassium carbonate solution and AcOEt. The organic layer was dried and concentrated in vacuo: the residue was dissolved in Et$_2$O and treated with HCl 1M in Et$_2$O (5 mL) the mixture was stirred at r.t. for 30 min, then concentrated in vacuo and the residue triturated with Et$_2$O to give the title compound (90 mg) as white solid.

IR (nujol) 1656 (C=O) cm$^{-1}$.

NMR (DMSO) δ (ppm) 9.4–9.2 (bs, 2H); 7.95 (s, 1H); 7.54 (s, 2H); 7.32 (dd, 1H); 6.98 (dd, 1H), 6.85 (dt, 1H); 5.9 (bm, 1H); 5.72 (m, 1H); 5.47 (d, 1H); 4.57 (dd, 1H); 4.41 (bd, 1H); 3.4–3.25 (m, 5H); 3.14 (t, 1H); 2.91 (t, 1H); 2.72 (dd, 1H); 2.55 (m, 1H), 2.37 (s, 3H).

EXAMPLE 29

[2-(3,5-Bis-trifluoromethyl-phenyl)-piperidin-1-yl]-[2-(S)-(4-fluoro-2-methyl-phenyl)-piperazin-1-yl]-methanone hydrochloride (enantiomer A)

Palladium on charcoal (10%—14 mg) was added to a solution of intermediate 62 (145 mg) in AcOEt (5 mL). The resulting mixture was stirred at 1 atm and r.t. under hydrogen atmosphere for 3 hrs. The mixture was filtered and concentrated in vacuo. DCM (5 mL) and trifluoroacetic acid (5 mL) were added to the residue and the resulting solution was stirred at r.t. for 30 minutes. The mixture was concentrated in vacuo, then partitioned between 10% potassium carbonate solution and AcOEt. The organic layer was dried and concentrated in vacuo: the residue was dissolved in Et$_2$O and treated with HCl 1M in Et$_2$O (5 mL). the mixture was stirred at r.t. for 15 min, then concentrated in vacuo and the residue triturated with Et$_2$O to give the title compound (42 mg) as white solid.

IR (nujol) 3200–2500 (NH$_2$$^+$), 1656 (C=O) cm$^{-1}$.

NMR (DMSO) δ (ppm) 9.4 (bs, 2H); 7.92 (bs, 1H); 7.48 (bs, 2H); 7.43 (dd, 1H); 6.97 (dd, 1H), 6.93 (m, 1H); 5.25 (bm, 1H); 4.61 (dd, 1H); 4.15 (bd, 1H); 3.5–3.2 (bm, 5H); 2.92 (t, 1H); 2.79 (m, 1H); 2.36–2.42 (m, 4H); 1.78–1.58 (m, 4H); 1.17 (m, 1H).

EXAMPLE 30

2-(4-Fluoro-2-methyl-phenyl)-piperazine-1-carboxylic acid [1-(3,5-bis-trifluoromethyl-phenyl)-but-3-enyl]-methyl-amide hydrochloride (diastereoisomer A)

DCM (2 mL) and trifluoroacetic acid (5 mL) were added to intermediate 65 (44 mg) and the resulting solution was stirred at r.t. for 30 minutes. The mixture was concentrated in vacuo, then partitioned between 10% sodium carbonate solution and AcOEt. The organic layer was dried and concentrated in vacuo: the residue was dissolved in Et$_2$O and treated with HCl 1M in Et$_2$O (5 mL). The mixture was stirred at r.t. for 10 min, then concentrated in vacuo to give the title compound (43 mg) as white solid.

NMR (DMSO) δ (ppm) 9.05 (bs, 1H); 8.81 (bs, 1H); 7.96 (bs, 1H); 7.55 (bs, 2H); 7.25 (dd, 1H); 6.97 (dd, 1H), 6.78 (dt, 1H); 5.7 (m, 1H); 5.35 (dd, 1H); 5.22–5.06 (2m, 2H), 4.47 (dd, 1H); 3.5–2.37 (m, 15H).

EXAMPLE 31

2-(4-Fluoro-2-methyl-phenyl)-piperazine-1-carboxylic acid [1-(3,5-bis-trifluoromethyl-phenyl)-but-3-enyl]-methyl-amide hydrochloride (diastereoisomer B)

DCM (2 mL) and trifluoroacetic acid (5 mL) were added to intermediate 66 (44 mg) and the resulting solution was stirred at r.t. for 30 minutes. The mixture was concentrated in vacuo, then partitioned between 10% sodium carbonate solution and AcOEt. The organic layer was dried and concentrated in vacuo: the residue was dissolved in Et$_2$O and treated with HCl 1M in Et$_2$O (5 mL). The mixture was stirred at r.t. for 10 min, then concentrated in vacuo to give the title compound (39 mg) as white solid.

IR (nujol): 3422 (NH$_2$$^+$), 1726 (C=O) cm$^{-1}$

NMR (DMSO) δ (ppm) 9.24 (bm, 1H); 9.02 (bm, 1H); 7.99 (s, 1H); 7.78 (s, 2H); 7.26 (dd, 1H); 6.97 (dd, 1H), 6.87

(dt, 1H); 5.47 (m, 1H); 5.2 (t, 1H); 5.03 (dd, 1H); 4.89 (d, 1H); 4.49 (dd, 1H); 3.36 (m, 2H); 3.24 (m, 2H); 2.97 (m, 2H); 2.85 (s, 3H); 2.74 (t, 2H), 2.37 (s, 3H).

EXAMPLE 32

2-(4-Fluoro-2-methyl-phenyl)-piperazine-1-carboxylic acid [1-(3,5-bis-trifluoromethyl-phenyl)-2-methyl-propyl]-methyl-amide hydrochloride (diastereoisomer A)

Trifluoroacetic acid (1 mL) was added to a solution of intermediate 77a (35 mg) in DCM (1.5 mL) and the resulting solution was stirred at r.t. for 30 minutes. The mixture was concentrated in vacuo, then partitioned between 10% potassium carbonate solution and AcOEt. The organic layer was dried and concentrated in vacuo: the residue was dissolved in $Et_2O$ and treated with HCl 1M in $Et_2O$ (1 mL). The mixture was stirred at r.t. for 10 min, then concentrated in vacuo and the residue triturated with $Et_2O$ to give the title compound (20 mg) as white solid.

NMR ($d_6$-DMSO): δ (ppm) 8.87 (bs, 2H); 8.02 (s, 1H); 7.88 (s, 1H); 7.26 (m, 1H); 6.96 (m, 1H); 6.86 (m, 1H); 4.71 (bm, 1H); 4.42 (dd, 1H); 3.4–3.0 (m, 4H); 2.88–2.79 (m, 5H); 2.63–2.38 (m, 4H); 0.62 (d, 3H); 0.58 (d, 3H).

MS: m/z=520 [M−Cl]$^+$.

EXAMPLE 33

2-(4-Fluoro-2-methyl-phenyl)-piperazine-1-carboxylic acid [1-(3,5-bis-trifluoromethyl-phenyl)-2-methyl-propyl]-methyl-amide hydrochloride (diastereoisomer B)

Trifluoroacetic acid (1 mL) was added to a solution of intermediate 77b (37 mg) in DCM (1.5 mL) and the resulting solution was stirred at r.t. for 30 minutes. The mixture was concentrated in vacuo, then partitioned between 10% potassium carbonate solution and AcOEt. The organic layer was dried and concentrated in vacuo: the residue was dissolved in $Et_2O$ and treated with HCl 1M in $Et_2O$ (1 mL). The mixture was stirred at r.t. for 10 min, then concentrated in vacuo and the residue triturated with $Et_2O$ to give the title compound (20 mg) as white solid.

NMR ($d_6$-DMSO): δ (ppm) 9.14–8.89 (bs, 2H); 7.96 (s, 1H); 7.69 (s, 2H); 7.02–6.95 (dd, 2H); 6.58 (m, 1H); 4.71 (d, 1H); 4.45 (dd, 1H); 3.5–3.2 (m, 4H); 2.95–2.80 (m, 5H); 2.6–2.38 (m, 4H); 0.87 (d, 3H); 0.72 (d, 3H).

MS: m/z=520 [M−Cl]$^+$.

EXAMPLE 34

2(4-Fluoro-2-methyl-phenyl)-piperazine-1-carboxylic acid [(3,5-bis-trifluoromethyl-phenyl)-cyclopropyl-methyl]-methyl-amide hydrochloride (diastereoisomer A)

Conc. HCl (50 μL) was added to a solution of intermediate 80 (10 mg) in methanol (1 mL) and the mixture was refluxed for 15 min. The mixture was concentrated in vacuo and the residue triturated with $Et_2O$ to give the title compound (4 mg) as white solid.

NMR (DMSO) δ (ppm) 9.33 (bm, 1H); 9.16 (m, 1H); 8.0 (bs, 1H), 7.79 (bs, 2H); 7.3 (dd, 1H); 6.95 (m, 2H), 4.48 (dd, 1H), 4.27 (d, 1H); 3.5–2.8 (m, 9H); 2.34 (s, 3H), 1.47 (m, 1H); 0.64 (m, 1H); 0.45 (m, 1H); 0.38 (m, 1H); 0.08 (m, 1H).

EXAMPLE 35

2(3,5-Bis-trifluoromethyl-phenyl)-3,6-dihydro-2H-pyridyn-1-yl]-[2-(4-fluoro-2-methyl-phenyl)-piperazin-1-yl-methanone hydrochloride (diastereoisomer A)

Trifluoroacetic acid (5 mL) was added to a solution of intermediate 68 (172 mg) in DCM (5 mL) and the resulting solution was stirred at r.t. for 30 minutes. The mixture was concentrated in vacuo, then partitioned between 10% potassium carbonate solution and AcOEt. The organic layer was dried and concentrated in vacuo: the residue was dissolved in $Et_2O$ and treated with HCl 1M in $Et_2O$ (5 mL). The mixture was stirred at r.t. for 30 min, then concentrated in vacuo and the residue triturated with $Et_2O$ to give the title compound (90 mg) as white solid.

IR (nujol) 1656 (C=O) cm$^{-1}$.

NMR (DMSO) δ (ppm) 9.23 (bs, 1H); 9.17 (bs, 2H); 7.89 (s, 1H); 7.56 (s, 2H); 7.32 (dd, 1H); 6.95 (dd, 1H), 6.82 (dt, 1H); 5.9 (m, 1H); 5.72 (d, 1H); 5.47 (d, 1H); 4.6 (dd, 1H); 4.4 (m, 1H); 3.4–3.2 (m, 6H); 2.94 (m, 1H); 2.7 (dd, 1H); 2.56 (m, 1H), 2.36 (s, 3H).

EXAMPLE 36

2(S)-(4-Fluoro-2-methyl-phenyl)-piperazine-1-carboxylic acid [1-(R)-(3,5-bis-trifluoromethyl-phenyl)-ethyl]-methyl-amide methansulphonate To a suspension of intermediate 81 (4.9 Kg) in AcOEt (137.2L), triethylamine (5.63L) was added. The mixture was cooled to 0° C. then a solution of diterbuthyl dicarbonate (3.134 Kg) in AcOEt (24.5L) was added in 35 min, maintaining the temperature between 0 and 5° C. The suspension was stirred at 0° C. for 15 min, at 20/250° C. for 1 hr, then washed with water (3×39.2L), concentrated to 24.5L and then added to a solution of triphosgene (1.97 Kg) in AcOEt (24.5L) cooled to 0° C. Triethylamine (3.28L) was then added in 40 min, maintaining the temperature between 0 and 8° C. The suspension was stirred for 1 h and 45 min at 20/25° C. and 30 min at 7° C. and then the solution of intermediate 82 diluted with AcOEt (49L) and triethylamine (2.6L) was added in 30 min. The mixture was refluxed for 15 hrs.

The reaction mixture, cooled at 20/25° C. was treated with aqueous solution of NaOH 10%v/v (36.75L). Organic phase was washed with HCl 4%v/v (46.55L) and NaCl 11.5% p/p (4×24.5L) then concentrated to 14.7L. and diluted with Ciclohexane (39.2L). The mixture was filtered through a silica pad (4.9 Kg) that was washed twice with a mixture of CH/AcOEt 85/15 (2×49L). To the Eluted phases (14.7L) cooled at 20/25° C., methyl tertbutyl ether (49L) and methansulphonic acid (4.067L) were added. The mixture was washed with NaOH 10%v/v (31.85L) then with water (4×31.85L). Organic phase was concentrated to 9.8L, methyl tertbutyl ether (49L) was added and the solution filtered through a 5 micron filter then concentrated to 9.8L. At 20/25° C. MTBE (29.4L) and metansulphonic acid (1.098L) were added. The suspension was refluxed for 10 min, stirred at 20/25° C. for 10 hrs and 2 hrs at 0° C. Then the precipitate was filtered, washed with methyl tertbutyl ether (4.9L) dried under vacuum at 20/25° C. for 24 hrs to obtain the title compound (5.519 Kg.) as white solid.

$^1$H-NMR (DMSO) δ (ppm) 8.99 (bm, 1H); 8.66 (bm, 1H); 8.00 (bs, 1H); 7.69 (bs, 2H); 7.27 (dd, 1H); 7.00 (dd, 1H); 6.83 (m, 1H); 5.32 (q, 1H); 4.47 (dd, 1H); 3.50–3.20 (m, 4H); 2.96 (m, 2H); 2.72 (s, 3H); 2.37 (s, 3H); 2.28 (s, 3H);

1.46 (d, 3H). ES+: m/z 492 [MH–CH$_3$SO$_3$H]$^{+ES-}$: m/z 586 [M–H]$^-$; 95 [CH$_3$SO$_3$]$^-$

EXAMPLE 37

2(S)-(4-Fluoro-2-methyl-phenyl)-piperazine-1-carboxylic acid [1-(R)-(3,5-bis-trifluoromethyl-phenyl)-ethyl]-methyl-amide To a solution of intermediate 40a (15.6 g) in anhydrous THF (94 ml), at 0° C., under N$_2$, BH$_3$.THF 1M/THF (154 ml) was added. The solution was heated at reflux for 3 hr. HCl 37% (54 ml) was slowly added maintaining the reaction mixture in an ice-bath and the reaction mixture was stirred at rt for 1 hr. Water was then added (125 ml) and solid NaHCO$_3$ (62.4 g) was added portionwise until a pH of 6.5. The aqueous phase was extracted with Et$_2$O (4×160 ml) and the combined organic extracts were dried over Na$_2$SO$_4$, the solids were filtered and evaporated to leave a colourless oil which was purified by flash chromatography (silica gel, EtOAc/Methanol 7/3). The obtained product was suspended in Et$_2$O (220 ml) and washed with NaHCO$_3$ sat. (2×36 ml). The combined organic phases were dried (Na$_2$SO$_4$) and evaporated to give the title compound as white foam (8.7 g,).

$^1$H-NMR (CDCl$_3$) δ (ppm) 7.78 (s, 1H); 7.60 (s, 2H); 7.28 (m, 1H); 6.85 (dd, 1H); 6.79 (td, 1H); 5.53 (q, 1H); 4.43 (dd, 1H); 2.9–3.5 (m, 5H); 2.78 (m, 1H), 2.71 (s, 3H); 2.43 (s, 3H); 1.47 (d, 3H).

EXAMPLE 38

2(S)-(4-Fluoro-2-methyl-phenyl)-piperazine-1-carboxylic acid [1(R)-(3,5-bis-trifluoromethyl-phenyl)-ethyl]-methyl-amide hydrochloride Example 37 (0.1 g) was dissolved in Ethyl Ether (0.8 ml) at room temperature, then 1M HCl solution in Ethyl Ether (0.6 ml) was added. The suspension was stirred at 3° C. for 3 hour, then filtered and washed with Ethyl Ether (1 ml) to afford the title compound (0.01 5 g ) as a white solid.

$^1$H-NMR (DMSO) δ (ppm) 9.31 (bm, 1H); 9.11 (bm, 1H); 8.02 (bs, 1H); 7.72 (bs, 2H); 7.28 (dd, 1H); 7.00 (dd, 1H); 6.84 (m, 1H); 5.34 (q, 1H); 4.54 (dd, 1H); 3.50–3.20 (m, 4H); 3.08 (m, 1H); 2.93 (m, 1H); 2.73 (s, 3H); 2.38 (s, 3H); 1.48 (d, 3H).

Pharmacy Examples

| A. Capsules/Tablets | |
|---|---|
| Active ingredient | 20.0 mg |
| Starch 1500 | 2.5 mg |
| Microcrystalline Cellulose | 200.0 mg |
| Croscarmellose Sodium | 6.0 mg |
| Magnesium Stearate | 1.5 mg |

The active ingredient is blended with the other excipients. The blend can be used to fill gelatin capsules or compressed to form tablets using appropriate punches. The tablets can be coated using conventional techniques and coatings.

| B. Tablets | |
|---|---|
| Active ingredient | 20.0 mg |
| Lactose | 200.0 mg |
| Microcrystalline Cellulose | 70.0 mg |
| Povidone | 25.0 mg |
| Croscarmellose Sodium | 6.0 mg |
| Magnesium Stearate | 1.5 mg |

The active ingredient is blended with lactose, microcrystalline cellulose and part of the croscarmellose sodium. The blend is granulated with povidone after dispersing in a suitable solvent (i.e. water). The granule, after drying and comminution is blended with the remaining excipients. The blend can be compressed using appropriate punches and the tablets coated using conventional techniques and coatings.

| c) Bolus | |
|---|---|
| Active ingredient | 2–60 mg/ml |
| Sodium phosphate | 1.0–50.0 mg/ml |
| water for injection qs to | 1 ml |

The formulation may be packed in glass ampoules or vials and syringes with a rubber stopper and a plastic/metal overseal (vials only).

| D) Infusion | |
|---|---|
| Active ingredient | 2–60 mg/ml |
| Infusion solution (NaCl 0.9% or 5% dextrose) | qs to 100 ml |

The formulation may be packed in glass vials or plastic bag.

The affinity of the compound of the invention for NK1 receptor was determined using the NK$_1$-receptor binding affinity method measuring in vitro by the compounds' ability to displace [3H]—substance P (SP) from recombinant human NK$_1$ receptors expressed in Chinese Hamster Ovary (CHO) cell membranes. The affinity values are expressed as negative logarithm of the inhibition constant (Ki) of displacer ligands (pKi).

The pKi values obtained as the average of at least two determinations with representative compounds of the invention are given in the following table:

| Example No | pki |
|---|---|
| 1 | 8.97 |
| 4 | 8.36 |
| 5 | 8.67 |
| 8 | 9.37 |
| 9 | 8.81 |
| 10 | 9 |
| 12 | 8.7 |
| 14 | 8.7 |
| 16 | 9.4 |
| 18 | 9.56 |
| 19 | 9.27 |
| 20 | 9.46 |

-continued

| Example No | pki |
|---|---|
| 21 | 8.95 |
| 22 | 9.39 |
| 23 | 9.32 |
| 24 | 9.18 |
| 25 | 9.32 |
| 28 | 9.31 |
| 29 | 8.87 |
| 30 | 8.78 |
| 32 | 8.59 |
| 34 | 9.10 |
| 36 | 9.81 |

The ability of the compounds of the invention at the nk1 receptor may be determined using the gerbil foot tapping model as described by Rupniak & Williams, Eur. Jour. of Pharmacol., 1994.

The compound was administered orally and one hour later an NK1 agonist (e.g. delta-Aminovaleryl$^6$[Pro$^9$,Me-Leu$^{10}$]-substance P (7-11)) (3 pmol in 5 µL, icv) was infused directly in the cerebral ventricules of the animals. The duration of hind foot tapping induced by the NK1 agonist (e.g. delta-Aminovaleryl$^6$[Pro$^9$,Me-Leu$^{10}$]-substance P (7-11)) was recorded continuously for 3 min using a stop-clock. The dose of the test compound required to inhibit by 50% the tapping induced by the NK1 agonist (e.g. delta-Aminovaleryl$^6$[Pro$^9$,Me-Leu$^{10}$]-substance P (7-11)) expressed as mg/kg was referred as the ID50 values. Alternatively the compounds may be administered subcutaneously or intraperitoneally.

Representative results obtained for compounds of the invention when given by oral administration are given in the following table

| Ex No | ED$_{50}$ (mg/kg po) |
|---|---|
| 19 | 0.04 |
| 20 | 0.065 |
| 21 | 0.4 |
| 36 | 0.05 |

No untoward effects have been observed when compounds of the invention have been administered to the gerbil at the pharmacological active doses.

What is claimed is:

1. A method for the treatment of emesis in a mammal comprising administering to said mammal an effective amount of a compound of formula (I):

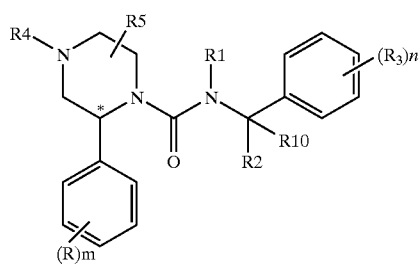

wherein
R is a halogen atom or a $C_{1-4}$ alkyl group;
$R_1$ is hydrogen or a $C_{1-4}$ alkyl group;
$R_2$ is hydrogen, a $C_{1-4}$ alkyl, $C_{2-6}$ alkenyl or a $C_{3-7}$ cycloalkyl group; or $R_1$ and $R_2$ together with nitrogen and carbon atom to which they are attached respectively represent a 5–6 membered heterocyclic group;
$R_3$ is a trifluoromethyl, a $C_{1-4}$ alkyl, a $C_{1-4}$ alkoxy, a trifluoromethoxy or a halogen group;
$R_4$ is hydrogen, a $(CH_2)qR_7$ or a $(CH_2)rCO(CH_2)pR_7$ group;
$R_5$ is hydrogen, a $C_{1-4}$ alkyl or a $COR_6$ group;
$R_6$ is hydrogen, hydroxy, amino, methylamino, dimethylamino, a 5 membered heteroaryl group containing 1 to 3 heteroatoms selected from oxygen, sulphur and nitrogen or a 6 membered heteroaryl group containing 1 to 3 nitrogen atoms;
$R_7$ is hydrogen, hydroxy or $NR_8R_9$ wherein $R_8$ and $R_9$ represent independently hydrogen or $C_{1-4}$ alkyl optionally substituted by hydroxy or by amino;
$R_{10}$ is hydrogen, a C1–4 alkyl group or $R_{10}$ together with $R_2$ represents a $C_{3-7}$ cycloalkyl group;
m is zero or an integer from 1 to 3;
n is zero or an integer from 1 to 3;
both p and r are independently zero or an integer from 1 to 4;
q is an integer from 1 to 4;
provided that, when $R_1$ and $R_2$ together with nitrogen and carbon atom to which they are attached respectively represent a 5 to 6 membered heterocyclic group,
  i) m is 1 or 2;
  ii) when m is 1, B is not fluorine and
  iii) when m is 2, the two substituents R are not both fluorine, or a pharmaceutically acceptable salt or solvate thereof.

2. The method according to claim 1, wherein said mammal is a human.

3. The method according to claim 1, wherein said emesis is delayed emesis.

4. The method according to claim 1, wherein said emesis is anticipatory emesis.

5. The method according to claim 1. wherein said emesis is induced by cancer chemotherapeutic agents.

6. The method according to claim 5, wherein said cancer chemotherapeutic agent is selected from the group consisting of cyclophosphamide, carmustine, lomustine, chlorambucil, dactinomycin, doxorubicin, mitomycin-C, bleomycin, cytarabine, methotrexate, 5-fluorouracil, etoposide, vinblastine, vincristine, cisplatin, dacarbazine, procarbazine and hydroyurea.

7. The method according to claim 1, wherein said emesis is induced by radiation sickness or radiation therapy.

8. The method according to claim 1, wherein said emesis is induced by pregnancy.

9. The method according to claim 1, wherein said emesis is induced by post-operative sickness.

10. The method according to claim 1, wherein said emesis is induced by migraine.

11. The method according to claim 1, wherein said emesis is induced by opiod analgesics.

12. A method for the treatment of emesis in a mammal comprising administering to said mammal an effective amount of a compound selected from the group consisting of
  2-(4-fluoro-2-methyl-phenyl)-piperazine-1-carboxylic acid (3,5-bis-trifluoromethyl-benzyl)-methyl-amide;
  2-(2-Isopropyl-phenyl)-piperazine-1-carboxylic acid (3,5-bis-trifluoromethyl-benzyl)-methyl-amide;
  2-(4-Fluoro-3-methyl-phenyl)-piperazine-1-carboxylic acid (3,5-bis-trifluoromethyl-benzyl)-methyl-amide;

2-(2,4-Difluoro-phenyl)-piperazine-1-carboxylic acid (3,5-bis-trifluoromethyl-benzyl)-methyl-amide;

2-(4-fluoro-2-methyl-phenyl)-piperazine-1-carboxylic acid [1-(3,5-bis-trifluoromethyl-phenyl)ethyl]-methyl-amide;

2-(4-Fluoro-phenyl)-piperazine-1-carboxylic acid (3,4-bis-trifluoromethyl-benzyl)-methyl-amide;

2-Phenyl-piperazine-1-carboxylic acid (3,5-bis-trifluoromethyl-benzyl)-methyl-amide;

2-(2,4-dichloro-phenyl)-piperazine-1-carboxylic acid (3,5-bistrifluoro methyl-benzyl)-methyl-amide;

2-(3,4-dichloro-phenyl-piperazine-1-carboxylic acid (3,5-bistrifluoro methyl-benzyl)-methyl-amide;

2-(4-Fluoro-2-methyl-phenyl)-3-methyl-piperazine-1-carboxylic acid (3,5-bis-trifluoromethyl-benzyl)-methyl-amide;

2-(2-Methyl-4-Fluoro-phenyl)-6-Methyl-piperazine-1-carboxylic acid (3,5-bis-trifluoromethyl-benzyl-methyl-amide;

2-(4-fluoro-2-Methyl-phenyl)-piperazine-1-carboxylic acid [1-(3,5-bis-trifluoromethyl-phenyl)ethyl]-methyl-amide;

4-(2-Amino-acetyl)-2-(S)-(4-fluoro-2-methyl-phenyl)-piperazine-1-carboxylic acid (3,5-bis-trifluoromethyl-benzyl-methyl-amide 2-(S)-(4-Fluoro-2-methyl-phenyl)-4-(piperidine-4-carbonyl)-piperazine-1-carboxylic acid (3,5-bis-trifluoromethyl-benzyl-methyl-amide;

4-(2-Amino-ethyl)-2-(S)-(4-fluoro-2-methyl-phenyl)-piperazine-1-carboxylic acid (3,5-bis-trifluoromethyl-benzyl-methyl-amide;

2-(S)-(4-Fluoro-2-methyl-phenyl-piperazine-1-carboxylic acid [(1-3,5-bis-trifluoromethyl-phenyl-cyclopropyl]-methyl-amide;

[2-(3,5-Bis-trifluoromethyl-phenyl)-pyrrolidin-1-yl]-[2-(S)-(4-fluoro-2-methyl-phenyl)-piperazin-1-yl]-methanone;

[2-(3,5-Bis-trifluoromethyl-phenyl)-3,6-dihydro-2H-pyridyn-1-yl]-(2-(S)-(4-fluoro-2-methyl-phenyl)-piperazin-1-yl]-methanone;

2-(3,5-Bis-trifluoromethyl-phenyl)-piperidin-1-yl]-[2-(S)-(4-fluoro-2-methyl-phenyl)-piperazin-1-yl]-methanone;

2-(4-Fluoro-2-methyl-phenyl)-piperazine-1-carboxylic acid [1-(3,5-bis-trifluoromethyl-phenyl)-but-3-enyl]-methyl-amide;

2-(4-Fluoro-2-methyl-phenyl)-piperazine-1-carboxylic acid [1-(3,5-bis-trifluoromethyl-phenyl-2-methyl-propyl]-methyl-amide;

2-(4-Fluoro-2-methyl-phenyl)-piperazine-1-carboxytic acid [(3,5-bis-trifluoromethyl-phenyl)-cyclopropyl-methyl]-methyl-amide;

or an enantiomer, or pharmaceutically acceptable salt or solvate thereof.

13. The method according to claim 12, wherein said mammal is a human.

14. The method according to claim 12, wherein said emesis is delayed emesis.

15. The method according to claim 12, wherein said emesis is anticipatory emesis.

16. The method according to claim 12, wherein said emesis is induced by cancer chemotherapeutic agents.

17. The method according to claim 16, wherein said cancer chemotherapeutic agent is selected from the group consisting of cyclophosphamide carmustine, lomustine, chlorambucil, dactinomycin, doxorubicin, mitomycin-C, bleomycin, cytarabine, methotrexate, 5-fluorouracil, etoposide, vinblastine, vincristine, cisplatin, dacarbazine, procarbazine and hydroyurea.

18. The method according to claim 12, wherein said emesis is induced by radiation sickness or radiation therapy.

19. The method according to claim 12, wherein said emesis is induced by pregnancy.

20. The method according to claim 12, wherein said emesis is induced by post-operative sickness.

21. The method according to claim 12, wherein said emesis is induced by migraine.

22. The method according to claim 12, wherein said emesis is induced by opiod analgesics.

23. The method according to claim 1, further comprising administering an effective amount of a 5-HT3 antagonist.

24. The method according to claim 23, wherein said 5-HT3 antagonist is selected from the group consisting of ondansetron, granisetron and metoclopramide.

25. The method according to claim 12, further comprising administering an effective amount of a 5-HT3 antagonist.

26. The method according to claim 25, wherein said 5-HT3 antagonist is selected from the group consisting of ondansetron, granisetron and metoclopramide.

27. A method for the treatment of emesis in a mammal comprising administering to said mammal an effective amount of 2-(S)-(4-Fluoro-2-methyl-phenyl)-4-(piperidine-4-carbonyl)-piperazine-1carboxylic acid (3,5-bis-trifluoromethyl-benzyl)-methyl-amide hydrochloride.

28. A method for the treatment of emesis in a mammal comprising administering to said mammal an effective amount of 4-(2-Amino-acetyl)-2-(S)-(4-fluoro-2-methyl-phenyl)-piperazine-1-carboxylic acid (3,5-bis-trifluoromethyl-benzyl)-methyl-amide hydrochloride.

29. A method for the treatment of emesis in a mammal comprising administering to said mammal an effective amount of 2-(S)-(4-Fluoro-2-methyl-phenyl)-piperazine-1-carboxylic acid [1-(R)-(3,5-bis-trifluoromethyl-phenyl)-ethyl]-methyl-amide methanesulphonate.

30. A method for the treatment of emesis in a mammal comprising administering to said mammal an effective amount of 2-(S)-(4-Flouro-2-methyl-phenyl-piperazine-1-carboxylic acid [1-(R)-(3,5-bis-trifluoromethyl-phenyl)-ethyl]-methyl-amide acetate.

31. A method for the treatment of emesis in a mammal comprising administering to said mammal an effective amount of 2-(S)-(4-Fluoro-2-methyl-phenyl)-piperazine-1-carboxylic acid [1-(R)-(3,5-bis-trifluoromethyl-phenyl)-ethyl]-methyl-amide or an enantiomer or pharmaceutically acceptable salt or solvate thereof.

* * * * *

UNITED STATES PATENT AND TRADEMARK OFFICE
CERTIFICATE OF CORRECTION

PATENT NO. : 6,642,240 B2
DATED : November 4, 2003
INVENTOR(S) : Alvaro et al.

It is certified that error appears in the above-identified patent and that said Letters Patent is hereby corrected as shown below:

Column 63,
Line 31, reads "2-(S)-(4-Fluoro-2-methyl-phenyl-piperazine-1-" should read
-- 2-(S)-(4-Fluoro-2-methyl-phenyl)-piperazine-1- --
Line 35, reads "carboxylic acid [(1-3,5-bis-trifluoromethyl-phenyl-" should read
-- carboxylic acid [(1-3,5-bis-trifluoromethyl-phenyl)- --
Line 48, reads "acid [1-(3,5-bis-trifluoromethyl-phenyl-2-methyl-" should read
-- acid [1-(3,5-bis-trifluoromethyl-phenyl)-2-methyl- --
Line 51, reads "2-(4-Fluoro-2-methyl-phenyl)-piperazine-1-carboxytic" should read
-- 2-(4-Fluoro-2-methyl-phenyl)-piperazine-1-carboxylic --

Column 64,
Line 9, reads "consisting of cyclophosphamide carmustine, lomustine" should read
-- consisting of cyclophosphamide, carmustine, lomustine --.
Line 50, reads "amount of 2-(S)-(4-Flouro-2-methyl-phenyl-piperazine-1-"should read
-- amount of 2-(S)-(4-Flouro-2-methyl-phenyl)-piperazine-1- --.

Signed and Sealed this

Twentieth Day of April, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,642,240 B2
DATED : November 4, 2003
INVENTOR(S) : Alvaro et al.

It is certified that error appears in the above-identified patent and that said Letters Patent is hereby corrected as shown below:

Title page,
Item [54], Title, "TREATING EMESIS IN A MAMMAL" should read
-- CHEMICAL COMPOUNDS --

Column 62,
Line 30, reads "ii) when m is 1, B is not fluorine and" should read -- ii) when m is 1, R is not fluorine and --

Column 63,
Line 12, reads "2-(3,4-dichloro-phenyl-piperazine-1-carboxylic acid (3.5-" should read
-- 2-(3,4-dichloro-phenyl)-piperazine-1-carboxylic acid (3.5- --
Line 18, reads "carboxylic acid (3,5-bis-trifluoromethyl-benzyl-" should read
-- carboxylic acid (3,5-bix-trifluoromethyl-benzyl)- --
Line 25, reads "benzyl-methyl-amide" should read -- benzyl)-methyl-amide --
Line 28, reads "trifluoromethyl-benzyl-methyl-amide;" should read -- trifluoromethyl-benzyl)-methyl-amide; --
Line 31, reads "benzyl-methyl-amide" should read -- benzyl)-methyl-amide --
Line 32, reads "2-(S)-(4-Fluoro-2-methyl-phenyl-piperazine-1-" should read
-- 2-(S)-(4-Fluoro-2-methyl-phenyl)-piperazine-1- --
Line 33, reads "carboxylic acid [(1-3,5-bis-trifluoromethyl-phenyl-" should read
-- carboxylic acid [(1-3,5-bis-trifluoromethyl-phenyl)- --
Line 48, reads "acid [1-(3,5-bis-trifluoromethyl-phenyl-2-methyl-" should read
-- acid [1-(3,5-bis-trifluoromethyl-phenyl)-2-methyl- --
Line 50, reads "2-(4-Fluoro-2-methyl-phenyl)-piperazine-1-carboxytic" should read
-- 2-(4-Fluoro-2-methyl-phenyl)-piperazine-1-carboxylic --

UNITED STATES PATENT AND TRADEMARK OFFICE
CERTIFICATE OF CORRECTION

PATENT NO. : 6,642,240 B2
DATED : November 4, 2003
INVENTOR(S) : Alvaro et al.

It is certified that error appears in the above-identified patent and that said Letters Patent is hereby corrected as shown below:

Column 64,
Line 9, reads "consisting of cyclophosphamide carmustine, lomustine" should read
-- consisting of cyclophosphamide, carmustine, lomustine --.
Line 50, reads "amount of 2-(S)-(4-Flouro-2-methyl-phenyl-piperazine-1-"should read
-- amount of 2-(S)-(4-Flouro-2-methyl-phenyl)-piperazine-1- --.

This certificate supersedes Certificate of Correction issued April 20, 2004.

Signed and Sealed this

Nineteenth Day of July, 2005

JON W. DUDAS
*Director of the United States Patent and Trademark Office*